(12) United States Patent
Gross

(10) Patent No.: US 10,004,557 B2
(45) Date of Patent: Jun. 26, 2018

(54) CONTROLLED TISSUE ABLATION

(71) Applicant: Rainbow Medical Ltd., Herzliya (IL)

(72) Inventor: Yossi Gross, Moshav Mazor (IL)

(73) Assignee: PYTHAGORAS MEDICAL LTD., Herzliya (IL)

( * ) Notice: Subject to any disclaimer, the term of this patent is extended or adjusted under 35 U.S.C. 154(b) by 330 days.

(21) Appl. No.: 14/440,431

(22) PCT Filed: Nov. 3, 2013

(86) PCT No.: PCT/IL2013/050903
§ 371 (c)(1),
(2) Date: May 4, 2015

(87) PCT Pub. No.: WO2014/068577
PCT Pub. Date: May 8, 2014

(65) Prior Publication Data
US 2015/0245867 A1    Sep. 3, 2015

Related U.S. Application Data

(63) Continuation-in-part of application No. 13/771,853, filed on Feb. 20, 2013, now Pat. No. 9,770,593.
(Continued)

(51) Int. Cl.
*A61B 18/04*    (2006.01)
*A61B 18/14*    (2006.01)
(Continued)

(52) U.S. Cl.
CPC ........ *A61B 18/1492* (2013.01); *A61B 5/0215* (2013.01); *A61B 2018/0016* (2013.01);
(Continued)

(58) Field of Classification Search
CPC .......... A61B 5/0215; A61B 2018/0016; A61B 2018/00404; A61B 2018/00434;
(Continued)

(56) References Cited

U.S. PATENT DOCUMENTS

| 4,106,488 A | 8/1978 | Gordon |
| 4,569,836 A | 2/1986 | Gordon |

(Continued)

FOREIGN PATENT DOCUMENTS

| CA | 2900160 | 8/2014 |
| CA | 2956945 | 2/2016 |

(Continued)

OTHER PUBLICATIONS

Buch E et al., "Intra-pericardial balloon retraction of the left atrium: A novel method to prevent esophageal injury during catheter ablation," Heart Rhythm 2008;5:1473-1475.
(Continued)

*Primary Examiner* — Mallika D Fairchild
(74) *Attorney, Agent, or Firm* — Sughrue Mion, PLLC

(57) ABSTRACT

A catheter (28) has a distal portion that comprises an electrode unit (22) and an ablation unit (24). A control unit (32) is configured: (i) to receive a preliminary blood pressure value (BPV), (ii) to receive a target excited BPV, (iii) to iteratively: (a) drive the electrode unit to apply an excitatory current to nerve of a renal artery (8), (b) receive a detected excited BPV, and (c) alter a value of a property of the excitatory current, until the detected excited BPV crosses a first threshold, and (iv) subsequently, to iteratively: (d) drive the ablation unit to apply ablating energy to the nerve, (e) subsequently, drive the electrode unit to apply a selected excitatory current to the nerve, and (f) receive a detected ablated BPV, until the detected ablated BPV crosses a second threshold. Other embodiments are also described.

22 Claims, 22 Drawing Sheets

Related U.S. Application Data

(60) Provisional application No. 61/722,293, filed on Nov. 5, 2012, provisional application No. 61/811,880, filed on Apr. 15, 2013, provisional application No. 61/841,485, filed on Jul. 1, 2013, provisional application No. 61/862,561, filed on Aug. 6, 2013.

(51) Int. Cl.
*A61B 5/0215* (2006.01)
*A61N 1/36* (2006.01)
*A61B 18/00* (2006.01)

(52) U.S. Cl.
CPC ............. *A61B 2018/0072* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00672* (2013.01); *A61B 2018/00678* (2013.01); *A61B 2018/00708* (2013.01); *A61B 2018/00839* (2013.01); *A61B 2018/00863* (2013.01); *A61B 2018/00994* (2013.01); *A61B 2018/1467* (2013.01); *A61N 1/36071* (2013.01); *A61N 1/36117* (2013.01)

(58) Field of Classification Search
CPC ........... A61B 2018/00511; A61B 2018/00642; A61B 2018/00672; A61B 2018/00678; A61B 2018/00708; A61B 2018/0072; A61B 2018/00839; A61B 2018/00863; A61B 2018/00994; A61B 2018/1467; A61N 1/36071; A61N 1/36117
See application file for complete search history.

(56) References Cited

U.S. PATENT DOCUMENTS

| | | |
|---|---|---|
| 4,619,247 A | 10/1986 | Inoue |
| 5,215,086 A | 6/1993 | Terry, Jr. et al. |
| 5,251,634 A | 10/1993 | Weinberg |
| 5,697,377 A | 12/1997 | Wittkampf |
| 5,735,280 A | 4/1998 | Sherman et al. |
| 5,776,063 A | 7/1998 | Dittrich et al. |
| 5,807,285 A | 9/1998 | Vaitekunas |
| 5,817,022 A | 10/1998 | Vesely |
| 5,827,216 A | 10/1998 | Igo et al. |
| 6,050,943 A | 4/2000 | Slayton |
| 6,064,902 A | 5/2000 | Haissaguerre et al. |
| 6,117,101 A | 9/2000 | Diederich |
| 6,128,523 A | 10/2000 | Bechtold |
| 6,161,048 A | 12/2000 | Sluijter |
| 6,219,577 B1 | 4/2001 | Brown |
| 6,233,477 B1 | 5/2001 | Chia |
| 6,241,727 B1 | 6/2001 | Tu |
| 6,246,899 B1 | 6/2001 | Chia |
| 6,361,500 B1 | 3/2002 | Masters |
| 6,405,732 B1 | 6/2002 | Edwards |
| 6,425,877 B1 | 7/2002 | Edwards |
| 6,440,077 B1 | 8/2002 | Jung |
| 6,522,926 B1 | 2/2003 | Kieval |
| 6,526,318 B1 | 2/2003 | Ansarinia |
| 6,605,084 B2 | 8/2003 | Acker et al. |
| 6,635,054 B2 | 10/2003 | Fjield et al. |
| 6,641,579 B1 | 11/2003 | Bernardi |
| 6,659,950 B2 | 12/2003 | Taheri |
| 6,671,556 B2 | 12/2003 | Osorio et al. |
| 6,684,105 B2 | 1/2004 | Cohen et al. |
| 6,685,639 B1 | 2/2004 | Wang |
| 6,692,490 B1 | 2/2004 | Edwards |
| 6,701,931 B2 | 3/2004 | Sliwa et al. |
| 6,736,835 B2 | 5/2004 | Pellegrino |
| 6,740,040 B1 | 5/2004 | Mandrusov |
| 6,805,129 B1 | 10/2004 | Pless et al. |
| 6,845,267 B2 | 1/2005 | Harrison |
| 7,001,336 B2 | 2/2006 | Mandrusov |
| 7,022,105 B1 | 4/2006 | Edwards |
| 7,037,306 B2 | 5/2006 | Podany et al. |
| 7,149,574 B2 | 12/2006 | Yun |
| 7,162,303 B2 | 1/2007 | Levin |
| 7,226,440 B2 | 6/2007 | Gelfand et al. |
| 7,311,701 B2 | 12/2007 | Gifford et al. |
| 7,326,201 B2 | 2/2008 | Fjield et al. |
| 7,430,449 B2 | 9/2008 | Aldrich |
| 7,499,747 B2 | 3/2009 | Kieval |
| 7,510,536 B2 | 3/2009 | Foley |
| 7,553,284 B2 | 6/2009 | Vaitekunas |
| 7,565,191 B2 | 7/2009 | Burbank et al. |
| 7,617,005 B2 | 11/2009 | Demarais |
| 7,653,438 B2 | 1/2010 | Deem |
| 7,662,099 B2 | 2/2010 | Podany et al. |
| 7,684,865 B2 | 3/2010 | Aldrich |
| 7,706,882 B2 | 4/2010 | Francischelli |
| 7,717,948 B2 | 5/2010 | Demarais |
| 7,787,946 B2 | 8/2010 | Stahmann et al. |
| 7,840,271 B2 | 11/2010 | Kieval |
| 7,853,333 B2 | 12/2010 | Demarais |
| 7,854,733 B2 | 12/2010 | Govari |
| 7,901,359 B2 | 3/2011 | Mandrusov |
| 7,974,696 B1 | 7/2011 | DiLorenzo |
| 8,197,409 B2 | 6/2012 | Foley |
| 8,391,970 B2 | 3/2013 | Tracey et al. |
| 8,585,601 B2 | 11/2013 | Sverdlik et al. |
| 8,696,581 B2 | 4/2014 | Sverdlik et al. |
| 8,702,619 B2 | 4/2014 | Wang |
| 9,014,821 B2 | 4/2015 | Wang |
| 9,028,417 B2 | 5/2015 | Sverdlik et al. |
| 9,381,063 B2 | 7/2016 | Gang et al. |
| 9,408,549 B2 | 8/2016 | Brockway et al. |
| 9,566,456 B2 | 2/2017 | Sverdlik et al. |
| 2001/0003798 A1 | 6/2001 | McGovern |
| 2001/0007940 A1 | 7/2001 | Tu |
| 2002/0091427 A1 | 7/2002 | Rappaport |
| 2002/0147446 A1 | 10/2002 | Ein-Gal |
| 2002/0173688 A1 | 11/2002 | Chen |
| 2003/0018256 A1 | 1/2003 | Sasaki |
| 2003/0045909 A1 | 3/2003 | Gross et al. |
| 2003/0055421 A1 | 3/2003 | West |
| 2003/0069590 A1 | 4/2003 | Rabiner |
| 2003/0013968 A1 | 6/2003 | Fjield |
| 2004/0034339 A1 | 2/2004 | Stoller |
| 2004/0038857 A1 | 2/2004 | Tracey |
| 2004/0097788 A1 | 5/2004 | Mourlas |
| 2004/0122494 A1 | 6/2004 | Eggers et al. |
| 2004/0162507 A1 | 8/2004 | Govari et al. |
| 2004/0162550 A1 | 8/2004 | Govari et al. |
| 2004/0193021 A1 | 9/2004 | Savage |
| 2005/0020921 A1 | 1/2005 | Glassell |
| 2005/0080469 A1 | 4/2005 | Larson et al. |
| 2005/0165298 A1 | 7/2005 | Larson |
| 2005/0192638 A1 | 9/2005 | Gelfand |
| 2005/0203410 A1 | 9/2005 | Jenkins |
| 2005/0251125 A1 | 11/2005 | Pless |
| 2005/0288651 A1 | 12/2005 | Van Tassel et al. |
| 2006/0009753 A1 | 1/2006 | Fjield et al. |
| 2006/0041277 A1 | 2/2006 | Deem |
| 2006/0058711 A1 | 3/2006 | Harhen et al. |
| 2006/0100514 A1 | 5/2006 | Lopath |
| 2006/0184048 A1 | 8/2006 | Saadat |
| 2006/0206150 A1 | 9/2006 | Demarais |
| 2006/0212076 A1 | 9/2006 | Demarais |
| 2006/0212078 A1 | 9/2006 | Demarais |
| 2006/0241523 A1 | 10/2006 | Sinelnikov et al. |
| 2006/0265014 A1 | 11/2006 | Demarais |
| 2006/0265015 A1 | 11/2006 | Demarais |
| 2006/0271111 A1 | 11/2006 | Demarais |
| 2006/0276852 A1 | 12/2006 | Demarais |
| 2006/0287648 A1 | 12/2006 | Schwartz |
| 2007/0004984 A1 | 1/2007 | Crum et al. |
| 2007/0021803 A1 | 1/2007 | Deem |
| 2007/0038259 A1 | 2/2007 | Kieval |
| 2007/0060972 A1 | 3/2007 | Kieval |
| 2007/0093420 A1 | 4/2007 | Yeomans |
| 2007/0112327 A1 | 5/2007 | Lee |

(56) References Cited

U.S. PATENT DOCUMENTS

| | | |
|---|---|---|
| 2007/0129760 A1 | 6/2007 | Demarais |
| 2007/0129761 A1 | 6/2007 | Demarais |
| 2007/0133849 A1 | 6/2007 | Young et al. |
| 2007/0135875 A1 | 6/2007 | Demarais |
| 2007/0142879 A1 | 6/2007 | Greenberg |
| 2007/0162085 A1 | 6/2007 | DiLorenzo |
| 2007/0167984 A1 | 6/2007 | Kieval |
| 2007/0173899 A1 | 7/2007 | Levin et al. |
| 2007/0191906 A1 | 8/2007 | Caparso |
| 2007/0203549 A1 | 8/2007 | Demarais |
| 2007/0239077 A1 | 10/2007 | Azhari et al. |
| 2007/0265610 A1 | 11/2007 | Thapliyal et al. |
| 2007/0265687 A1 | 11/2007 | Deem |
| 2007/0282407 A1 | 12/2007 | Demarais |
| 2008/0004614 A1 | 1/2008 | Burdette |
| 2008/0015445 A1 | 1/2008 | Saadat |
| 2008/0033415 A1 | 2/2008 | Rieker et al. |
| 2008/0039746 A1 | 2/2008 | Francischelli |
| 2008/0058682 A1 | 3/2008 | Azhari et al. |
| 2008/0058702 A1 | 3/2008 | Arndt |
| 2008/0071173 A1 | 3/2008 | Aldrich |
| 2008/0091109 A1 | 4/2008 | Abraham |
| 2008/0108984 A1 | 5/2008 | Burdette |
| 2008/0125819 A1 | 5/2008 | Ben-David et al. |
| 2008/0172104 A1 | 7/2008 | Kieval |
| 2008/0183248 A1 | 7/2008 | Rezai |
| 2008/0215111 A1 | 9/2008 | Kieval |
| 2008/0255449 A1 | 10/2008 | Sinelnikov |
| 2008/0255642 A1 | 10/2008 | Zarins |
| 2008/0281379 A1 | 11/2008 | Wesselink |
| 2008/0288017 A1 | 11/2008 | Kieval |
| 2008/0288031 A1 | 11/2008 | Kieval |
| 2008/0306570 A1 | 12/2008 | Rezai |
| 2008/0319513 A1 | 12/2008 | Pu |
| 2009/0024195 A1 | 1/2009 | Rezai et al. |
| 2009/0048514 A1 | 2/2009 | Azhari |
| 2009/0062790 A1 | 3/2009 | Malchano |
| 2009/0062873 A1 | 3/2009 | Wu et al. |
| 2009/0076409 A1 | 3/2009 | Wu |
| 2009/0112133 A1 | 4/2009 | Deisseroth |
| 2009/0118780 A1 | 5/2009 | DiLorenzo |
| 2009/0137900 A1 | 5/2009 | Bonner et al. |
| 2009/0155336 A1 | 6/2009 | Rezai |
| 2009/0187230 A1 | 6/2009 | DiLorenzo |
| 2009/0192506 A9 | 7/2009 | Vaska et al. |
| 2009/0234407 A1 | 9/2009 | Hastings et al. |
| 2009/0247912 A1 | 10/2009 | Warnking |
| 2009/0287274 A1 | 11/2009 | Ridder |
| 2009/0326511 A1 | 12/2009 | Shivkumar |
| 2010/0004704 A1 | 1/2010 | Mazgalev |
| 2010/0010567 A1 | 1/2010 | Deem |
| 2010/0036292 A1 | 2/2010 | Darlington et al. |
| 2010/0042170 A1 | 2/2010 | Caparso |
| 2010/0105993 A1 | 4/2010 | Hassan |
| 2010/0113928 A1 | 5/2010 | Thapliyal |
| 2010/0130836 A1 | 5/2010 | Malchano |
| 2010/0137860 A1 | 6/2010 | Demarais |
| 2010/0137949 A1 | 6/2010 | Mazgalev |
| 2010/0137952 A1 | 6/2010 | Demarais et al. |
| 2010/0145428 A1 | 6/2010 | Cameron |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais |
| 2010/0191112 A1 | 7/2010 | Demarais |
| 2010/0204741 A1 | 8/2010 | Tweden |
| 2010/0217162 A1 | 8/2010 | Francischelli |
| 2010/0217369 A1 | 8/2010 | Gross |
| 2010/0222851 A1 | 9/2010 | Deem |
| 2010/0222854 A1 | 9/2010 | Demarais |
| 2010/0234728 A1 | 9/2010 | Foley |
| 2010/0256436 A1 | 10/2010 | Partsch |
| 2010/0268297 A1 | 10/2010 | Neisz |
| 2010/0305392 A1 | 12/2010 | Gross et al. |
| 2010/0312094 A1 | 12/2010 | Guttman et al. |
| 2011/0009734 A1 | 1/2011 | Foley |
| 2011/0015548 A1 | 1/2011 | Aldrich |
| 2011/0022133 A1 | 1/2011 | Bradford |
| 2011/0040171 A1 | 2/2011 | Foley |
| 2011/0040214 A1 | 2/2011 | Foley |
| 2011/0060324 A1 | 3/2011 | Wu |
| 2011/0092781 A1 | 4/2011 | Gertner |
| 2011/0092880 A1 | 4/2011 | Gertner |
| 2011/0112394 A1 | 5/2011 | Mishelevich |
| 2011/0112400 A1 | 5/2011 | Emery |
| 2011/0118598 A1 | 5/2011 | Gertner |
| 2011/0118600 A1 | 5/2011 | Gertner |
| 2011/0118725 A1 | 5/2011 | Mayse |
| 2011/0137149 A1 | 6/2011 | Gertner |
| 2011/0137298 A1 | 6/2011 | Chen |
| 2011/0172527 A1 | 6/2011 | Gertner |
| 2011/0172528 A1 | 6/2011 | Gertner |
| 2011/0172529 A1 | 6/2011 | Gertner |
| 2011/0178570 A1 | 6/2011 | Demarais |
| 2011/0184337 A1 | 6/2011 | Evans |
| 2011/0178541 A1 | 7/2011 | Azhari |
| 2011/0184322 A1 | 7/2011 | Brawer |
| 2011/0251524 A1 | 10/2011 | Azhari |
| 2011/0257564 A1 | 10/2011 | Demarais et al. |
| 2011/0282203 A1 | 11/2011 | Tsoref |
| 2011/0282249 A1 | 11/2011 | Tsoref |
| 2011/0306851 A1 | 12/2011 | Wang |
| 2012/0089047 A1 | 4/2012 | Ryba et al. |
| 2012/0095371 A1 | 4/2012 | Sverdlik et al. |
| 2012/0130363 A1 | 5/2012 | Kim |
| 2012/0150049 A1 | 6/2012 | Zielinski et al. |
| 2012/0157992 A1 | 6/2012 | Smith et al. |
| 2012/0172680 A1 | 7/2012 | Gelfand et al. |
| 2012/0197198 A1 | 8/2012 | Demarais |
| 2012/0265198 A1 | 10/2012 | Crow et al. |
| 2012/0265227 A1 | 10/2012 | Sverdlik et al. |
| 2012/0290024 A1 | 11/2012 | Zhang et al. |
| 2012/0296240 A1 | 11/2012 | Azhari |
| 2012/0296329 A1 | 11/2012 | Ng |
| 2013/0012866 A1 | 1/2013 | Deem |
| 2013/0013024 A1 | 1/2013 | Levin |
| 2013/0103028 A1 | 4/2013 | Tsoref |
| 2013/0165926 A1 | 6/2013 | Mathur |
| 2013/0204242 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218029 A1 | 8/2013 | Cholette et al. |
| 2013/0218054 A1 | 8/2013 | Sverdlik et al. |
| 2013/0218068 A1 | 8/2013 | Sverdlik et al. |
| 2013/0274735 A1 | 10/2013 | Hastings et al. |
| 2013/0289369 A1 | 10/2013 | Margolis |
| 2013/0303876 A1 | 11/2013 | Gelfand et al. |
| 2013/0310823 A1 | 11/2013 | Gelfand et al. |
| 2013/0322724 A1 | 12/2013 | Florent et al. |
| 2013/0324987 A1 | 12/2013 | Leung et al. |
| 2013/0324989 A1 | 12/2013 | Leung et al. |
| 2013/0331813 A1 | 12/2013 | Barbut et al. |
| 2014/0005706 A1 | 1/2014 | Gelfand et al. |
| 2014/0012133 A1 | 1/2014 | Sverdlik et al. |
| 2014/0018788 A1 | 1/2014 | Engelman et al. |
| 2014/0088561 A1 | 3/2014 | Levin et al. |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0243809 A1 | 8/2014 | Gelfand et al. |
| 2014/0257263 A1 | 9/2014 | Azamian et al. |
| 2014/0276063 A1 | 9/2014 | Park et al. |
| 2014/0276742 A1 | 9/2014 | Nabutovsky et al. |
| 2015/0011843 A1 | 1/2015 | Toth et al. |
| 2015/0045649 A1 | 2/2015 | O'Dea et al. |
| 2015/0073400 A1 | 3/2015 | Sverdlik et al. |
| 2015/0148601 A1 | 5/2015 | Weiner et al. |
| 2015/0164401 A1 | 6/2015 | Toth et al. |
| 2015/0173673 A1 | 6/2015 | Toth et al. |
| 2015/0216590 A1 | 8/2015 | Wang et al. |
| 2015/0224326 A1 | 8/2015 | Toth et al. |
| 2015/0257779 A1 | 9/2015 | Sinelnikov et al. |
| 2015/0289929 A1 | 10/2015 | Toth et al. |

(56) References Cited

U.S. PATENT DOCUMENTS

| | | | |
|---|---|---|---|
| 2015/0297113 | A1 | 10/2015 | Kassab et al. |
| 2015/0297139 | A1 | 10/2015 | Toth |
| 2016/0000499 | A1 | 1/2016 | Lennox et al. |
| 2016/0106498 | A1 | 4/2016 | Highsmith et al. |
| 2016/0113699 | A1 | 4/2016 | Sverdlik et al. |
| 2016/0128767 | A1 | 5/2016 | Azamian et al. |
| 2016/0324572 | A1 | 11/2016 | Gross et al. |
| 2017/0007157 | A1 | 1/2017 | Gross et al. |
| 2017/0007158 | A1 | 1/2017 | Gross et al. |
| 2017/0172651 | A1 | 6/2017 | Gross et al. |

FOREIGN PATENT DOCUMENTS

| | | | |
|---|---|---|---|
| CN | 102551878 | A | 7/2012 |
| CN | 203089369 | U | 7/2013 |
| EP | 2460486 | A1 | 6/2012 |
| WO | 1999/40957 | | 8/1999 |
| WO | 03/097162 | | 11/2003 |
| WO | 2006/072928 | | 7/2006 |
| WO | 07/134258 | | 11/2007 |
| WO | 2009/073208 | | 6/2009 |
| WO | 2010/067360 | | 6/2010 |
| WO | 2011/024159 | | 3/2011 |
| WO | 2011/141918 | | 11/2011 |
| WO | 2012/100211 | | 7/2012 |
| WO | 2012/120495 | | 9/2012 |
| WO | 2012/122157 | | 9/2012 |
| WO | 2013/030738 | | 3/2013 |
| WO | 2013/030743 | | 3/2013 |
| WO | 2013/049601 | | 4/2013 |
| WO | 2013/121424 | | 8/2013 |
| WO | 2013111136 | A2 | 8/2013 |
| WO | 2013157009 | A2 | 10/2013 |
| WO | 2014/029355 | A1 | 2/2014 |
| WO | 2014/068577 | | 5/2014 |
| WO | 2014/071223 | | 5/2014 |
| WO | 2014/123512 | | 8/2014 |
| WO | 2014/160832 | A2 | 10/2014 |
| WO | 2014/175853 | | 10/2014 |
| WO | 2015/057696 | A1 | 4/2015 |
| WO | 2015/138225 | | 9/2015 |
| WO | 2015/170281 | | 11/2015 |
| WO | 2015/175948 | | 11/2015 |

OTHER PUBLICATIONS

Cassak D, "Endosense: Facing technology and financing challenges in AF," In-Vivo: The Business & Medicine Report, 36-44, Mar. 2010.
Di Biase L et al., "Prevention of phrenic nerve injury during epicardial ablation: Comparison of methods for separating the phrenic nerve from the epicardial surface," Heart Rhythm 2009;6:957-961.
Matsuo S et al., "Novel technique to prevent left phrenic nerve injury during epicardial catheter ablation," Circulation 2008;117:e471.
Nakahara S et al., "Intrapericardial balloon placement for prevention of collateral injury during catheter ablation of the left atrium in a porcine model," Heart Rhythm 2010;7:81-87.
Shen J et al., "The surgical treatment of atrial fibrillation Heart Rhythm," vol. 6, No. 8S, August Supplement 2009.
Sacher F et al., "Phrenic Nerve Injury After Catheter Ablation of Atrial Fibrillation," Indian Pacing Electrophysiol J. Jan.-Mar. 2007; 7(1): 1-6.
A Restriction Requirement dated Feb. 25, 2013, which issued during the prosecution of U.S. Appl. No. 12/780,240.
Tanaka S et al., "Development of a new vascular endoscopic system for observing inner wall of aorta using intermittent saline jet" World Congress on Medical Physics and Biomedical Engineering, Sep. 7-12, 2009, Munich, Germany.
Tearney GJ et al., "Three-Dimensional coronary artery microscopy by intracoronary optical frequency domain imaging" JACC Cardiovasc Imaging. Nov. 2008; 1(6): 752-761.
U.S. Appl. No. 61/722,293, filed Nov. 5, 2012.
William E. Cohn, et al., "Contrast pericardiography facilitates intrapericardial navigation under fluoroscopy", Ann Thorac Surg 2010; 90: 1537-40. Accepted for publication Jun. 7, 2010.
Srijoy Mahapatra, et al., "Pressure frequency characteristics of the pericardial space and thorax during subxiphoid access for epicardial ventricular tachycardia ablation", Heart Rhythm 2010; 7:604-609.
Schuessler RB et al., "Animal studies of epicardial atrial ablation," Heart Rhythm, vol. 6, No. 12S, S41-S45, Dececember Supplement 2009.
An International Search Report and a Written Opinion both dated Oct. 26, 2011, which issued during the prosecution of Applicant's PCT/IL11/00382.
An International Search Report and a Written Opinion both dated Sep. 17, 2012, which issued during the prosecution of Applicant's PCT/IL2012/000100.
An International Preliminary Report on Patentability dated Nov. 20, 2012, which issued during the prosectuion of Applicant's PCT/IL11/00382.
An International Search Report dated Jul. 31, 2008, which issued during the prosecution of Applicant's PCT/US07/68818.
An Office Action dated Dec. 20, 2012, which issued during the prosecution of U.S. Appl. No. 11/653,115.
An Office Action dated Feb. 19, 2013, which issued during the prosecution of U.S. Appl. No. 13/010,555.
Fajardo et al., Effects of Hyperthermia in a Maligant Tumor, Cancer 45:613-623 (1980).
Short et al., Physical Hyperthermia and Cancer Therapy, Proceedings of the IEEE 68:133-142 (1980) p. 136, col. 2, para 6.
U.S. Appl. No. 60/370,190, filed Apr. 8, 2002.
U.S. Appl. No. 60/307,124, filed Jul. 23, 2001.
An Office Action dated May 17, 2013, which issued during the prosecution of U.S. Appl. No. 12/780,240.
An Invitation to pay additional fees dated Jun. 7, 2013, which issued during the prosecution of Applicant's PCT/IL2013/050134.
An International Search Report and a Written Opinion both dated Aug. 12, 2013 which issued during the prosecution of Applicant's PCT/IL2013/050134.
An International Search Report and a Written Opinion both dated Feb. 18, 2011 which issued during the prosecution of Applicant's PCT/IL2010/000683.
An International Preliminary Report of patentability dated Feb. 28, 2012 which issued during the prosecution of Applicant's PCT/IL2010/000683.
F. Mahfoud et al., Catherter-Based renal denervation increases insulin sensitivity and improves glucose metabolism. European Heart Journal 2010.
U.S. Appl. No. 61/811,880, filed Apr. 15, 2013.
Tai et al., Analysis of Nerve Conduction Including by Direct Current, J Comput Neuro. Published Online on 2009.
Ariav et al., Electrical Stimulation Induced Relaxation of Isolated Pig Aortas, Scientific Sessions 2011. American Heart Association. Abstract.
U.S. Appl. No. 61/841,485, filed Jul. 1, 2013.
U.S. Appl. No. 61/862,561, filed Aug. 6, 2013.
Stella et al., Effects of afferent renal nerve stimulation on renal hemodynamic and excretory functions, American Journal of physiology, 576-583, 1984.
Renal Sympathetic denervation in patients with treatment resistant hypertension, (1-7) Published online Nov. 2010.
Zhang et al., Mechanism of Nerve conduction Block induced by High-Frequency Biphasic Electrical Currents, IEEE Biomedical Engineering vol. 53 No. 12, 2006.
Bhadra et al., Reduction of the Onset Response in High-Frequency Nerve Block with Amplitude Ramps from Non-Zero Amplitudes, 650-653, 2009 IEEE.
Tai et al., Stimulation of Nerve Block by High-Frequency Sinusoidal Electrical Current Based on the Hodgkin-Huxley Model, IEEE Neural Systems and Rehabilitation engineering, vol. 13 No. 3, 2005.
Tsui, Electrical Nerve Stimulation, Springer Atlas of Ultrasound, pp. 9-18, 2008.

(56) References Cited

OTHER PUBLICATIONS

Bartus et al., Denervation (ablation) of Nerve Terminalis in renal arteries: early results of interventional treatment of arterial hypertension in Poland, Kardiologia Polska 2013, 71, 2: 152-158.
Krum et al., Catherter-Based Renal sympathetic denervation for resistant hypertension: A multicentre safety and proof-of-principle cohort study, Lancet 2009.
Chinushi M. et al., Blood pressure and autonomic responses to electrical stimulation of the renal arterial nerve before and after ablation of the renal artery, Pubmed, Hyper tension, Feb. 2013 61;(2) 450-6.
Wojakowski and Tendera, Renal sympathetic nerve in pathopysiology of resistant hypertension, European Society of Cardiology, downloaded on Jun. 2013.
Chinushi et al., Hemodynamic Responses and Histological Effects of Radiofrequency catheter Ablation to renal artery Sympathetic nerve. Abstract, downloaded on Jun. 2013.
Berjano, Biomedical Engineering Online Theoretical modeling for Radiofrequency Ablation: state-of-the-art and challenges for the future, published Apr. 2006.
Young and Henneman, Reversible block of nerve Conduction by Ultrasound, Archive of Neurology vol. 4, 1961.
Ballantine et al., Focal Destruction of nervous tissue by focused ultrasound : Biophysical factors influencing its Application, Medical Acoustics Research Group, 1956.
Colucci et al., Focused Ultrasound effects on nerve action potential in vitro, Department of Radiology, Harvard Medical Scholl, Ultrasound Med Biolog. 2009, 35(10); 1773-174.
Damianou, MRI Monitoring of the effects of tissue interfaces in the penetration of high intensity focused ultrasound in kidney in vivo, Ultrasound in Med & Bilo., vol. 30 No. 9, 2004.
Daum et al., In vivo Demonstration of noninvasive thermal surgery of the liver and kidney using an ultrasonic phase array, Ultrasound in Med & Bilo., vol. 25 No. 7, 1087-1098, 1999.
Foley et al., Image guided HIFU Neurolysis of peripheral nerve to treat Spasticity and Pain, Ultrasound in Med & Bilo., vol. 30 No. 9, 1199-1207, 2004.
Foley et al., Image guided High-Intensity focused Ultrasound for Condition block of peripheral nerves, Biomed Engineering, vol. 35 No. 1, 2007.
Zhang and Solomon, Nerve Ablation by high Intensity focused Ultrasound (HIFU) in swine model: Investigating HIFU as a non invasive Nerve block tool, WCIO 2011. Abstract.
Hynynen et al., Noninvasive arterial occlusion using MRI-Guided focused Ultrasound, Ultrasound in Med & Bilo., vol. 22 No. 8, 1071-1077, 1996.
Iwamoto et al., focused Ultrasound for Tactile Felling display, ICAT 2001.
Lele, Effects of Ultrasonic radiation on peripheral Nerve, with Observation on local Hearting, Experimental Neurology 8, 47-83, 1963.
Miharn et al., Temporally-Specific modification of Myelinated Axon excitability in vitro following a single ultrasound pulse,Ultrasound in Med & Bilo., 1990.
Rubin et al., Acute effects of Ultrasound on skeletal muscle oxygen tension , blood flow and capillary density, Ultrasound in Med & Bilo., vol. 16 No. 3, 271*277, 1990.
Renal sympathetic nerve ablation for Uncontrolled Hypertension, The New England journal of medicine, 932-934, 2009.
Wu et al., Preliminary Experience using high Intensity focused Ultrasound for the treatment of patient with advanced stage renal malignancy. The Journal of Urology, vol. 170, 2237-2240, 2003.
Young and Henneman, Functional Effects of focused Ultrasound on Mammalian nerves, Science New Series, vol. 134, No. 3489, 1961, 1521-1522.
Mizelle et al., Role of Renal nerve in Compensatory adaptation to chronic reduction in sodium intake, American Physiological Society, 1987.
Gibson, The Present Status of Renal Sympathectomy, California and Western Medicine, vol. 45, No. 1, 1936.

Kassab et al., Renal Denervation Attenuates the Sodium Retention and Hypertension Associated With Obesity, Hypertension, 1997. Abstract.
Winternitz et al., Role of the Renal Sympathetic Nerves in the Development and Maintenance of Hypertension in the Spontaneously Hypertensive Rat, J. Clin Invest 66(5), 1980. Abstract.
Augustyniak et al., Sympathetic overactivity as a cause of hypertension in chronic renal failure, Hypertension vol. 20, Issue 1, 2002. Abstract.
Brief introduction to bioimpedance (from www.ucl.ac.uk-medphys-research-eit).
Fletcher, Effect of episodic hypoxia on sympathetic activity and blood pressure, Respyration Pysiology, vol. 119, issue 2-3, 2000. Abstract.
Fletcher et al., Blood pressure response to chronic episodic hypoxia: the renin-angiotensin system, Journal of Applied physiology, 2001.
Illis, Spinal Cord Synapses in the Cat: The Reaction of the Boutons Termineaux at the Motoneurone Surface to Experimental Denervation, Brain a Journal of Neurology, vol. 87 issue 3, 1963, First page only.
Kopelman et al., Upper dorsal thoracoscopic sympathectomy for palmar hyperhidrosis. The use of harmonic scalpel versus diathermy. Ann Chir Gynaecol. 2001;90(3):203-5. Abstract.
Hashmonai et al., Thoracoscopic sympathectomy for palmar hyperhidrosis, Surgical Endoscopy May 2001, vol. 15, Issue 5, pp. 435-441.
Yoshimoto et al., Relationship between renal sympathetic nerve activity and renal blood flow during natural behavior in rats, American Journal of Physiology vol. 286, 2004.
DiBona. Dynamic Analysis of patterns of renal sympathetic nerve activity: Implications of renal functions, Exp Physiol. 90.2 pp. 159-161, 2004.
Valente et al., Laparoscopic renal denervation for intractable ADPKD-related pain, Nephrology Dialysis Transplantation vol. 6 issue 1, 2000.
An Advisory Action dated Aug. 8, 2016, which issued during the prosecution of U.S. Appl. No. 13/771,853.
An International Preliminary Report on Patentability dated Nov. 8, 2016, which issued during the prosecution of Applicant's PCT/IB2015/053350.
European Search Report dated Jun. 7, 2016, which issued during the prosecution of Applicant's European App No. 13850508.6.
mananatomy.com, 'Duodenum' http://www.mananatomy.com/digestive-system/duodenum.
Rosas-Ballina et al., 'Splenic nerve is required for cholinergic anti-inflammatory pathway control of TNF in endotoxemia' Aug. 5, 2008, vol. 105, No. 31 www.pnas.org/cgi/doi10.1073/pnas. 0803237105.
An International Search Report and a Written Opinion both dated Apr. 17, 2014 which issued during the prosecution of Applicant's PCT/IL2013/050903.
Luscher TF, Mahfoud F. Renal nerve ablation after symplicity htn-3: Confused at the higher level? Eur Heart J. 2014;35:1706-1711.
Straub et al., 'A bacteria-induced switch of sympathetic effector mechanisms augments local inhibition of TNF-a and IL-6 secretion in the spleen' Jul. 2000 The FASEB Journal vol. 14 No. 10 1380-1388.
Gestel et al., 'Autonomic dysfunction in patients with chronic obstructive pulmonary disease (COPD)' J Thorac Dis 2010; 2:215-222.
Hering et al., 'Renal Denervation in Moderate to Severe CKD' J Am Soc Nephrol. [Jul. 2012]; 23(7): 1250-1257.
Jonson et al, 'Afferent electrical stimulation of mesenteric nerves inhibits duodenal HC03 secretion via a spinal reflex activation of the splanchnic nerves in the rat' [1988] Acta Physiologica Scandinavica, 133: 545-550. doi: 10.1111/j.1748-1716.1988. tb08439.x.
Jonson et al., 'Splanchnic nerve stimulation inhibits duodenal HC03—secretion in the rat' Am J Physiol. [Dec. 1988];255 (6 Pt 1):G709-12.
Schwan, H.P. and Kay, C.F., 1956. Specific resistance of body tissues.*Circulation Research*, 4(6), pp. 664-670.

(56) References Cited

OTHER PUBLICATIONS

Kees et al., 'Via beta-adrenoceptors, stimulation of extrasplenic sympathetic nerve fibers inhibits lipopolysaccharideinduced TNF secretion in perfused rat spleen' J Neuroimmunol. Dec. 2003,145(1-2):77-85.
pcta.org, 'New (Dec. 6, 2013) Medtronic Multi-Electrode Renal Denervation Device Gets CE Mark and Australian Approval' http://www.ptca.org/news/2013/1206_MEDTRONIC_SYMPLICITY.html.
BusinessWire, 'St. Jude Medical Receives European Approval for New Renal Denervation System That Reduces Total Ablation Time by More Than 80 Percent' (Aug. 29, 2013) 2013 European Society of Cardiology.
Krum, H., et al. "Device-based antihypertensive therapy: therapeutic modulation of the autonomic nervous system." Circulation 123.2 (2011): 209.
Kilgore, Kevin L., et al. "Combined direct current and high frequency nerve block for elimination of the onset response." Engineering in Medicine and Biology Society, 2009. EMBC 2009. Annual International Conference of the IEEE. IEEE, 2009.
Bohm (2014) Symplicity HTN-3 trial_ what is it and what does it mean?
Ruilope (2014) Was there real denervation in the Symplicity HTN-3 trial.
"Blood pressure response to renal nerve stimulation in patients undergoing renal denervation: a feasibility study" , Gal et al., Journal of Human Hypertension (2014), 1-4, Macmillan Publishers Limited.
Sarafidis PA, Bakris GL. Resistant hypertension: An overview of evaluation and treatment. J Am Coll Cardiol. 2008;52:1749-1757.
Renal Catheterization—SymplicityTM Renal Denervation System—downloaded from medtronicrdn.com Jun. 26, 2013.
An Office Action dated Mar. 11, 2016, which issued during the prosecution of U.S. Appl. No. 13/771,853.
Persu A, Jin Y, Fadl Elmula FE, Jacobs L, Renkin J, Kjeldsen S. Renal denervation after symplicity htn-3: An update.Curr Hypertens Rep. 2014;16:460.
Renal denervation and symplicity htn-3: "Dubium sapientiae initium" (doubt is the beginning of wisdom). Circ Res. 2014;115:211-214.
Patel HC, Hayward C, Di Mario C. Symplicity htn 3: The death knell for renal denervation in hypertension? Glob Cardiol Sci Pract. 2014;2014:94-98.
An Office Action dated Jan. 8, 2015, which issued during the prosecution of U.S. Appl. No. 13/771,853.
An International Preliminary Report on Patentability dated May 5, 2015, which issued during the prosecution of Applicant's PCT/IL2013/050903.
Warchol-Celinska E, Januszewicz A, Prejbisz A, Kadziela J. Renal denervation after the symplicity htn-3 trial. Postepy Kardiol Interwencyjnej. 2014;10:75-77.
Mahfoud F, Cremers B, Janker J, Link B, Vonend O, Ukena C, Linz D, Schmieder R, Rump LC, Kindermann I, Sobotka PA, Krum H, Scheller B, Schlaich M, Laufs U, Bohm M. Renal hemodynamics and renal function after catheter-based renal sympathetic denervation in patients with resistant hypertension. Hypertension. 2012;60:419-424.
Kjeldsen SE, Fadl Elmula FE, Persu A, Jin Y, Staessen JA. Renal sympathetic denervation in the aftermath of symplicity htn-Blood Press. 2014;23:256-261.
Calhoun DA, Jones D, Textor S, Goff DC, Murphy TP, Toto RD, White A, Cushman WC, White W, Sica D, Ferdinand K, Giles TD, Falkner B, Carey RM. Resistant hypertension: Diagnosis, evaluation, and treatment: A scientific statement from the American Heart Association professional education committee of the council for high blood pressure research Circulation. 2008.
Schlaich MP, Sobotka PA, Krum H, Whitbourn R, Walton A, Esler MD. Renal denervation as a therapeutic approach for hypertension: Novel implications for an old concept. Hypertension. 2009;54:1195-1201.

Esler MD, Bohm M, Sieved H, Rump CL, Schmieder RE, Krum H, Mahfoud F, Schlaich MP. Catheter-based renal denervation for treatment of patients with treatment-resistant hypertension: 36 month results from the Symplicity htn-2 randomized clinical trial. Eur Heart J. 2014;35:1752-1759.
Kandzari DE, Bhatt DL, Sobotka PA, O'Neill WW, Esler M, Flack JM, Katzen BT, Leon MB, Massaro JM, Negoita M, Oparil S, Rocha-Singh K, Straley C, Townsend RR, Bakris G. Catheter-based renal denervation for resistant hypertension: Rationale and design of the symplicity htn-3 trial. Clin Cardiol. 2012;35:528-535.
Krum H, Schlaich MP, Sobotka PA, Bohm M, Mahfoud F, Rocha-Singh K, Katholi R, Esler MD. Percutaneous renal denervation in patients with treatment-resistant hypertension: Final 3-year report of the symplicity htn-1 study. Lancet. 2014;383:622-629.
Esler M. Illusions of truths in the symplicity htn-3 trial: Generic design strengths but neuroscience failings. J Am Soc Hypertens. 2014;8:593-598.
Schmieder RE. Hypertension: How should data from symplicity htn-3 be interpreted? Nat Rev Cardiol. 2014;11:375-376.
Pathak A, Ewen S, Fajadet J, Honton B, Mahfoud F, Marco J, Schlaich M, Schmieder R, Tsioufis K, Ukena C, Zeller T. From symplicity htn-3 to the renal denervation global registry: Where do we stand and where should we go? Eurointervention. 2014;10:21-23.
Pokushalov, Evgeny, et al. "A randomized comparison of pulmonary vein isolation with versus without concomitant renal artery denervation in patients with refractory symptomatic atrial fibrillation and resistant hypertension." Journal of the American College of Cardiology 60.13 (2012): 1163-1170.
Ruilope, L.M. and Arribas, F., 2014. Resistant Hypertension and Renal Denervation. Considerations on the Results of the Symplicity HTN-3 Trial.Revista Española de Cardiología, 67(11), pp. 881-882.
An English translation of an Office Action dated Nov. 18, 2016, which issued during the prosecution of Chinese Patent Application No. 2013800692612.
International Search Report and Written Opinion dated Aug. 11, 2015 from the International Searching Authority in counterpart International Application No. PCT/IB2015/053350.
Schwarz et al;(2015) Autonomix presentation at TCT—Guidewire-Based Autonomic Neural Sensing From the Artery Lumen.
Communication dated Aug. 21, 2015 from the U.S. Patent and Trademark Office in counterpart U.S. Appl. No. 13/771,583.
Lu (2015) Selective Proximal Renal Denervation Guided by Autonomic Responses Evoked via High-Frequency Stimulation in a Preclinical Canine Model.
Changfeng (2009) Analysis of nerve conduction block induced by direct current.
Tsui (2008) Chapter 2 of Atlas of ultrasound and nerve stimulation guided regional anesthesia.
Stella (1987) Cardiovascular effects of afferent renal nerve stimulation.
Changfeng (2005) Simulation of nerve block by high frequency sunusoidal electrical current.
Mortimer (2004) Peripheral nerve and muscle stimulation (Chapter 4.2 in 'Neuroprosthetics theory and practice', p. 638-632).
Mahfoud (2011) Renal sympathetic denervation on glucose metabolism in patients with resistant hypertension.
Esler (2010) Renal sympathetic denervation in patients with treatment-resistant hypertension (The Symplicity HTN-2 Trial).
An International Search Report and a Written Opinion both dated May 24, 2017, which issued during the prosecution of Applicant's PCT/IL2017/050029.
An Invitation to pay additional fees dated Mar. 28, 2017, which issued during the prosecution of Applicant's PCT/IL2017/050029.
Notice of Allowance together with the English translation dated May 4, 2017 which issued during the prosecution of Chinese Patent Application No. 2013800692612.
An Office Action dated Apr. 6, 2017, which issued during the prosecution of U.S. Appl. No. 13/771,853.
An Invitation to pay additional fees dated Sep. 11, 2017, which issued during the prosecution of Applicant's PCT/IL2017/050533.
European Search Report dated May 9, 2017, which issued during the prosecution of Applicant's European App No. 16203956.4.

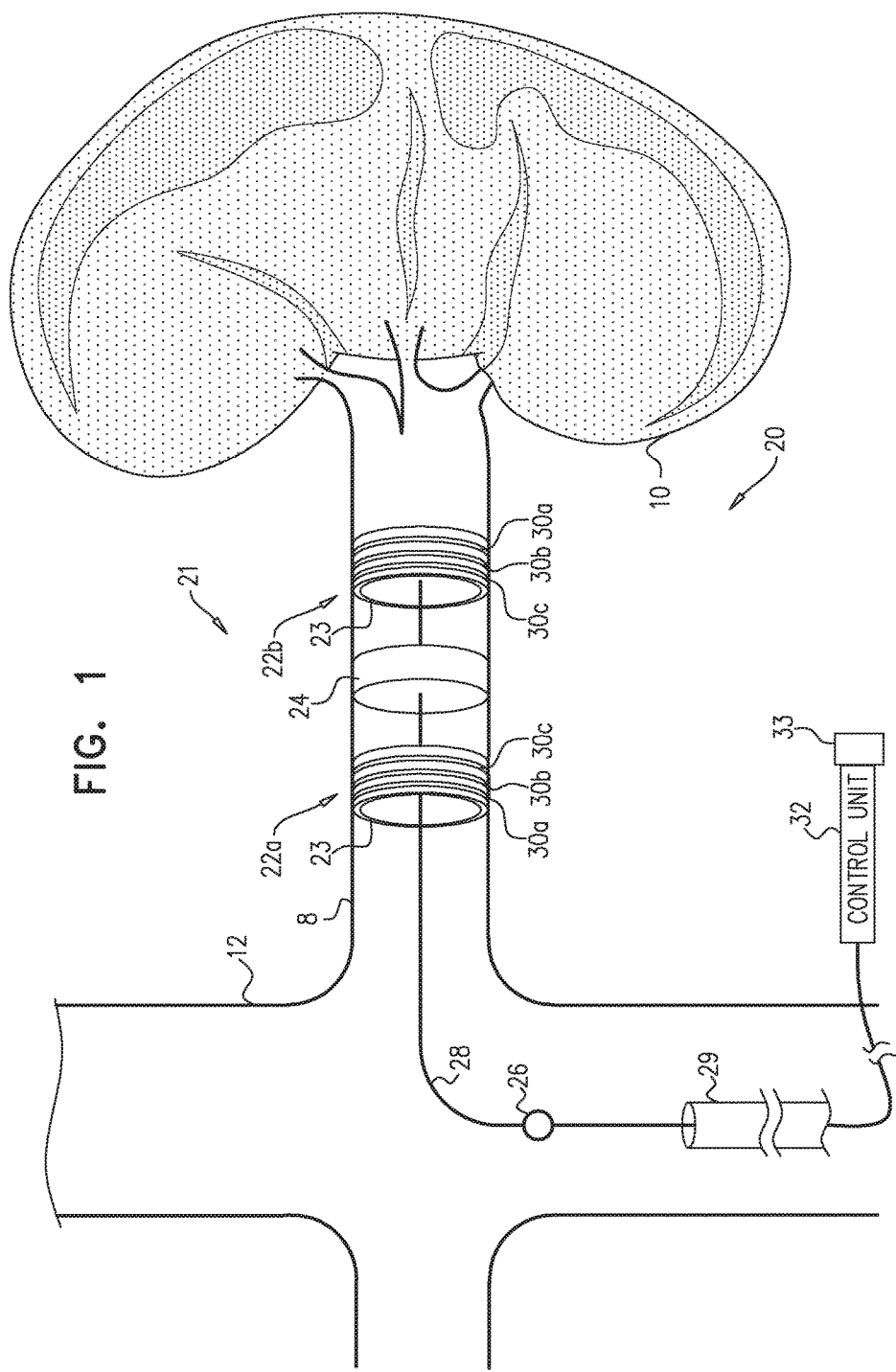

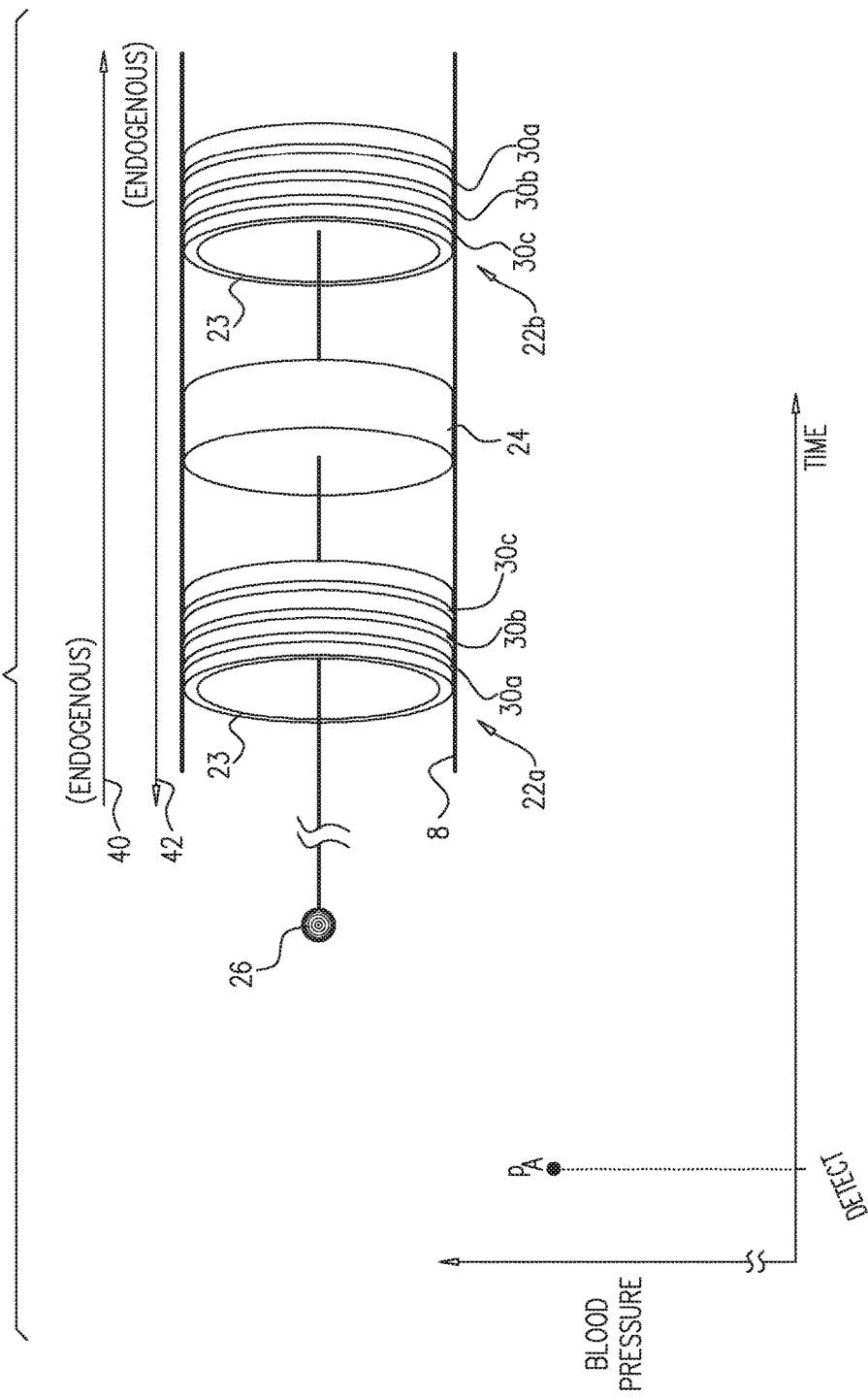

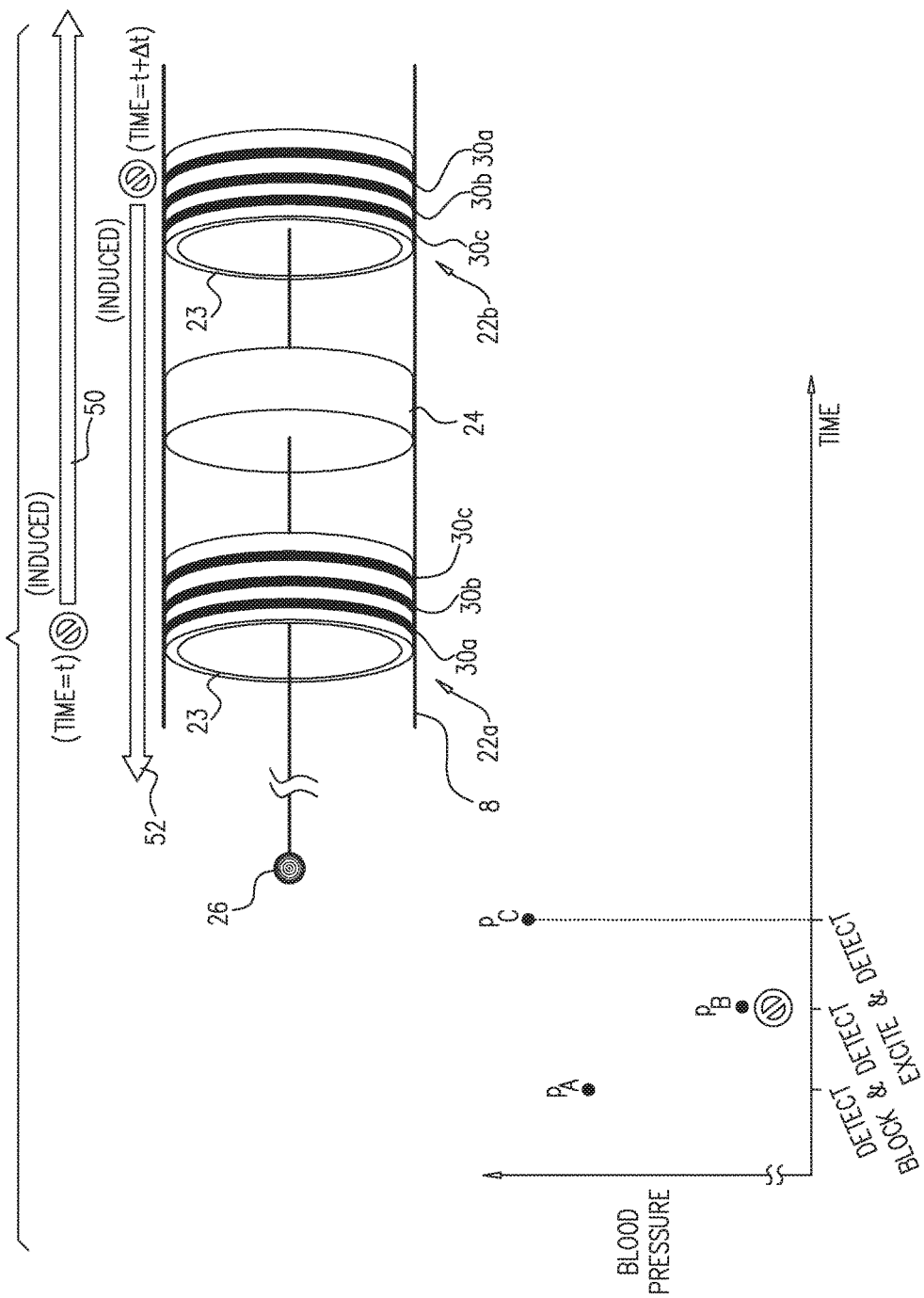

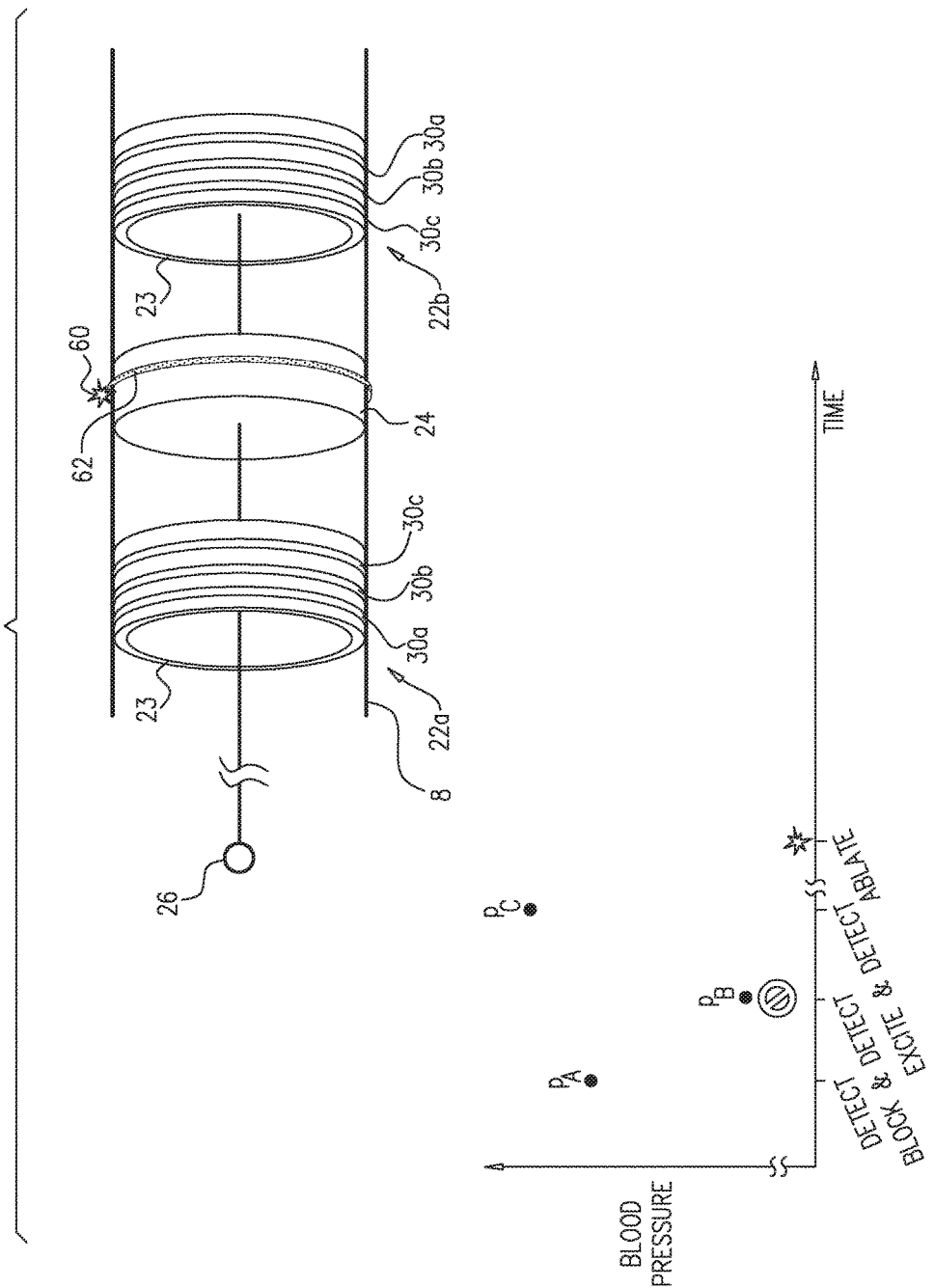

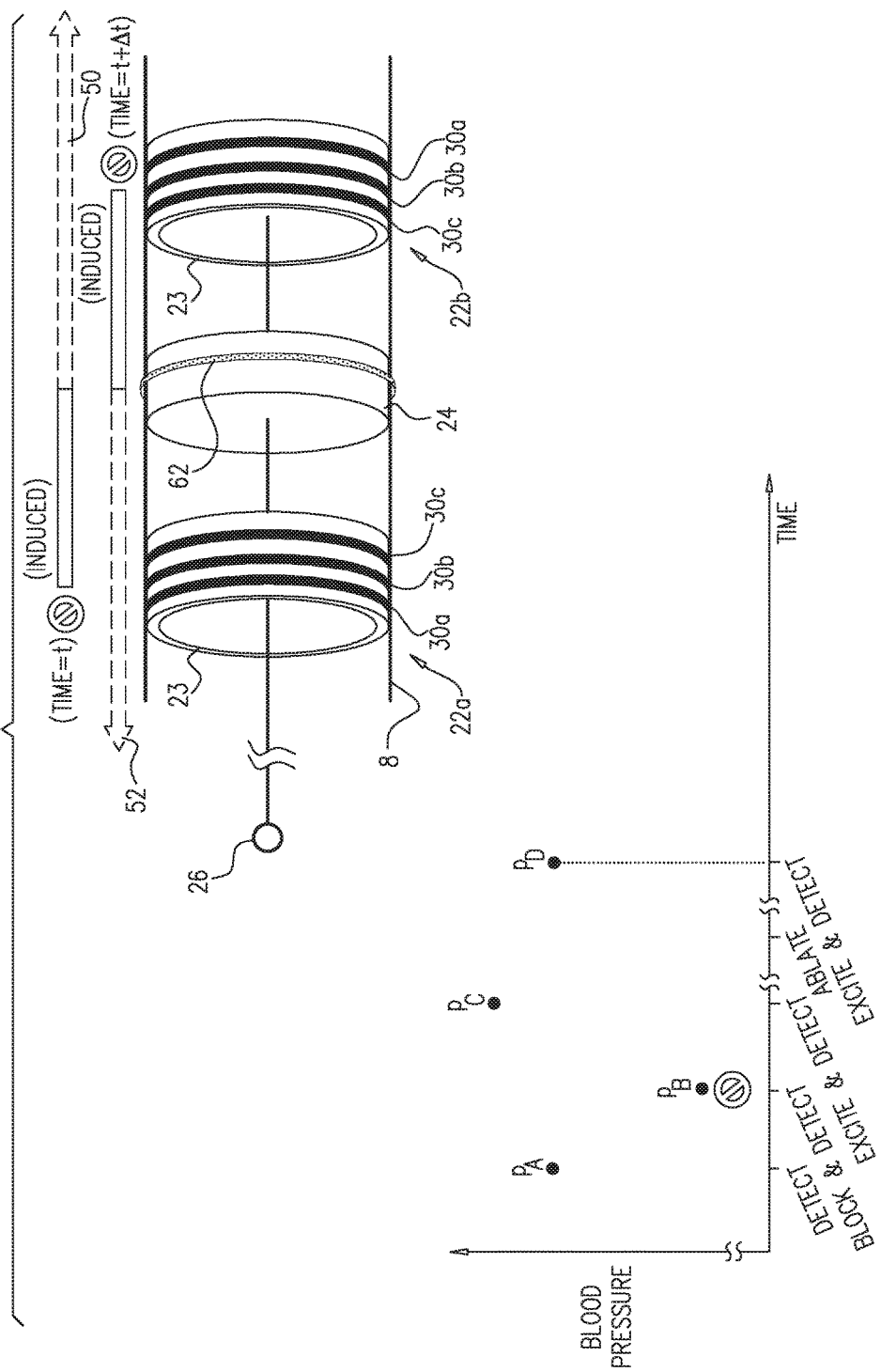

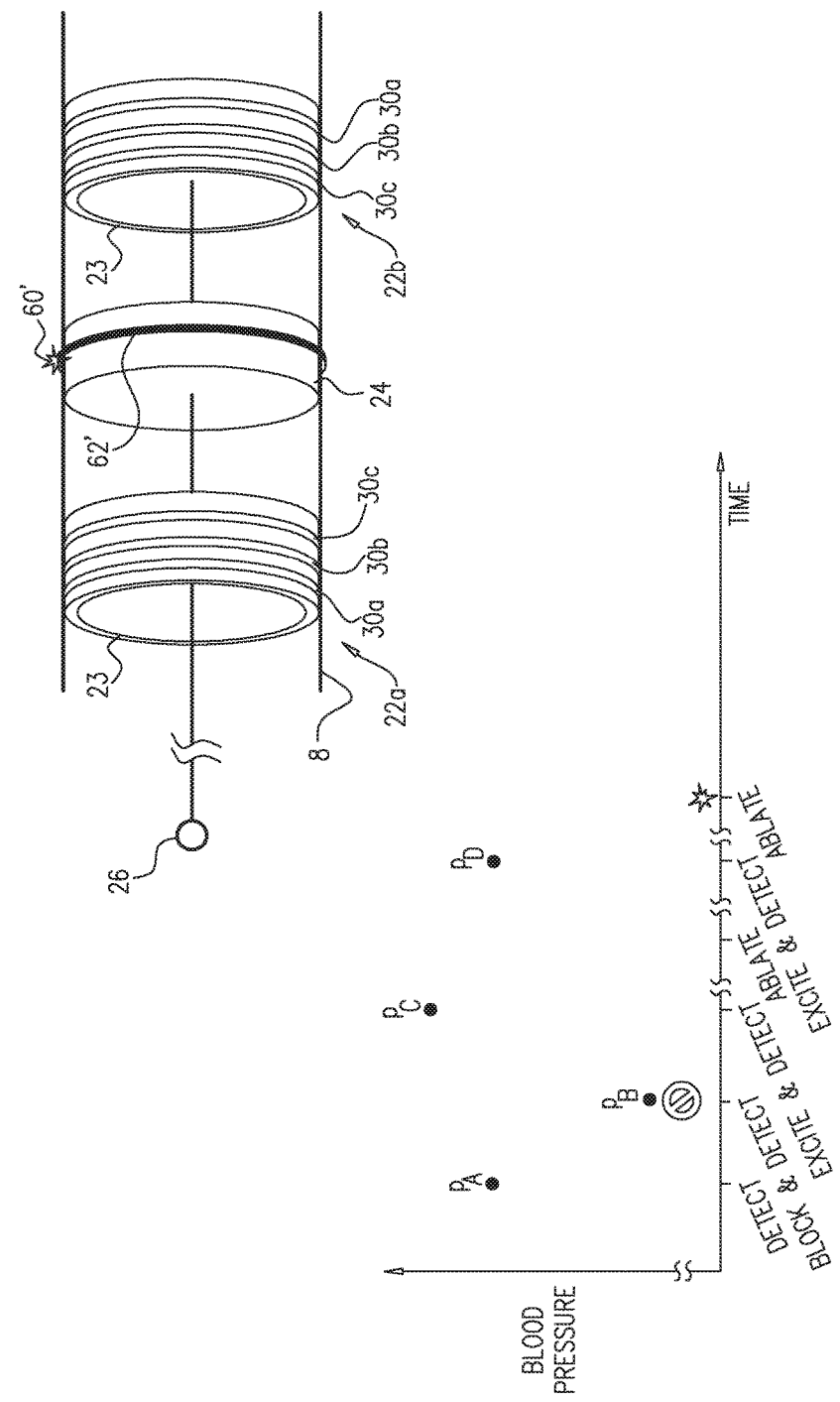

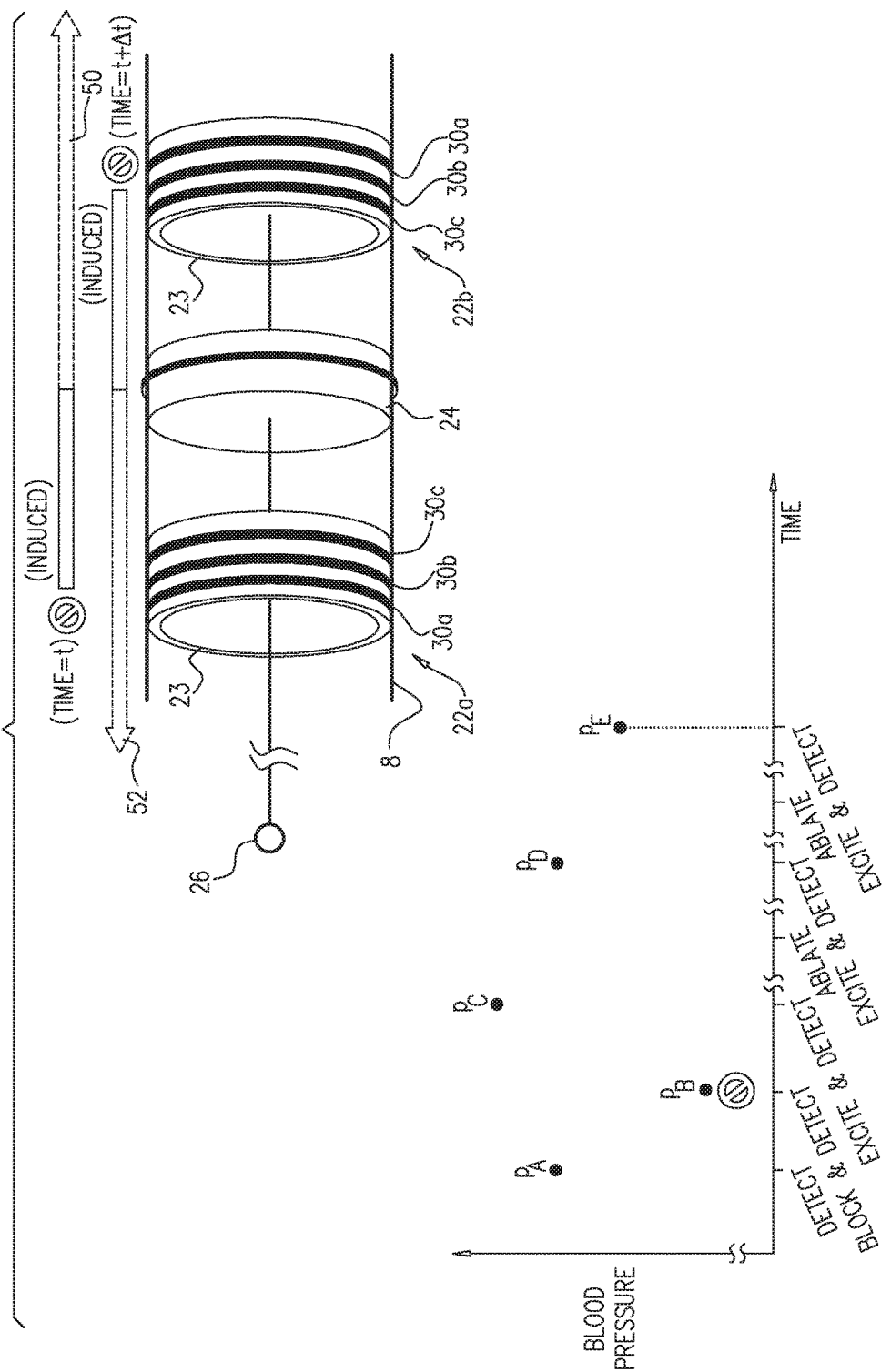

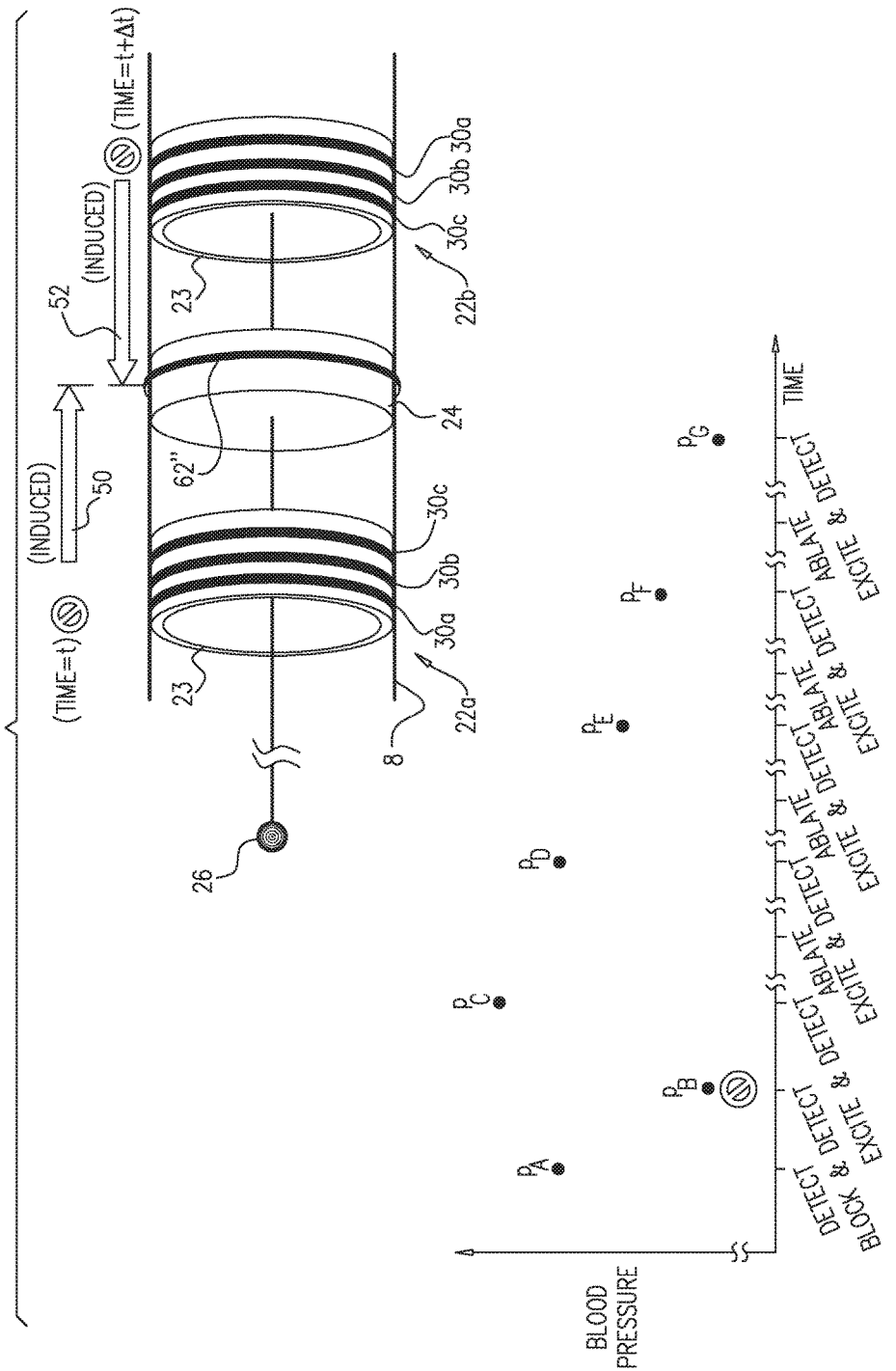

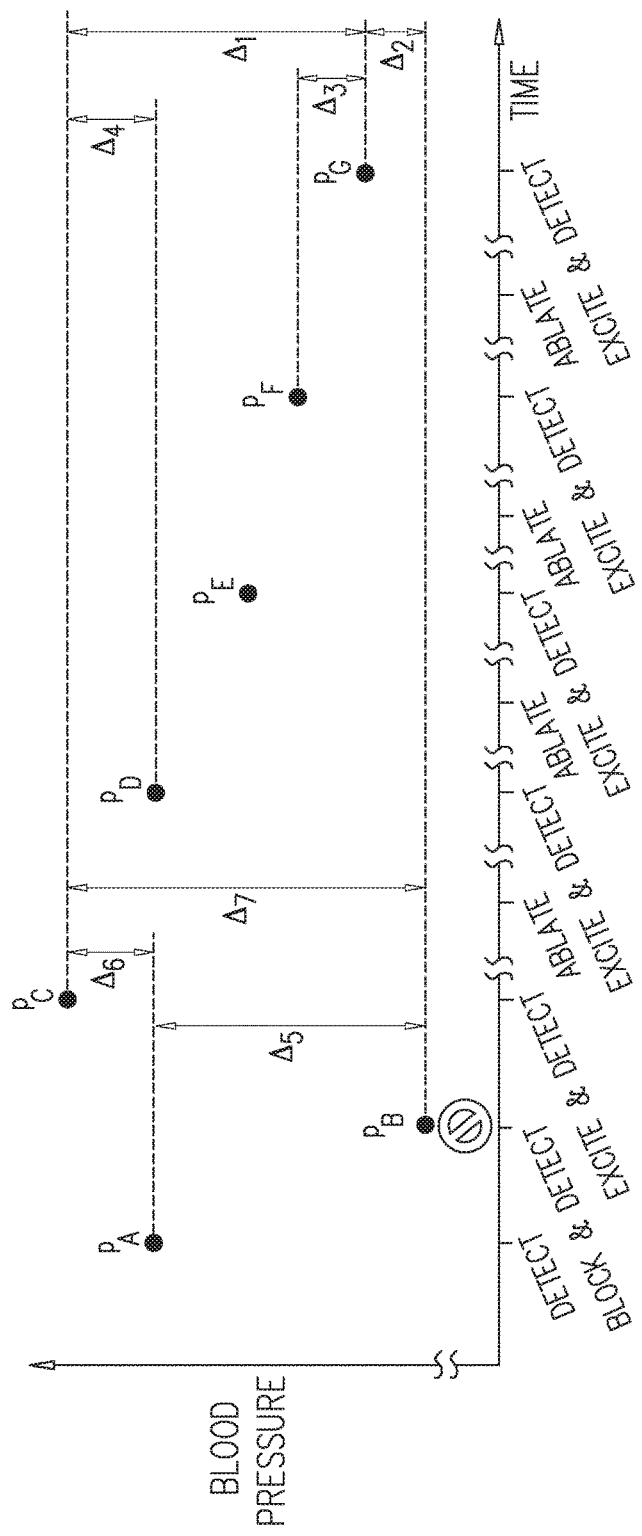

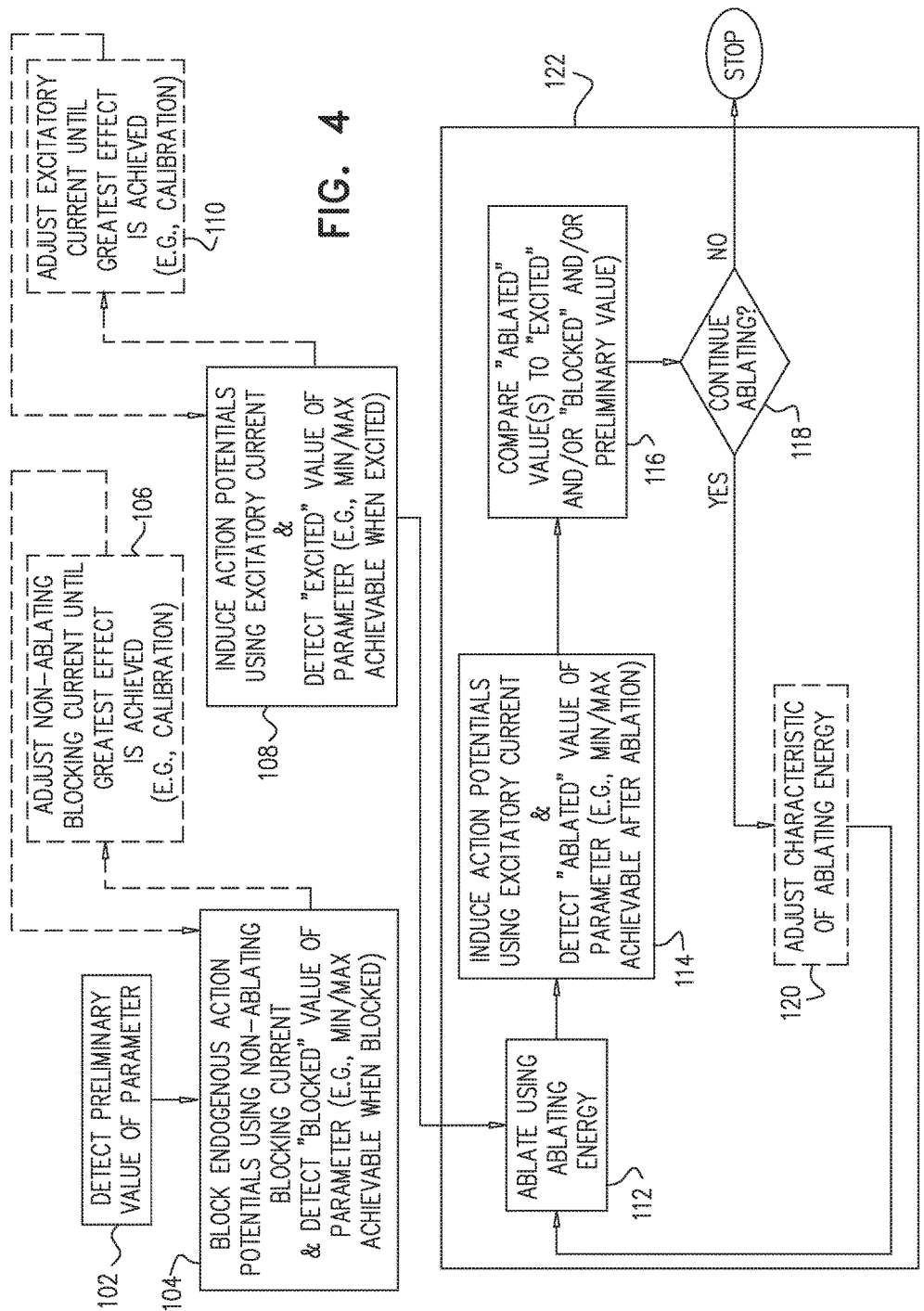

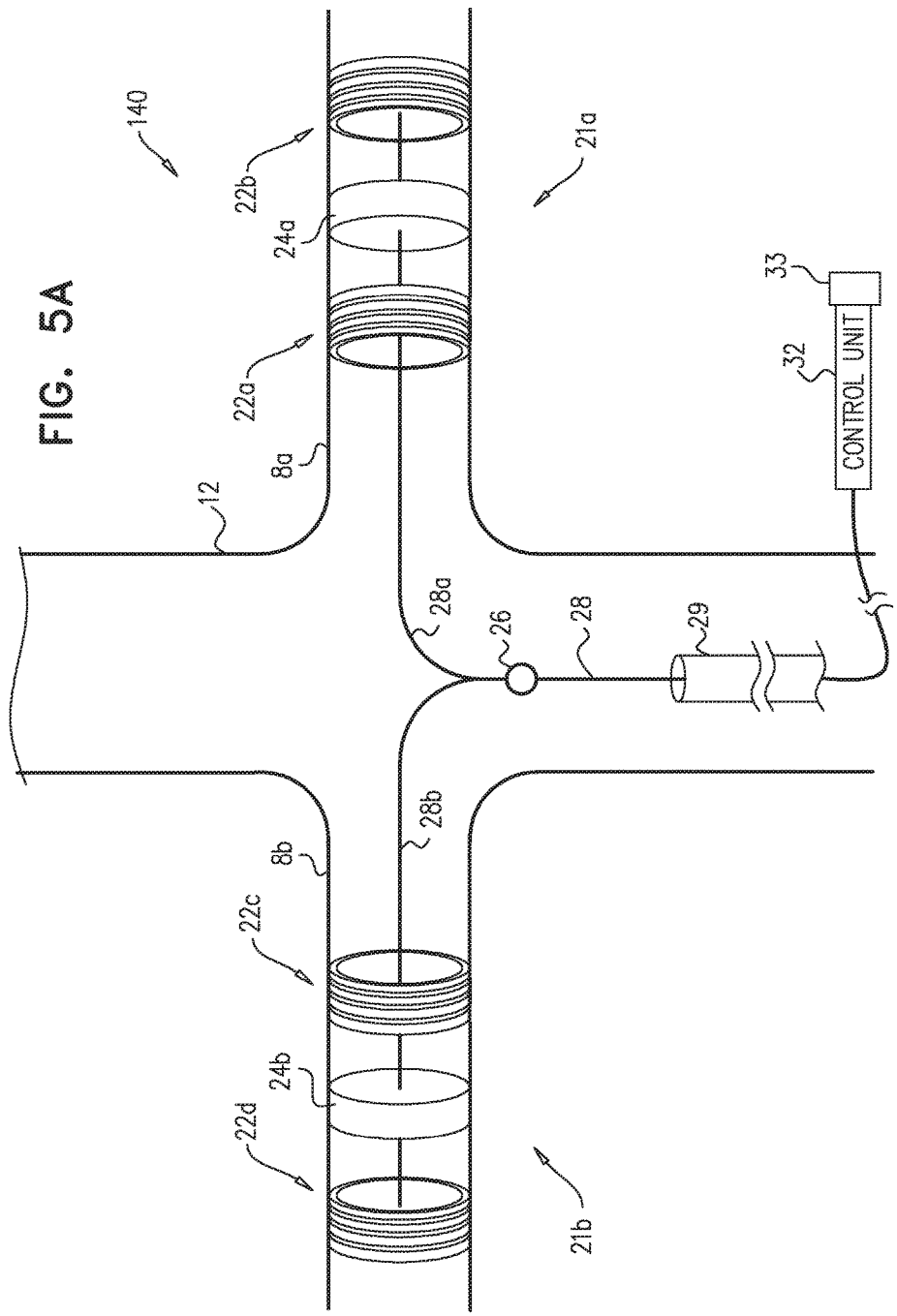

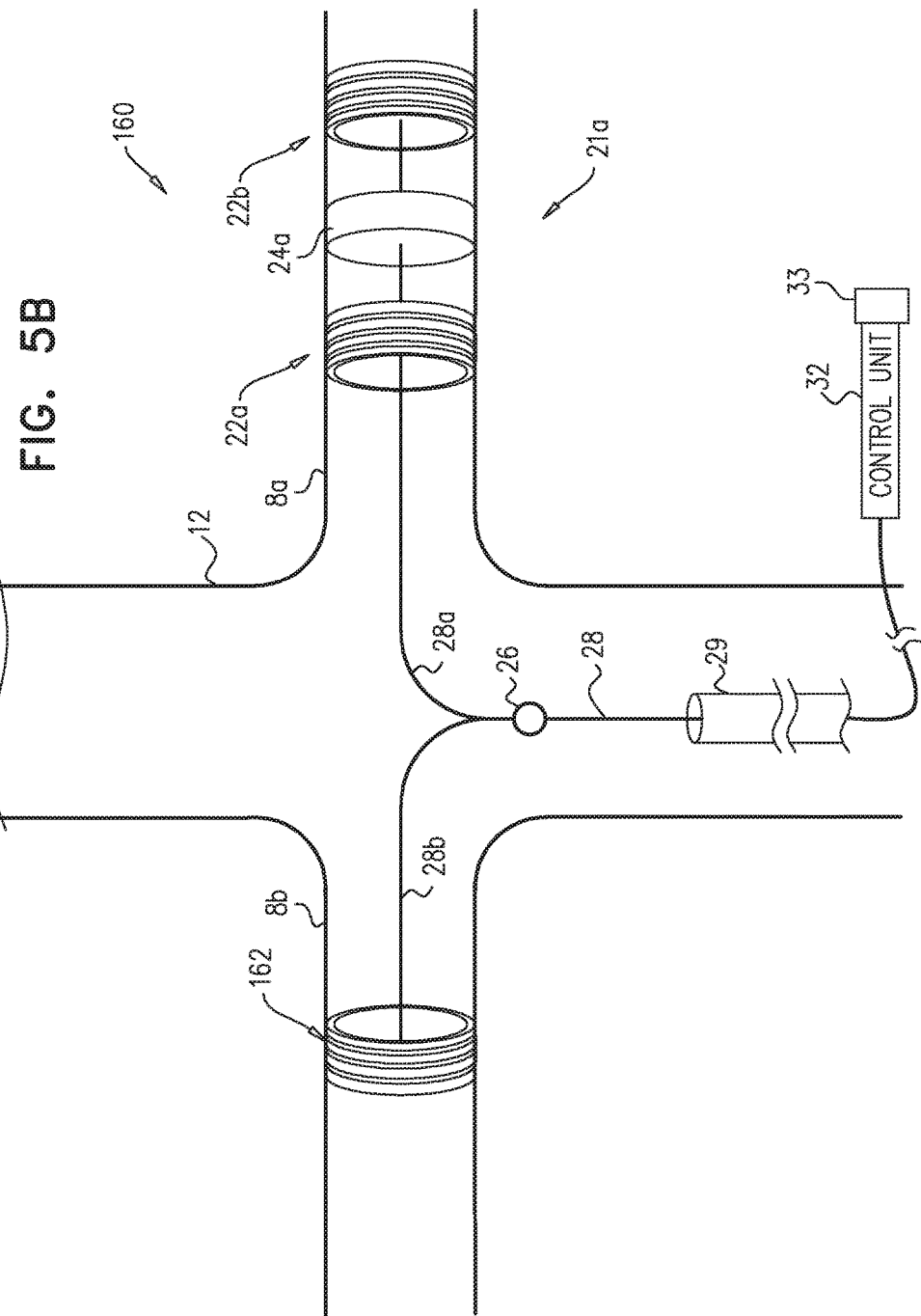

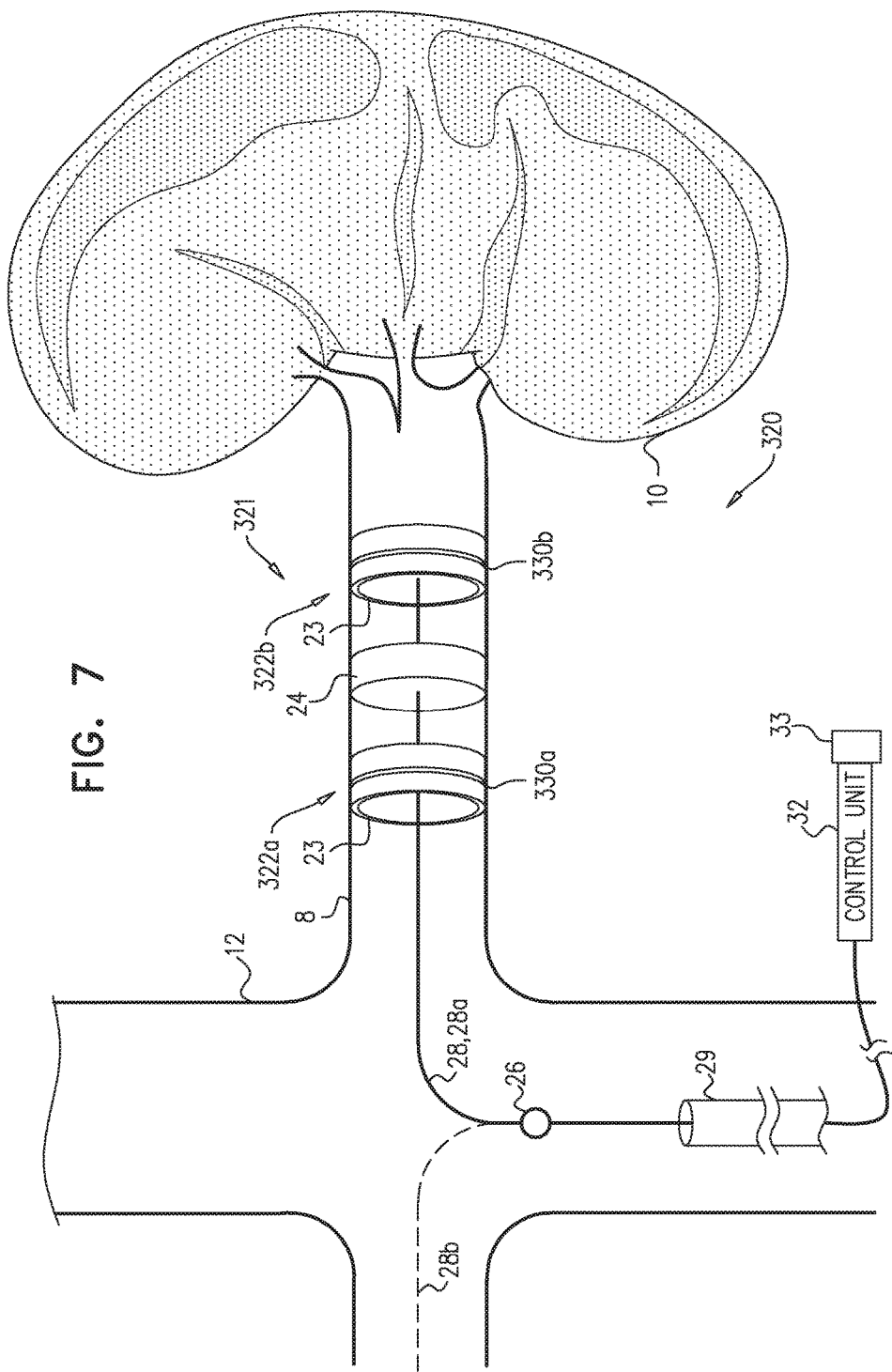

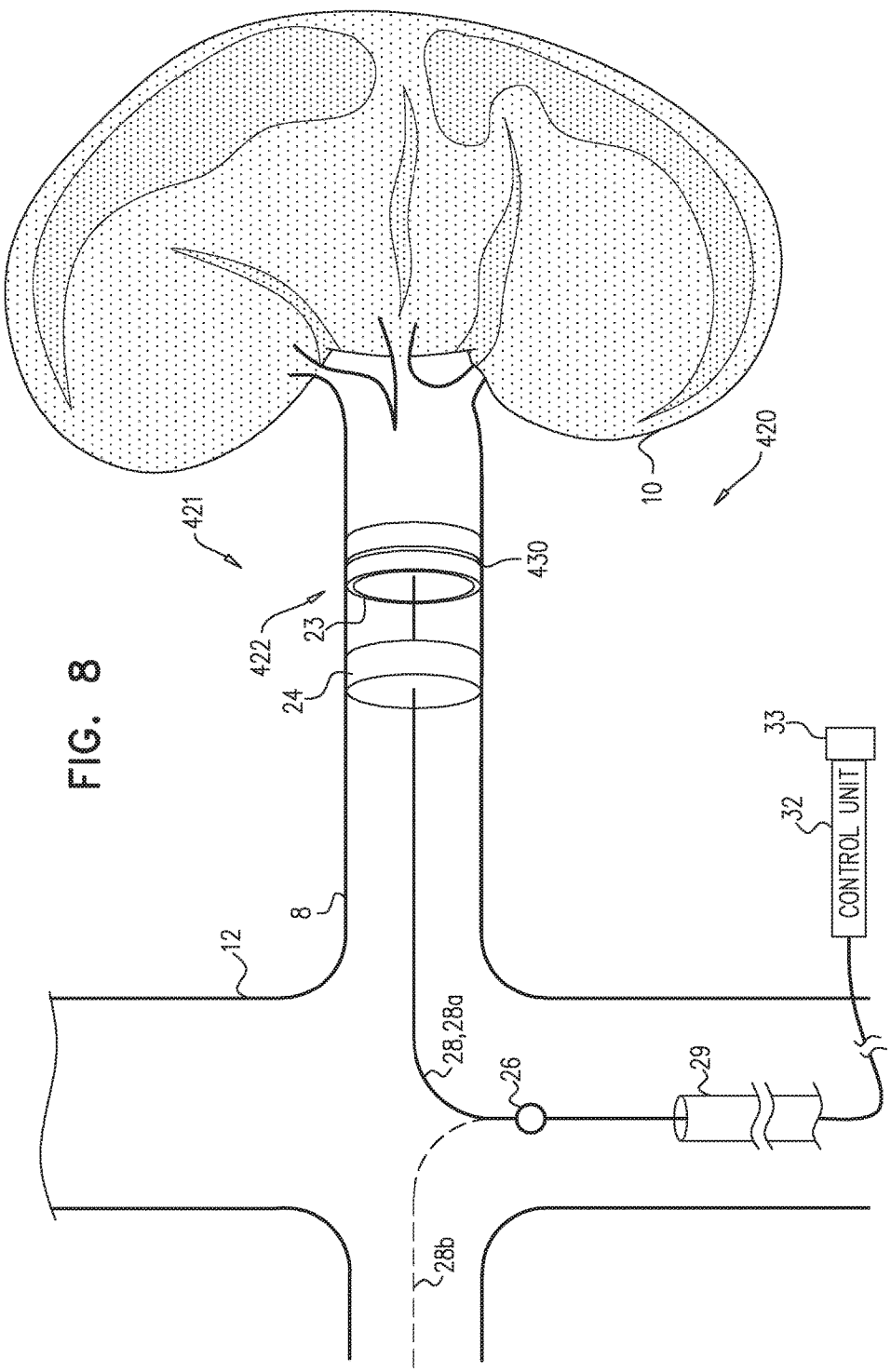

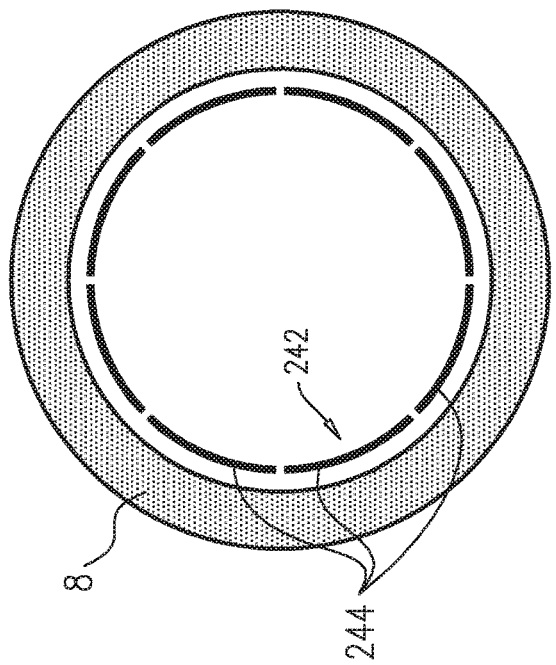
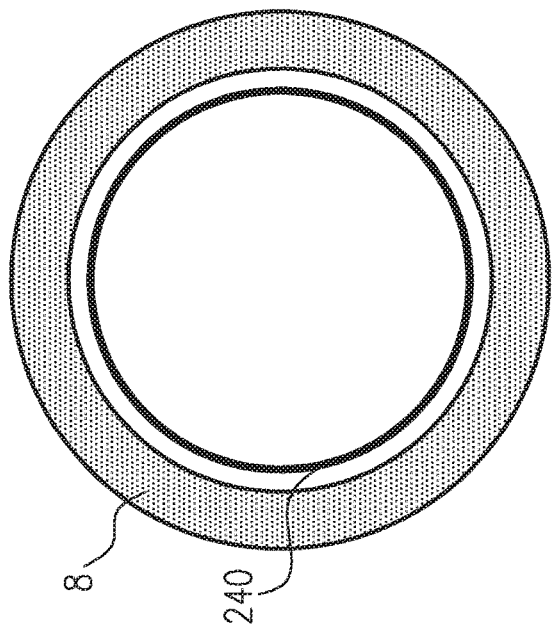

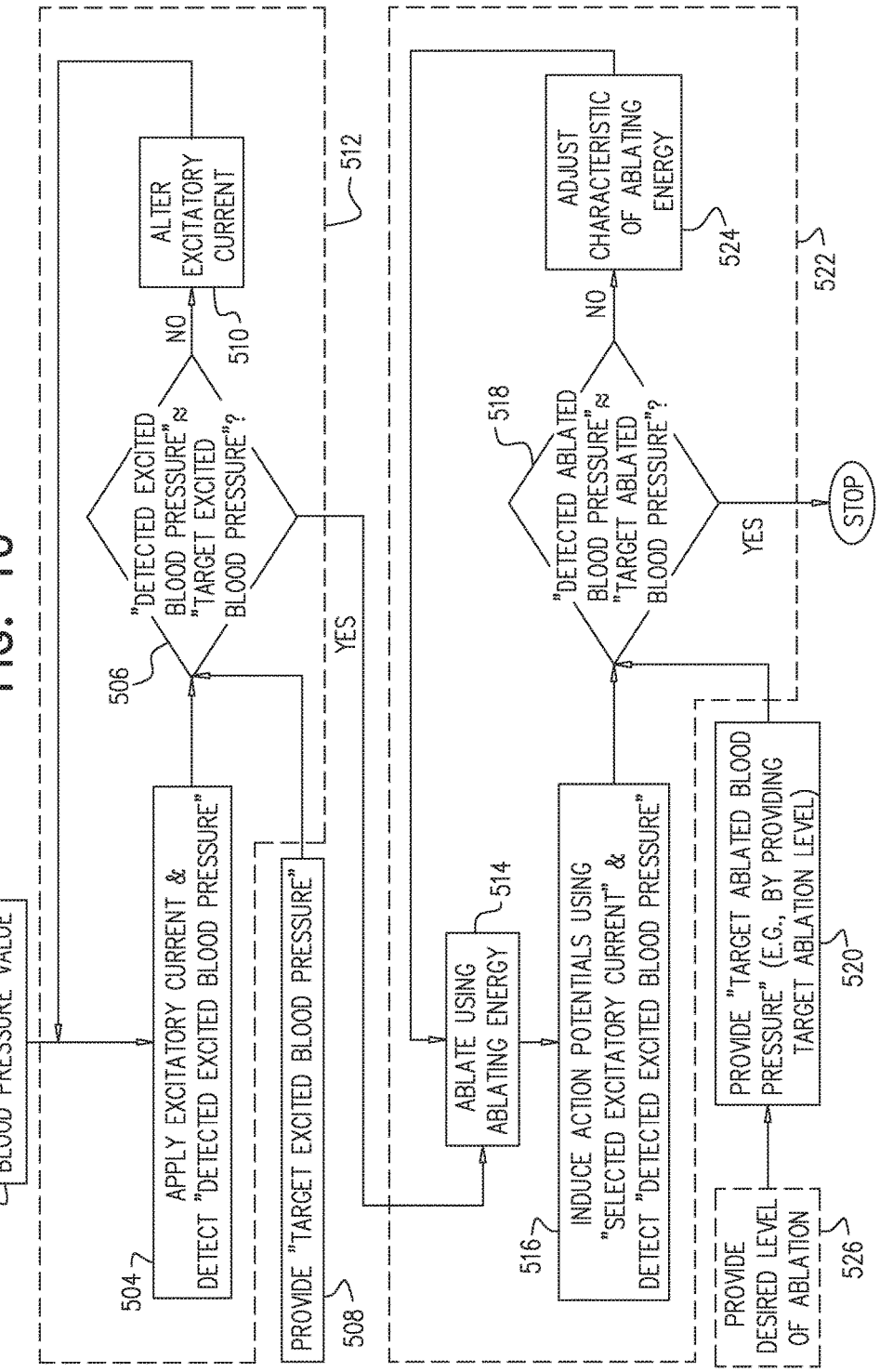

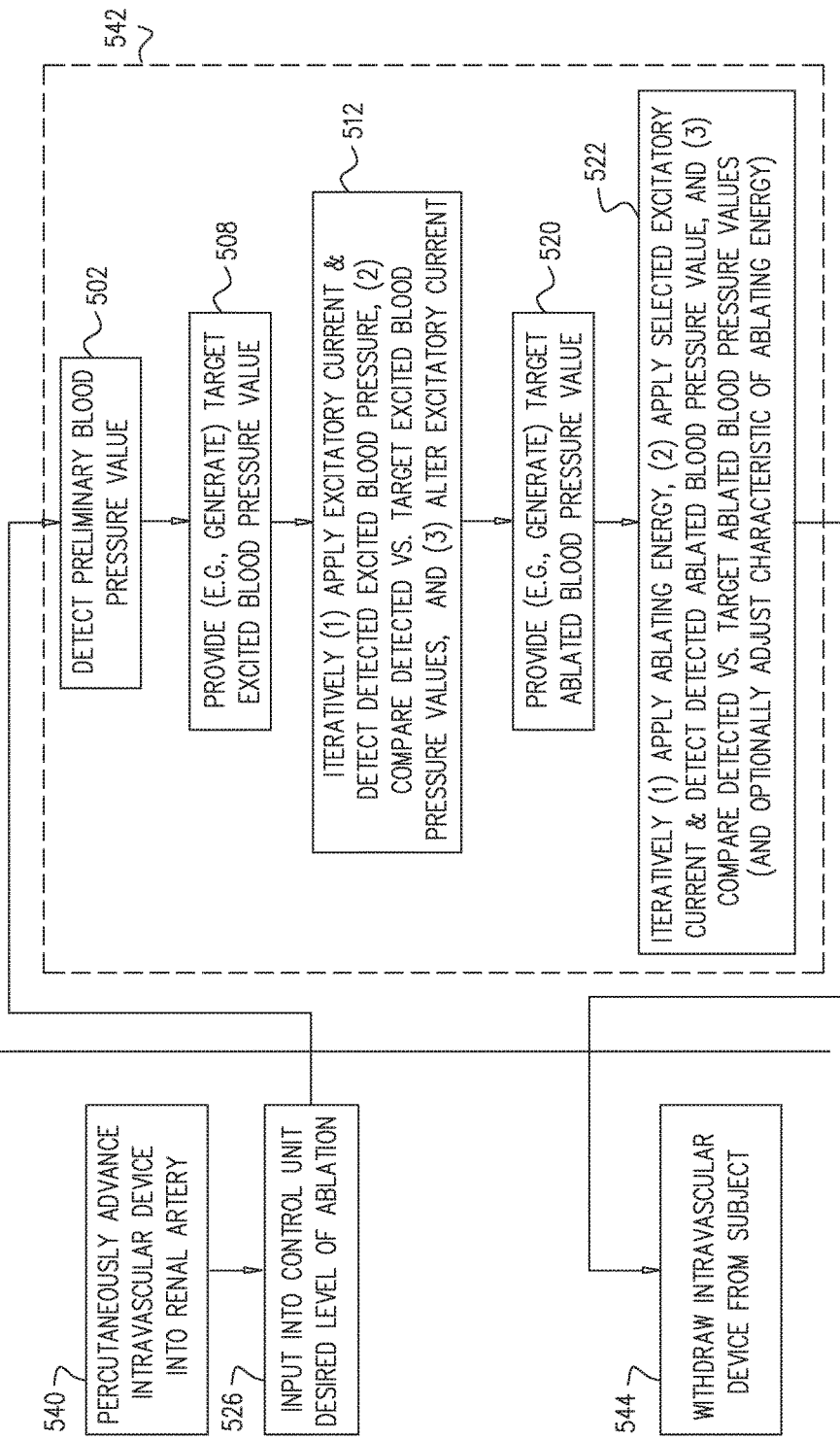

CONTROLLED TISSUE ABLATION

CROSS-REFERENCES TO RELATED APPLICATIONS

The present application is the US National Phase application of PCT application IL/2013/050903 to Gross, filed Nov. 3, 2013, entitled "Controlled Tissue Ablation," which published as WO 2014/068577, and which:

(1) is a Continuation-In-Part of U.S. patent application Ser. No. 13/771,853 to Gross, filed Feb. 20, 2013, titled "Controlled renal artery ablation", which published as US 2014/0128865, and which claims priority from U.S. Provisional Patent Application 61/722,293 to Gross, filed Nov. 5, 2012, titled "Controlled renal artery ablation"; and (2) claims priority from: U.S. Provisional Patent Application 61/811,880 to Gross, filed Apr. 15, 2013, titled "Controlled renal artery ablation"; U.S. Provisional Patent Application 61/841,485 to Gross, filed Jul. 1, 2013, titled "Controlled renal artery ablation"; and U.S. Provisional Patent Application 61/862,561 to Gross, filed Aug. 6, 2013, titled "Controlled tissue ablation"

All of the above applications are incorporated herein by reference.

FIELD OF THE INVENTION

Applications of the present invention relate generally to ablation of tissue. Some applications of the present invention relate more specifically to ablation of tissue of the renal artery.

BACKGROUND

Hypertension is a prevalent condition in the general population, particularly in older individuals. Sympathetic nervous pathways, such as those involving the renal nerve, are known to play a role in regulating blood pressure. Ablation of renal nerve tissue from the renal artery is a known technique for treating hypertension.

SUMMARY OF THE INVENTION

Some applications of the invention comprise detecting one or more values indicative of a parameter of a subject while blocking endogenous action potentials and/or initiating induced action potentials in a nerve of the subject. Based on these one or more values, the potential benefit of a first and/or a successive application of ablative energy to the nerve may be predicted. For some applications of the invention, a control unit controls the blocking, initiating, and ablating, and automatically applies (or automatically does not apply) the first and/or successive application of ablative energy.

There is therefore provided, in accordance with an application of the present invention, an inventive concept including:

1. Apparatus for use with a renal nerve of a renal artery of a subject, the renal nerve innervating an ipsilateral kidney of the subject, the apparatus comprising:

a transvascular catheter, having a distal portion that is configured to be transluminally advanced to the renal artery and comprises:

an electrode unit, configured to apply an excitatory current to a first portion of the renal nerve;

an ablation unit, disposed proximally from the electrode unit, and configured to apply ablation energy to a second portion of the renal nerve that is further from the kidney than is the first portion of the renal nerve; and a control unit, configured:

to receive a preliminary blood pressure value of the subject, to receive a target excited blood pressure value, to iteratively:

(a) drive the electrode unit to apply an excitatory current to the first portion of the renal nerve, (b) receive a detected excited blood pressure value, indicative of a blood pressure of the subject after a start of the application of the excitatory current, and (c) alter a value of at least one property of the excitatory current, until the detected excited blood pressure value crosses a first threshold defined at least in part based on the target excited blood pressure value, and subsequently, to iteratively:

(d) drive the ablation unit to apply ablating energy to the second portion of the renal nerve, (e) subsequently, drive the electrode unit to apply, to the first portion of the renal nerve, a selected excitatory current a characteristic of which is at least part based on the value of the at least one property at which the detected excited blood pressure value crossed the first threshold, and (f) receive a detected ablated blood pressure value, indicative of a blood pressure of the subject after a start of the application of the selected excitatory current, until the detected ablated blood pressure value crosses a second threshold defined at least in part based on a target ablated blood pressure value that is generated at least in part based on the preliminary blood pressure value and at least in part based on at least one excited blood pressure value selected from the group consisting of (i) the target excited blood pressure value and (ii) the detected excited blood pressure value.

2. The apparatus according to inventive concept 1, wherein the ablation unit comprises a radio-frequency ablation unit, and is configured to apply the ablating energy by applying a radio-frequency current having a frequency of between 5 kHz and 1 GHz.

3. The apparatus according to inventive concept 1, wherein the control unit is configured such that, after the first iteration of steps d, e and f, the control unit drives the ablation unit to apply the ablating energy by driving the ablation unit to apply ablating energy that is different in at least one characteristic thereof compared to the ablating energy applied in the previous iteration of steps d, e and f.

4. The apparatus according to inventive concept 1, wherein the control unit is configured to generate the target excited blood pressure value at least in part responsively to the preliminary blood pressure value.

5. The apparatus according to inventive concept 1, wherein the control unit comprises a user interface, and is configured to receive the target excited blood pressure value via the user interface.

6. The apparatus according to any one of inventive concepts 1-5, wherein the electrode unit comprises a plurality of sub-electrodes configured to be arranged in a broken arc that traces an inner wall of the renal artery.

7. The apparatus according to inventive concept 6, wherein the control unit is configured to drive the plurality of sub-electrodes to simultaneously apply the excitatory current.

8. The apparatus according to inventive concept 7, wherein each of the plurality of sub-electrodes is independently addressable by the control unit.

9. The apparatus according to inventive concept 7, wherein the control unit is configured to balance the excitatory current across the plurality of sub-electrodes.

10. The apparatus according to any one of inventive concepts 1-5, wherein:
the renal nerve of the renal artery includes a renal nerve of a first renal artery of the subject,
the distal portion of the transvascular catheter comprises a first distal portion of the transvascular catheter, configured to be transluminally advanced to the first renal artery, and
the transvascular catheter is bifurcated so as to have the first distal portion and a second distal portion, the second distal portion being configured to be transluminally advanced to the second renal artery.

11. The apparatus according to inventive concept 10, wherein the second distal portion is separate from but identical to the first distal portion.

12. The apparatus according to any one of inventive concepts 1-5, further comprising a pressure sensor, wherein the control unit is configured to receive the preliminary blood pressure value, the detected excited blood pressure value, and the detected ablated blood pressure value, from the pressure sensor.

13. The apparatus according to inventive concept 12, wherein the transvascular catheter comprises the pressure sensor, and the pressure sensor is disposed proximally from the distal portion.

14. The apparatus according to inventive concept 13, wherein the pressure sensor is disposed with respect to the distal portion such that such that when the distal portion is disposed in the renal artery of the subject, the pressure sensor is disposed in the aorta of the subject.

15. The apparatus according to inventive concept 13, wherein the pressure sensor is disposed more than 2 cm proximally from the distal portion.

16. The apparatus according to any one of inventive concepts 1-5, wherein the control unit is configured to generate the target ablated blood pressure value at least in part responsively to (1) the preliminary blood pressure value and (2) at least one excited blood pressure value selected from the group consisting of: (i) the target excited blood pressure value and (ii) the detected excited blood pressure value.

17. The apparatus according to inventive concept 16, wherein the control unit is configured to generate the target excited blood pressure value at least in part responsively to a value indicative of a target degree of ablation of the renal nerve.

18. The apparatus according to inventive concept 17, wherein the control unit comprises an interface, and is configured to receive the value indicative of the target degree of ablation via the interface.

There is further provided, in accordance with an application of the present invention, an inventive concept including:

19. Apparatus for facilitating ablation of nerve tissue of a blood vessel of a subject, the apparatus comprising:
a transvascular catheter comprising:
an electrode unit, disposed at a distal portion of the transvascular catheter;
an ablation unit, disposed proximally from the electrode unit; and
a blood pressure sensor, disposed proximally from the ablation unit; and a control unit, configured:
to drive the electrode unit to apply a non-ablative electrical current to a first portion of the nerve tissue,
to drive the ablation unit to apply ablative energy to a second portion of the nerve tissue, and
to receive, from the blood pressure sensor, at least one value indicative of a blood pressure of the subject.

20. The apparatus according to inventive concept 19, wherein the ablation unit comprises a radio-frequency ablation unit, and the control unit is configured to drive the ablation unit to apply the ablative energy by driving the ablation unit to apply a radio-frequency current having a frequency of between 5 kHz and 1 GHz.

21. The apparatus according to inventive concept 19, wherein:
the distal portion of the transvascular catheter comprises a first distal portion of the transvascular catheter,
the electrode unit comprises a first electrode unit,
the ablation unit comprises a second electrode unit,
the transvascular catheter is bifurcated so as to have the first distal portion and a second distal portion, and
the transvascular catheter further comprises:
a second electrode unit, disposed at the second distal portion of the catheter; and
a second ablation unit, disposed proximally from the second electrode unit.

22. The apparatus according to inventive concept 19, wherein the control unit is configured to apply the ablative energy in response to at least the at least one value.

23. The apparatus according to inventive concept 19, wherein the distal portion of the transvascular catheter is configured to be advanced into the blood vessel of the subject, and the transvascular catheter is configured such that, when the electrode unit is disposed within the blood vessel of the subject, the blood pressure sensor is disposed in another blood vessel of the subject.

24. The apparatus according to inventive concept 19, wherein the blood pressure sensor is disposed more than 2 cm proximally from the ablation unit.

25. The apparatus according to any one of inventive concepts 19-24, wherein the electrode unit comprises a plurality of sub-electrodes configured to be arranged in a broken arc that traces an inner wall of the blood vessel.

26. The apparatus according to inventive concept 25, wherein the control unit is configured to drive the plurality of sub-electrodes to simultaneously apply the non-ablative electrical current.

27. The apparatus according to inventive concept 26, wherein each of the plurality of sub-electrodes is independently addressable by the control unit.

28. The apparatus according to inventive concept 26, wherein the control unit is configured to balance the non-ablative electrical current across the plurality of sub-electrodes.

There is further provided, in accordance with an application of the present invention, an inventive concept including:

29. Apparatus for facilitating ablation of nerve tissue of a subject, the nerve tissue conducting endogenous action potentials to an anatomical structure of the subject, the structure being capable of altering a parameter of the subject at least in part responsively to the endogenous action potentials, the apparatus comprising:
a sensor, configured to detect a factor indicative of the parameter of the subject;

an ablation unit, configured to be percutaneously advanced to a site adjacent to a first portion of the nerve tissue of the subject;
at least one electrode unit, configured to be percutaneously advanced to a site adjacent to a second portion of the nerve tissue of the subject; and
a control unit, configured to:
  drive the electrode unit to initiate induced action potentials in the second portion of the nerve tissue of the subject by applying an excitatory current to the second portion of the nerve tissue, the action potentials inducing the structure to alter the parameter of the subject,
  receive, from the sensor, information indicative of the factor, and
  at least in part responsively to the information, drive the ablation unit to apply ablative energy to the first portion of the tissue.

30. The apparatus according to inventive concept 29, wherein the ablation unit comprises a radio-frequency ablation unit, and the control unit is configured to drive the ablation unit to apply the ablative energy by driving the ablation unit to apply a radio-frequency current having a frequency of between 5 kHz and 1 GHz.

31. The apparatus according to inventive concept 29, wherein the electrode unit is configured to be positioned with respect to the ablation unit such that the induced action potentials propagate toward the first portion of the nerve of the subject.

32. The apparatus according to inventive concept 29, wherein:
  the ablation unit comprises a first ablation unit, and the at least one electrode unit comprises a respective first at least one electrode unit, and
  the apparatus further comprises a second ablation unit and a second respective at least one electrode unit.

33. The apparatus according to any one of inventive concepts 29-32, wherein the electrode unit comprises a plurality of sub-electrodes configured to be arranged in a broken arc.

34. The apparatus according to inventive concept 33, wherein the control unit is configured to drive the plurality of sub-electrodes to simultaneously apply the excitatory current.

35. The apparatus according to inventive concept 33, wherein each of the plurality of sub-electrodes is independently addressable by the control unit.

36. The apparatus according to inventive concept 33, wherein the control unit is configured to balance the excitatory current applied by each of the plurality of sub-electrodes.

37. The apparatus according to any one of inventive concepts 29-32, wherein the control unit is further configured to drive the electrode unit to apply a non-ablative blocking current to the second portion of the nerve.

There is further provided, in accordance with an application of the present invention, an inventive concept including:

38. Apparatus for facilitating ablation of nerve tissue of a blood vessel of a subject, the apparatus comprising an intravascular device, the intravascular device comprising:
  a first electrode unit, disposed at a first longitudinal site of the intravascular device, and configured to initiate action potentials in a first portion of the nerve tissue that is adjacent to the first electrode unit;
  a second electrode unit, disposed at a second longitudinal site of the intravascular device, and configured to block action potentials in a second portion of the nerve tissue that is adjacent to the second electrode unit; and
  an ablation unit, disposed at a third longitudinal site of the intravascular device that is between the first longitudinal site and the second longitudinal site, the ablation unit being configured to ablate a third portion of the nerve tissue that is adjacent to the ablation unit and between the first portion of the nerve tissue and the second portion of the nerve tissue.

39. The apparatus according to inventive concept 38, wherein the first electrode unit comprises a plurality of sub-electrodes configured to be arranged in a broken arc that traces an inner wall of the blood vessel.

40. The apparatus according to any one of inventive concepts 38-39, wherein the blood vessel includes a first blood vessel, the intravascular device comprises a first intravascular device configured to be placed within the first blood vessel, and the apparatus further comprises a second intravascular device, configured to be placed within a second blood vessel of the subject.

41. The apparatus according to inventive concept 40, wherein the second intravascular device is separate from but identical to the first intravascular device.

42. The apparatus according to any one of inventive concepts 38-39, wherein the first electrode unit is configured to initiate unidirectional action potentials in the first portion of the nerve tissue, such that the unidirectional action potentials propagate toward the second portion of the nerve tissue.

43. The apparatus according to inventive concept 42, wherein the unidirectional action potentials comprise first unidirectional action potentials, and the second electrode unit is further configured to initiate second unidirectional action potentials in the second portion of the nerve tissue, such that the second unidirectional action potentials propagate toward the first portion of the nerve tissue.

There is further provided, in accordance with an application of the present invention, an inventive concept including:

44. Apparatus for facilitating ablation of nerve tissue of a blood vessel of a subject, the apparatus comprising:
  an intravascular device, configured to be placed within the blood vessel, and comprising a plurality of electrodes disposed at respective longitudinal sites of the intravascular device; and
  a control unit, configured to:
    during at least a first period, inhibit action potentials in the nerve tissue from propagating past the intravascular device by driving at least one of the electrodes to apply a non-ablative blocking current to the nerve tissue,
    during a second period, initiate action potentials in the nerve tissue by driving at least one of the electrodes to apply an excitatory current to the nerve tissue,
    during a third period that is subsequent to at least one of the periods selected from the group consisting of: the first period and the second period, drive the intravascular device to apply ablative energy to a portion of the nerve tissue.

45. The apparatus according to inventive concept 44, wherein the control unit is configured to inhibit action potentials in the nerve tissue during at least part of the third period.

46. The apparatus according to any one of inventive concepts 44-45, wherein the blood vessel includes a first blood vessel, the intravascular device comprises a first intravascular device configured to be placed within the first blood vessel, and the apparatus further comprises a second intravascular device, configured to be placed within a second blood vessel of the subject.

47. The apparatus according to inventive concept 46, wherein the second intravascular device is separate from but identical to the first intravascular device.

48. The apparatus according to any one of inventive concepts 44-45, wherein the intravascular device comprises an ablation unit, and wherein the control unit is configured to drive the intravascular device to apply the ablative energy by driving the ablation unit to apply the ablative energy.

49. The apparatus according to inventive concept 48, wherein the plurality of electrodes comprises at least (1) a first electrode disposed at a first longitudinal site of the intravascular device that is on a first side of the ablation unit, and (2) a second electrode disposed at a second longitudinal site of the intravascular device that is on an opposite side of the ablation unit to the first longitudinal site.

50. The apparatus according to inventive concept 49, wherein the control unit is configured:
    to drive the at least one of the electrodes to apply the blocking current during the first period by driving the first electrode to apply the blocking current to the nerve tissue, and
    to drive the at least one of the electrodes to apply the excitatory current during the second period by driving the second electrode to apply the excitatory current to the nerve tissue.

51. The apparatus according to inventive concept 50, wherein the plurality of electrodes comprises a third electrode, disposed at a third longitudinal site of the intravascular device that is on the first side of the ablation unit, and wherein the control unit is configured to drive the blocking current between the first electrode and the third electrode.

52. The apparatus according to inventive concept 48, wherein the intravascular device further comprises at least a first electrode unit:
    comprising at least one of the electrodes of the plurality of electrodes,
    configured to initiate unidirectional action potentials in the nerve tissue, and
    oriented with respect to the ablation unit such that the unidirectional action potentials propagate toward the portion of the nerve tissue, the control unit being configured to initiate action potentials in the nerve tissue by driving the first electrode unit to initiate the unidirectional action potentials in the nerve tissue.

53. The apparatus according to inventive concept 48, wherein:
    the at least first electrode unit comprises at least a second electrode unit,
    the first electrode unit is disposed at a first longitudinal site of the intravascular device that is on a first side of the ablation unit,
    the second electrode unit is disposed at a second longitudinal site of the intravascular device that is on an opposite side of the ablation unit to the first longitudinal site, and is oriented inversely to the first electrode unit.

54. The apparatus according to inventive concept 48, wherein the ablation unit comprises an electrode of the plurality of electrodes, and the control unit is configured to drive the ablation unit to apply the ablative energy by driving the electrode of the ablation unit to apply ablative radio-frequency current.

55. The apparatus according to inventive concept 48, wherein the ablation unit comprises an ultrasound transducer, and the control unit is configured to drive the ablation unit to apply the ablative energy by driving the ultrasound transducer to apply ablative ultrasound energy.

56. The apparatus according to any one of inventive concepts 44-45, wherein the control unit is configured:
    to receive (1) a first value of the subject, the first value being indicative of a blood pressure of the subject after a start of the application of the blocking current, and (2) a second value of the subject, the second value being indicative of a blood pressure of the subject after a start of the application of the excitatory current, and
    to drive the intravascular device to apply the ablative energy at least in part responsively to a difference between the first value and the second value.

57. The apparatus according to inventive concept 56, wherein:
    the application of the excitatory current comprises a first application of the excitatory current,
    the application of ablative energy comprises a first application of ablative energy, and
    the control unit is configured:
        during a fourth period that is subsequent to the third period, to initiate action potentials in the nerve tissue by driving at least one of the electrodes to apply a second application of the excitatory current to the nerve tissue,
        to receive a third value of the subject, the third value being indicative of a blood pressure of the subject after a start of the second application of the excitatory current, and
        at least in part responsively to a difference between the second value and the third value, to drive the intravascular device to apply a second application of the ablative energy to the portion of the nerve tissue.

58. The apparatus according to inventive concept 56, further comprising a sensor, configured to be intravascularly placed within the subject, wherein the control unit is configured to receive the first value and the second value from the sensor.

There is further provided, in accordance with an application of the present invention, an inventive concept including:

59. Apparatus for facilitating ablation of nerve tissue of a subject, the apparatus comprising:
    an ablation unit, configured to be percutaneously advanced to a site adjacent to a first portion of the nerve tissue of the subject;
    at least one electrode unit, coupled to the ablation unit, and configured to be percutaneously advanced to a site adjacent to a second portion of the nerve tissue of the subject, and to initiate unidirectional action potentials in the nerve tissue, such that the unidirectional action potentials propagate toward the first portion of the nerve tissue; and
    a control unit, configured:
        to drive the ablation unit to ablate, at least in part, the first portion of the nerve tissue of the subject, and
        to drive the at least one electrode unit to initiate the unidirectional action potentials by applying an excitatory current to the second portion of the nerve tissue.

60. The apparatus according to inventive concept 59, wherein the at least one electrode unit comprises a first electrode unit and a second electrode unit, the first electrode unit being coupled to the ablation unit on a first side of the ablation unit, and the second electrode unit being coupled to the ablation unit on a second side of the ablation unit, each electrode unit being configured to initiate unidirectional action potentials in the nerve tissue, such that the action potentials propagate toward the first portion of the nerve tissue.

61. The apparatus according to inventive concept 59, wherein the ablation unit comprises a radio-frequency ablation unit, and wherein the control unit is configured to drive the radio-frequency ablation unit to ablate the first portion of the nerve tissue by applying an ablative radio-frequency current to the first portion of the nerve tissue.

62. The apparatus according to inventive concept 59, wherein the ablation unit comprises an ultrasound ablation unit, and wherein the control unit is configured to drive the ultrasound ablation unit to ablate the first portion of the nerve tissue by applying ablative ultrasound energy to the first portion of the nerve tissue.

63. The apparatus according to inventive concept 59, wherein the electrode unit is configured to apply a non-ablative blocking current to the second portion of the nerve tissue of the subject, the non-ablative blocking current being configured to reversibly block endogenous action potentials from propagating through the second portion of the nerve tissue, and wherein the control unit is configured to drive the at least one electrode unit to apply the non-ablative blocking current.

64. The apparatus according to any one of inventive concepts 59-63, wherein the site includes a blood vessel, the nerve tissue includes nerve tissue of the blood vessel, and the at least one electrode unit comprises a plurality of sub-electrodes configured to be arranged in a broken arc that traces an inner wall of the blood vessel.

65. The apparatus according to inventive concept 64, wherein the control unit is configured to drive the plurality of sub-electrodes to simultaneously apply the excitatory current.

66. The apparatus according to inventive concept 65, wherein each of the plurality of sub-electrodes is independently addressable by the control unit.

67. The apparatus according to inventive concept 65, wherein the control unit is configured to balance the excitatory current across the plurality of sub-electrodes.

68. The apparatus according to any one of inventive concepts 59-63, wherein the nerve tissue includes nerve tissue of a blood vessel of the subject, and wherein at least the ablation unit is configured to be transluminally delivered to the blood vessel of the subject.

69. The apparatus according to inventive concept 68, wherein the electrode unit is configured to be transluminally delivered to the blood vessel of the subject.

70. The apparatus according to inventive concept 68, wherein the blood vessel includes a renal artery of the subject, and wherein at least the ablation unit is configured to be transluminally delivered to the renal artery of the subject.

71. The apparatus according to any one of inventive concepts 59-63, further comprising a longitudinal member, having a distal portion that is configured to be percutaneously advanced toward the nerve tissue of the subject, and wherein the ablation unit and the at least one electrode unit are coupled to the longitudinal member.

72. The apparatus according to inventive concept 71, wherein:
the ablation unit comprises a first ablation unit, and the at least one electrode unit comprises a respective first at least one electrode unit,
the apparatus further comprises a second ablation unit and a second respective at least one electrode unit, and
the distal portion of the longitudinal member is bifurcated so as to have (i) a first distal portion that is coupled to the first ablation unit and the first at least one electrode unit, and (ii) a second distal portion that is coupled to the second ablation unit and the second at least one electrode unit, each of the distal portions being configured to be transluminally advanced into a respective renal artery of the subject.

73. The apparatus according to any one of inventive concepts 59-63, further comprising a sensor, configured to detect a physiological response of the subject to the unidirectional action potentials initiated by the electrode unit.

74. The apparatus according to inventive concept 73, further comprising a longitudinal member, configured to be percutaneously advanced toward the nerve tissue of the subject, and wherein the ablation unit, the electrode unit, and the sensor are coupled to the longitudinal member.

75. The apparatus according to inventive concept 73, wherein the sensor is configured to be disposed in an aorta of the subject.

76. The apparatus according to inventive concept 73, wherein the sensor comprises a blood pressure sensor.

77. The apparatus according to inventive concept 73, wherein the control unit is configured to receive information indicative of the detected physiological response, and to drive the ablation unit at least in part responsively to the information indicative of the detected physiological response.

78. The apparatus according to inventive concept 77, wherein the control unit is configured:
to drive, during a first period, the at least one electrode unit to apply a non-ablative blocking current to the second portion of the nerve tissue of the subject, the blocking current being configured to temporarily block endogenous action potentials from propagating through the second portion of the nerve tissue,
to receive a first value of a factor indicative of the response, the first value being detected after a start of the application of the non-ablative blocking current, and
to drive the ablation unit at least in part responsively to the received first value.

79. The apparatus according to inventive concept 78, wherein the control unit is configured:
to drive, during a second period, the at least one electrode unit to apply the excitatory current,
to receive a second value of the factor, the second value being detected after a start of the application of the excitatory current, and
to drive the ablation unit at least in part responsively to the received second value.

80. The apparatus according to inventive concept 78, wherein the sensor is configured to detect the first value of the factor after the start of the application of the non-ablative blocking current, and to provide the first value of the factor to the control unit.

There is further provided, in accordance with an application of the present invention, an inventive concept including:

81. Apparatus for facilitating ablation of nerve tissue of a blood vessel of a subject, the apparatus comprising:
an intravascular device, configured to be placed within the blood vessel, and comprising a plurality of electrodes disposed at respective longitudinal sites of the intravascular device;
a sensor, configured to be intravascularly placed within the subject; and
a control unit, configured to:
drive at least one of the electrodes to apply a non-ablative electrical current to the nerve tissue,
receive from the sensor a first value of the subject, the first value being indicative of a blood pressure of the subject after a start of the application of the non-ablative electrical current,
subsequently drive at least one of the electrodes to apply a first application of ablative energy to the nerve tissue,
receive from the sensor a second value of the subject, the second value being indicative of the blood pressure of the subject after the first application of the ablative energy, and
at least in part responsively to a difference between the first value and the second value, drive at least one of the electrodes to apply a second application of the ablative energy to the nerve tissue.

82. The apparatus according to inventive concept 81, wherein the control unit is configured to drive the at least one of the electrodes to apply the first application of ablative energy by driving the at least one of the electrodes to apply a radio-frequency current having a frequency of between 5 kHz and 1 GHz.

83. The apparatus according to any one of inventive concepts 81-82, wherein at least one of the plurality of electrodes comprises a plurality of sub-electrodes configured to be arranged in a broken arc that traces an inner wall of the blood vessel.

84. The apparatus according to inventive concept 83, wherein the control unit is configured to drive the plurality of sub-electrodes to simultaneously apply the non-ablative electrical current.

85. The apparatus according to inventive concept 84, wherein each of the plurality of sub-electrodes is independently addressable by the control unit.

86. The apparatus according to inventive concept 84, wherein the control unit is configured to balance the non-ablative electrical current across the plurality of sub-electrodes.

87. The apparatus according to any one of inventive concepts 81-82, wherein the blood vessel includes a first blood vessel, the intravascular device comprises a first intravascular device configured to be placed within the first blood vessel, and the apparatus further comprises a second intravascular device, configured to be placed within a second blood vessel of the subject.

88. The apparatus according to inventive concept 87, wherein the second intravascular device is separate from but identical to the first intravascular device.

There is further provided, in accordance with an application of the present invention, an inventive concept including:

89. A method for use with nerve tissue of a subject, the nerve tissue conducting endogenous action potentials to an anatomical structure of the subject, the structure being capable of altering a parameter of the subject at least in part responsively to the endogenous action potentials, the method comprising:
initiating action potentials in a first portion of the nerve tissue by applying an excitatory current to the first portion of the nerve tissue, wherein applying the excitatory current comprises, after a start of the application of the excitatory current, performing a detection of a factor indicative of the parameter of the subject; and
subsequently, applying ablating energy to a second portion of the nerve tissue, at least in part in response to the detection.

90. The method according to inventive concept 89, wherein initiating action potentials in a first portion of the nerve tissue comprises initiating action potentials in a first portion of a postganglionic neuron of the subject, and wherein applying ablating energy to a second portion of the nerve tissue comprises applying ablating energy to a second portion of the postganglionic neuron.

91. The method according to inventive concept 89, wherein the subject suffers from a condition in which the parameter is affected by overactivity of a sympathetic nervous system of the subject, initiating action potentials in the first portion of the nerve tissue comprises initiating action potentials in a first portion of nerve tissue of the sympathetic nervous system, and applying ablating energy to the second portion of the nerve tissue comprises applying ablating energy to a second portion of the nerve tissue of the sympathetic nervous system.

92. The method according to inventive concept 89, wherein the subject suffers from a condition in which the parameter is affected by overactivity of a parasympathetic nervous system of the subject, initiating action potentials in the first portion of the nerve tissue comprises initiating action potentials in a first portion of nerve tissue of the parasympathetic nervous system, and applying ablating energy to the second portion of the nerve tissue comprises applying ablating energy to a second portion of the nerve tissue of the parasympathetic nervous system.

93. The method according to inventive concept 89, wherein performing the detection after the start of the application of the excitatory current comprises performing the detection during the application of the excitatory current.

94. The method according to inventive concept 89, wherein performing the detection after the start of the application of the excitatory current comprises performing the detection after the application of the excitatory current.

95. The method according to inventive concept 89, wherein initiating action potentials comprises initiating unidirectional action potentials in the nerve tissue.

96. The method according to any one of inventive concepts 89-95, further comprising identifying that the subject suffers from premature ejaculation, wherein initiating action potentials comprises initiating action potentials in response to the identifying.

97. The method according to inventive concept 96, wherein:
initiating action potentials in the first portion of the nerve tissue comprises initiating action potentials in a first portion of a dorsal nerve of the subject, and
applying ablating energy to the second portion of the nerve tissue comprises applying ablating energy to a second portion of the dorsal nerve of the subject.

98. The method according to inventive concept 96, wherein:
initiating action potentials in the first portion of the nerve tissue comprises initiating action potentials in a first portion of a pudendal nerve of the subject, and
applying ablating energy to the second portion of the nerve tissue comprises applying ablating energy to a second portion of the pudendal nerve of the subject.

99. The method according to inventive concept 96, wherein:
initiating action potentials in the first portion of the nerve tissue comprises initiating action potentials in a first portion of a sacral nerve of the subject, and
applying ablating energy to the second portion of the nerve tissue comprises applying ablating energy to a second portion of the sacral nerve of the subject.

100. The method according to inventive concept 96, wherein performing the detection of the factor comprises detecting an ejaculation of the subject.

101. The method according to inventive concept 96, wherein performing the detection of the factor comprises detecting an electromyogram value.

102. The method according to inventive concept 96, wherein initiating action potentials comprises initiating action potentials during a second period, performing the detection of the factor comprises performing a second detection of the factor, and the method further comprises performing, during a first period, a first detection of the factor indicative of the parameter of the subject.

103. The method according to inventive concept 102, wherein performing the first detection comprises detecting a first ejaculation of the subject, and performing the second detection comprises detecting a second ejaculation of the subject.

104. The method according to inventive concept 102, wherein performing the first detection comprises detecting a first electromyogram value, and performing the second detection comprises detecting a second electromyogram value.

105. The method according to any one of inventive concepts 89-95, further comprising identifying that the subject suffers from erectile dysfunction, wherein initiating action potentials comprises initiating action potentials in response to the identifying.

106. The method according to inventive concept 105, wherein:
   initiating action potentials in the first portion of the nerve tissue comprises initiating action potentials in a first portion of a dorsal nerve of the subject, and
   applying ablating energy to the second portion of the nerve tissue comprises applying ablating energy to a second portion of the dorsal nerve of the subject.

107. The method according to inventive concept 105, wherein performing the detection comprises detecting an electromyogram value.

108. The method according to inventive concept 105, wherein performing the detection comprises detecting a blood pressure.

109. The method according to inventive concept 105, wherein initiating action potentials comprises initiating action potentials during a second period, performing the detection of the factor comprises performing a second detection of the factor, and the method further comprises performing, during a first period, a first detection of the factor indicative of the parameter of the subject.

110. The method according to inventive concept 109, wherein performing the first detection comprises detecting a first electromyogram value, and performing the second detection comprises detecting a second electromyogram value.

111. The method according to inventive concept 109, wherein performing the first detection comprises detecting a first blood pressure, and performing the second detection comprises detecting a second blood pressure.

112. The method according to any one of inventive concepts 89-95, further comprising identifying that the subject suffers from overactive bladder, wherein initiating action potentials comprises initiating action potentials in response to the identifying.

113. The method according to inventive concept 112, wherein:
   initiating action potentials in the first portion of the nerve tissue comprises initiating action potentials in a first portion of a hypogastric nerve of the subject, and
   applying ablating energy to the second portion of the nerve tissue comprises applying ablating energy to a second portion of the hypogastric nerve of the subject.

114. The method according to inventive concept 112, wherein:
   initiating action potentials in the first portion of the nerve tissue comprises initiating action potentials in a first portion of a sacral nerve of the subject, and
   applying ablating energy to the second portion of the nerve tissue comprises applying ablating energy to a second portion of the sacral nerve of the subject.

115. The method according to inventive concept 112, wherein performing the detection comprises detecting urinary urgency of the subject.

116. The method according to inventive concept 112, wherein performing the detection comprises detecting an electromyogram value.

117. The method according to inventive concept 112, wherein performing the detection comprises detecting pressure in a bladder of the subject.

118. The method according to inventive concept 112, wherein initiating action potentials comprises initiating action potentials while a bladder of the subject is at a pre-defined level of fullness.

119. The method according to inventive concept 112, wherein initiating action potentials comprises initiating action potentials during a second period, performing the detection of the factor comprises performing a second detection of the factor, and the method further comprises performing, during a first period, a first detection of the factor indicative of the parameter of the subject.

120. The method according to inventive concept 119, wherein performing the first detection comprises detecting a first urinary urgency, and performing the second detection comprises detecting a second urinary urgency.

121. The method according to inventive concept 119, wherein performing the first detection comprises detecting a first electromyogram value, and performing the second detection comprises detecting a second electromyogram value.

122. The method according to inventive concept 119, wherein performing the first detection comprises detecting a first pressure in a bladder of the subject, and performing the second detection comprises detecting a second pressure in the bladder of the subject.

123. The method according to any one of inventive concepts 89-95, further comprising identifying that the subject suffers from hypertension, wherein initiating action potentials comprises initiating action potentials in response to the identifying.

124. The method according to inventive concept 123, wherein:
   initiating action potentials in the first portion of the nerve tissue comprises initiating action potentials in a first portion of a renal nerve of the subject, and
   applying ablating energy to the second portion of the nerve tissue comprises applying ablating energy to a second portion of the renal nerve of the subject.

125. The method according to inventive concept 123, wherein:
   initiating action potentials in the first portion of the nerve tissue comprises initiating action potentials in a first portion of a glossopharyngeal nerve of the subject, and
   applying ablating energy to the second portion of the nerve tissue comprises applying ablating energy to a second portion of the glossopharyngeal nerve of the subject.

126. The method according to inventive concept 123, wherein:
  initiating action potentials in the first portion of the nerve tissue comprises initiating action potentials in a first portion of a Nerve of Hering of the subject, and
  applying ablating energy to the second portion of the nerve tissue comprises applying ablating energy to a second portion of the Nerve of Hering of the subject.

127. The method according to inventive concept 123, wherein performing the detection of the factor comprises detecting a blood pressure of the subject.

128. The method according to inventive concept 123, wherein initiating action potentials comprises initiating action potentials during a second period, performing the detection of the factor comprises performing a second detection of the factor, and the method further comprises performing, during a first period, a first detection of the factor indicative of the parameter of the subject.

129. The method according to inventive concept 128, wherein performing the first detection comprises detecting a first blood pressure of the subject, and performing the second detection comprises detecting a second blood pressure of the subject.

130. The method according to any one of inventive concepts 89-95, further comprising identifying that the subject suffers from chronic obstructive pulmonary disease, wherein initiating action potentials comprises initiating action potentials in response to the identifying.

131. The method according to inventive concept 130, wherein:
  initiating action potentials in the first portion of the nerve tissue comprises initiating action potentials in a first portion of a vagus nerve of the subject, and
  applying ablating energy to the second portion of the nerve tissue comprises applying ablating energy to a second portion of the vagus nerve of the subject.

132. The method according to inventive concept 130, wherein performing the detection of the factor comprises detecting a breathing-related factor of the subject.

133. The method according to inventive concept 132, wherein detecting the breathing-related factor comprises detecting an airflow.

134. The method according to inventive concept 132, wherein detecting the breathing-related factor comprises measuring a dimension of an airway of the subject.

135. The method according to inventive concept 132, wherein detecting the breathing-related factor comprises detecting blood chemistry of the subject.

136. The method according to inventive concept 130, wherein initiating action potentials comprises initiating action potentials during a second period, performing the detection of the factor comprises performing a second detection of the factor, and the method further comprises performing, during a first period, a first detection of the factor indicative of the parameter of the subject.

137. The method according to inventive concept 136, wherein performing the first detection comprises performing a first detection of a breathing-related factor of the subject, and performing the second detection comprises performing a second detection of the breathing-related factor of the subject.

138. The method according to inventive concept 137, wherein performing the first detection of the breathing-related factor of the subject comprises detecting a first airflow, and wherein performing the second detection of the breathing-related factor of the subject comprises detecting a second airflow.

139. The method according to any one of inventive concepts 89-95, further comprising identifying that the subject suffers from congestive heart failure, wherein initiating action potentials comprises initiating action potentials in response to the identifying.

140. The method according to inventive concept 139, wherein:
  initiating action potentials in the first portion of the nerve tissue comprises initiating action potentials in a first portion of a sympathetic nerve that innervates a heart of the subject, and
  applying ablating energy to the second portion of the nerve tissue comprises applying ablating energy to a second portion of the sympathetic nerve that innervates the heart of the subject.

141. The method according to inventive concept 139, wherein performing the detection comprises detecting a heart rate of the subject.

142. The method according to inventive concept 139, wherein performing the detection comprises detecting a blood pressure of the subject.

143. The method according to inventive concept 139, wherein initiating action potentials comprises initiating action potentials during a second period, performing the detection of the factor comprises performing a second detection of the factor, and the method further comprises performing, during a first period, a first detection of the factor indicative of the parameter of the subject.

144. The method according to inventive concept 143, wherein performing the first detection comprises detecting a first heart rate of the subject, and performing the second detection comprises detecting a second heart rate of the subject.

145. The method according to inventive concept 143, wherein performing the first detection comprises detecting a first blood pressure of the subject, and performing the second detection comprises detecting a second blood pressure of the subject.

146. The method according to any one of inventive concepts 89-95, further comprising identifying that the subject suffers from uterine bleeding, wherein initiating action potentials comprises initiating action potentials in response to the identifying.

147. The method according to inventive concept 146, wherein:
  initiating action potentials in the first portion of the nerve tissue comprises initiating action potentials in a first portion of a lumbar splanchnic nerve of the subject, and
  applying ablating energy to the second portion of the nerve tissue comprises applying ablating energy to a second portion of the lumbar splanchnic nerve of the subject.

148. The method according to inventive concept 146, wherein:
  initiating action potentials in the first portion of the nerve tissue comprises initiating action potentials in a first portion of a nerve that extends from a hypogastric plexus of the subject, and
  applying ablating energy to the second portion of the nerve tissue comprises applying ablating energy to a second portion of the nerve that extends from the hypogastric plexus of the subject.

149. The method according to inventive concept 146, wherein performing the detection of the factor comprises detecting uterine bleeding of the subject.

150. The method according to inventive concept 146, wherein performing the detection of the factor comprises detecting a blood pressure.

151. The method according to inventive concept 146, wherein performing the detection of the factor comprises detecting a dimension of a blood vessel of the subject.

152. The method according to inventive concept 146, wherein initiating action potentials comprises initiating action potentials during a second period, performing the detection of the factor comprises performing a second detection of the factor, and the method further comprises performing, during a first period, a first detection of the factor indicative of the parameter of the subject.

153. The method according to inventive concept 152, wherein performing the first detection comprises detecting a first uterine bleeding of the subject, and performing the second detection comprises detecting a second uterine bleeding of the subject.

154. The method according to inventive concept 152, wherein performing the first detection comprises detecting a first blood pressure, and performing the second detection comprises detecting a second blood pressure.

155. The method according to inventive concept 152, wherein performing the first detection comprises performing a first measurement of a blood vessel dimension, and performing the second detection comprises performing a second measurement of the blood vessel dimension.

156. The method according to any one of inventive concepts 89-95, further comprising identifying that the subject suffers from nervous stomach, wherein initiating action potentials comprises initiating action potentials in response to the identifying.

157. The method according to inventive concept 156, wherein:
  initiating action potentials in the first portion of the nerve tissue comprises initiating action potentials in a first portion of a vagus nerve of the subject, and
  applying ablating energy to the second portion of the nerve tissue comprises applying ablating energy to a second portion of the vagus nerve of the subject.

158. The method according to inventive concept 156, wherein performing the detection of the factor comprises detecting gastric pH.

159. The method according to inventive concept 156, wherein performing the detection of the factor comprises detecting gastric movement.

160. The method according to inventive concept 156, wherein initiating action potentials comprises initiating action potentials during a second period, performing the detection of the factor comprises performing a second detection of the factor, and the method further comprises performing, during a first period, a first detection of the factor indicative of the parameter of the subject.

161. The method according to inventive concept 160, wherein performing the first detection comprises detecting a first detection of gastric pH, and performing the second detection comprises detecting a second detection of gastric pH.

162. The method according to inventive concept 160, wherein performing the first detection comprises performing a first detection of gastric movement, and performing the second detection comprises performing a second detection of gastric movement.

163. The method according to any one of inventive concepts 89-95, further comprising identifying that the subject suffers from primary hyperhidrosis, wherein initiating action potentials comprises initiating action potentials in response to the identifying.

164. The method according to inventive concept 163, wherein:
  initiating action potentials in the first portion of the nerve tissue comprises initiating action potentials in a first portion of a sympathetic nerve that innervates sweat glands of the subject, and
  applying ablating energy to the second portion of the nerve tissue comprises applying ablating energy to a second portion of the sympathetic nerve that innervates sweat glands of the subject.

165. The method according to inventive concept 163, wherein performing the detection of the factor comprises detecting transepidermal water loss.

166. The method according to inventive concept 163, wherein performing the detection of the factor comprises detecting perspiration.

167. The method according to inventive concept 166, wherein detecting perspiration comprises detecting conduction between electrodes.

168. The method according to inventive concept 163, wherein initiating action potentials comprises initiating action potentials during a second period, performing the detection of the factor comprises performing a second detection of the factor, and the method further comprises performing, during a first period, a first detection of the factor indicative of the parameter of the subject.

169. The method according to inventive concept 168, wherein performing the first detection comprises performing a first detection of perspiration, and performing the second detection comprises performing a second detection of perspiration.

170. The method according to inventive concept 168, wherein performing the first detection comprises performing a first detection of transepidermal water loss, and performing the second detection comprises performing a second detection of transepidermal water loss.

171. The method according to any one of inventive concepts 89-95, further comprising identifying that the subject suffers from an inflammatory condition, wherein initiating action potentials comprises initiating action potentials in response to the identifying.

172. The method according to inventive concept 171, wherein:
  initiating action potentials in the first portion of the nerve tissue comprises initiating action potentials in a first portion of a splenic nerve of the subject, and
  applying ablating energy to the second portion of the nerve tissue comprises applying ablating energy to a second portion of the splenic nerve of the subject.

173. The method according to inventive concept 171, wherein performing the detection of the factor comprises detecting tumor-necrosis factor alpha in blood of the subject.

174. The method according to inventive concept 171, wherein initiating action potentials comprises initiating action potentials during a second period, performing the detection of the factor comprises performing a second detection of the factor, and the method further comprises performing, during a first period, a first detection of the factor indicative of the parameter of the subject.

175. The method according to inventive concept 174, wherein performing the first detection comprises performing a first detection of tumor-necrosis factor alpha in blood of the subject, and detecting the second detection comprises performing a second detection of tumor-necrosis factor alpha in the blood of the subject.

176. The method according to any one of inventive concepts 89-95, further comprising identifying that the subject suffers from obesity, wherein initiating action potentials comprises initiating action potentials in response to the identifying.

177. The method according to inventive concept 176, wherein:
    initiating action potentials in the first portion of the nerve tissue comprises initiating action potentials in a first portion of a nerve that conducts action potentials between a celiac plexus of the subject and an organ of the gastrointestinal system of the subject, and
    applying ablating energy to the second portion of the nerve tissue comprises applying ablating energy to a second portion of the nerve that conducts action potentials between the celiac plexus of the subject and the organ of the gastrointestinal system of the subject.

178. The method according to inventive concept 176, wherein performing the detection of the factor comprises detecting an electromyogram value.

179. The method according to inventive concept 176, wherein performing the detection of the factor comprises performing the detection using ultrasound.

180. The method according to inventive concept 176, wherein initiating action potentials comprises initiating action potentials during a second period, performing the detection of the factor comprises performing a second detection of the factor, and the method further comprises performing, during a first period, a first detection of the factor indicative of the parameter of the subject.

181. The method according to inventive concept 180, wherein performing the first detection comprises detecting a first electromyogram value, and performing the second detection comprises detecting a second electromyogram value.

182. The method according to inventive concept 180, wherein performing the first detection comprises performing the first detection using ultrasound, and performing the second detection comprises performing the second detection using ultrasound.

183. The method according to any one of inventive concepts 89-95, wherein applying the excitatory current comprises applying a first application of excitatory current, and the method further comprises:
    subsequently to applying the ablating energy, applying a second application of excitatory current; and
    after the start of the second application of excitatory current, performing another detection of the factor indicative of the parameter of the subject.

184. The method according to inventive concept 183, wherein applying ablating energy comprises applying a first application of ablating energy, and the method further comprises at least in part responsively to the detection and at least in part responsively to the other detection, applying a second application of ablating energy.

185. The method according to any one of inventive concepts 89-95, wherein initiating action potentials comprises initiating action potentials during a second period, performing the detection of the factor comprises performing a second detection of the factor, and the method further comprises performing, during a first period, a first detection of the factor indicative of the parameter of the subject.

186. The method according to inventive concept 185, wherein applying the excitatory current comprises applying a first application of excitatory current, and the method further comprises:
    subsequently to applying the ablating energy, applying a second application of excitatory current; and
    after the start of the second application of excitatory current, performing a third detection of the factor indicative of the parameter of the subject.

187. The method according to inventive concept 186, wherein applying ablating energy comprises applying a first application of ablating energy, and the method further comprises at least in part responsively to the second detection and at least in part responsively to the third detection, applying a second application of ablating energy.

188. The method according to inventive concept 187, wherein applying the second application of ablating energy comprises applying the second application of ablating energy at least in part responsively to the first detection.

189. The method according to inventive concept 185, further comprising, responsively to the first detection and the second detection, determining a sensitivity of the parameter to action potentials in the nerve tissue.

190. The method according to inventive concept 185, wherein applying ablating energy comprises iteratively repeating the steps of:
    (a) applying ablating energy,
    (b) subsequently, applying, to the first portion of the nerve, a selected excitatory current a characteristic of which is at least in part based on a value of at least one property of the excitatory current, and
    (c) after a start of the application of the selected excitatory current, detecting a detected ablated value of the factor,
until the detected ablated value crosses a threshold defined at least in part based on a target ablated value that has been generated at least in part based on the first detection and the second detection.

191. The method according to inventive concept 185, wherein applying the excitatory current comprises iteratively repeating the steps of:
    (a) applying the excitatory current,
    (b) after the start of the application of the excitatory current, detecting a detected excited value of the factor, and
    (c) altering a value of at least one property of the excitatory current,
until the detected excited value crosses a threshold defined at least in part on a target excited value of the factor, wherein detecting the detected excited value of the factor that crossed the threshold comprises performing the second detection of the factor.

192. The method according to any one of inventive concepts 89-95, wherein the nerve tissue includes nerve tissue associated with a blood vessel of the subject, applying the excitatory current comprises applying the excitatory current from within the blood vessel, and applying ablating energy comprises applying energy from within the blood vessel.

193. The method according to inventive concept 192, wherein the blood vessel includes a renal artery of the subject, applying the excitatory current comprises applying the excitatory current from within the renal artery, and applying ablating energy comprises applying energy from within the renal artery.

There is further provided, in accordance with an application of the present invention, an inventive concept including:
194. A method for use with nerve tissue of a subject, the nerve tissue conducting endogenous action potentials to an anatomical structure of the subject, the structure being capable of altering a parameter of the subject at least in part responsively to the endogenous action potentials, the method comprising:

during a first period, performing a first detection of a factor indicative of the parameter of the subject at rest;

during a second period, initiating action potentials in the nerve tissue by applying an excitatory current to the nerve tissue and, after the start of the application of the excitatory current, performing a second detection of the factor indicative of the parameter of the subject; and at least in part responsively to the first detection and to the second detection, selecting the subject for a treatment comprising ablation of the nerve tissue.

There is further provided, in accordance with an application of the present invention, an inventive concept including:

195. A method for use with a carotid body of a subject, the carotid body being capable of inducing endogenous action potentials that affect blood pressure of the subject, the method comprising:

applying an excitatory current to the carotid body;

after a start of the application of the excitatory current, performing a detection of a factor indicative of blood pressure of the subject; and subsequently, applying ablating energy to the carotid body, at least in part in response to the detection.

196. The method according to inventive concept 195, wherein performing the detection after the start of the application of the excitatory current comprises performing the detection during the application of the excitatory current.

197. The method according to inventive concept 195, wherein performing the detection after the start of the application of the excitatory current comprises performing the detection after the application of the excitatory current.

198. The method according to inventive concept 195, wherein stimulating comprises stimulating during a second period, performing the detection of the factor comprises performing a second detection of the factor, and the method further comprises performing, during a first period, a first detection of the factor.

199. The method according to any one of inventive concepts 195-198, wherein applying the excitatory current comprises applying a first application of excitatory current, and the method further comprises:

subsequently to applying the ablating energy, applying a second application of excitatory current; and after the start of the second application of excitatory current, performing another detection of the factor.

200. The method according to inventive concept 199, wherein applying ablating energy comprises applying a first application of ablating energy, and the method further comprises at least in part responsively to the detection and at least in part responsively to the other detection, applying a second application of ablating energy.

201. The method according to any one of inventive concepts 195-198, wherein applying the excitatory current comprises applying the excitatory current during a second period, performing the detection of the factor comprises performing a second detection of the factor, and the method further comprises performing, during a first period, a first detection of the factor.

202. The method according to inventive concept 201, wherein applying the excitatory current comprises applying a first application of excitatory current, and the method further comprises:

subsequently to applying the ablating energy, applying a second application of excitatory current; and after the start of the second application of excitatory current, performing a third detection of the factor indicative of the parameter of the subject.

203. The method according to inventive concept 202, wherein applying ablating energy comprises applying a first application of ablating energy, and the method further comprises at least in part responsively to the second detection and at least in part responsively to the third detection, applying a second application of ablating energy.

204. The method according to inventive concept 203, wherein applying the second application of ablating energy comprises applying the second application of ablating energy at least in part responsively to the first detection.

205. The method according to inventive concept 201, further comprising, responsively to the first detection and the second detection, determining a sensitivity of the parameter to action potentials induced by the carotid body.

206. The method according to inventive concept 201, further comprising, responsively to the first detection and the second detection, selecting the subject for a treatment comprising ablation of the nerve tissue.

207. The method according to inventive concept 201, wherein applying ablating energy comprises iteratively repeating the steps of:

(a) applying ablating energy, (b) subsequently, applying, a selected excitatory current a characteristic of which is at least in part based on a value of at least one property of the excitatory current, and (c) after a start of the application of the selected excitatory current, detecting a detected ablated value of the factor, until the detected ablated value crosses a threshold defined at least in part based on a target ablated value that has been generated at least in part based on the first detection and the second detection.

208. The method according to inventive concept 201, wherein applying the excitatory current comprises iteratively repeating the steps of:

(a) applying the excitatory current, (b) after the start of the application of the excitatory current, detecting a detected excited value of the factor, and (c) altering a value of at least one property of the excitatory current, until the detected excited value crosses a threshold defined at least in part on a target excited value of the factor, wherein detecting the detected excited value of the factor that crossed the threshold comprises performing the second detection of the factor.

There is further provided, in accordance with an application of the present invention, an inventive concept including:

209. A method for use with a renal nerve of a subject, the renal nerve innervating an ipsilateral kidney of the subject, the method comprising:

receiving a preliminary blood pressure value of the subject;

iteratively repeating the steps of:

(a) inducing action potentials in the renal nerve by applying an excitatory current to a first portion of the renal nerve, (b) receiving a detected excited blood pressure value, indicative of a blood pressure of the subject after a start of the application of the excitatory current, and (c) altering a value of at least one property of the excitatory current, until the detected excited blood pressure value crosses a first threshold defined at least in part based on a pre-determined target excited blood pressure value; and subsequently, iteratively repeating the steps of:
(d) applying ablating energy to a second portion of the renal nerve that is further from the kidney than is the first portion of the renal nerve,
(e) subsequently, applying, to the first portion of the renal nerve, a selected excitatory current a characteristic of which is at least in part based on the value of the at least one property at which the detected excited blood pressure value crossed the first threshold, and
(f) receiving a detected ablated blood pressure value, indicative of a blood pressure of the subject after a start of the application of the selected excitatory current, until the detected ablated blood pressure value crosses a second threshold defined at least in part based on a target ablated blood pressure value that is generated at least in part based on the preliminary blood pressure value and at least in part based on at least one excited blood pressure value selected from the group consisting of: (i) the target excited blood pressure value and (ii) the detected excited blood pressure value.

210. The method according to inventive concept 209, wherein applying ablating energy comprises applying a radio-frequency current having a frequency of between 5 kHz and 1 GHz.

211. The method according to inventive concept 209, wherein receiving the target ablated blood pressure value comprises receiving a target ablated blood pressure value that is manually inputted by a healthcare provider.

212. The method according to inventive concept 209, wherein:
the renal nerve includes a first renal nerve of the subject that innervates a first kidney that is ipsilateral to the first renal nerve; and
inducing action potentials in the renal nerve comprises (i) inducing action potentials in the first renal nerve, and (ii) inducing action potentials in a second renal nerve that innervates a second kidney that is ipsilateral to the second renal nerve.

213. The method according to inventive concept 209, wherein, subsequently to the first iteration of steps d, e and f, during at least one iteration of steps d, e and f, applying ablating energy comprises applying ablating energy that is different in at least one characteristic thereof compared to the ablative energy applied in a previous iteration of steps d, e and f.

214. The method according to inventive concept 209, further comprising detecting, using a sensor, the detected excited blood pressure value.

215. The method according to inventive concept 209, further comprising detecting, using a sensor, the detected ablated blood pressure value.

216. The method according to inventive concept 209, further comprising generating the target excited blood pressure value at least in part responsively to the preliminary blood pressure value.

217. The method according to inventive concept 209, wherein receiving the target excited blood pressure value comprises receiving a target excited blood pressure value that is manually inputted by a healthcare provider.

218. The method according to any one of inventive concepts 209-217, wherein applying the excitatory current to the first portion of the renal nerve comprises applying the excitatory current via a plurality of sub-electrodes arranged in a broken arc that traces an inner wall of a renal artery of the subject.

219. The method according to inventive concept 218, wherein applying the excitatory current comprises applying the excitatory current simultaneously via the plurality of sub-electrodes.

220. The method according to inventive concept 219, wherein the plurality of sub-electrodes includes a plurality of independently addressable sub-electrodes, and applying the excitatory current comprises applying the excitatory current via the plurality of independently addressable sub-electrodes.

221. The method according to inventive concept 219, further comprising balancing the excitatory current across the plurality of sub-electrodes.

222. The method according to any one of inventive concepts 209-217, further comprising generating the target ablated blood pressure value at least in part responsively to (1) the preliminary blood pressure value and (2) at least one excited blood pressure value selected from the group consisting of (i) the target excited blood pressure value and (ii) the detected excited blood pressure value.

223. The method according to inventive concept 222, wherein generating the target ablated blood pressure value comprises generating the target excited blood pressure value at least in part responsively to a value indicative of a target degree of ablation of the renal nerve.

224. The method according to inventive concept 223, further comprising receiving, via a manual input, the value indicative of the target degree of ablation.

There is further provided, in accordance with an application of the present invention, an inventive concept including:

225. A method for ablating nerve tissue of a renal artery of a subject, the method comprising:
applying a non-ablative electrical current to the nerve tissue;
subsequently applying a first application of ablative energy to the nerve tissue;
receiving (1) a first value of the subject, the first value being indicative of a blood pressure of the subject after a start of the application of the non-ablative electrical current and before the first application of ablative energy, and (2) a second value of the subject, the second value being indicative of the blood pressure of the subject after the first application of ablative energy; and
at least in part responsively to a difference between the first value and the second value, applying a second application of ablative energy to the nerve tissue.

226. The method according to inventive concept 225, wherein applying the first application of ablative energy comprises applying a first application of a radio-frequency current having a frequency of between 5 kHz and 1 GHz.

227. The method according to inventive concept 225, wherein the renal nerve innervates an ipsilateral kidney of the subject, applying the non-ablative electrical current comprises applying the non-ablative electrical current to a first portion of the nerve tissue, and applying the first application of ablative energy comprises applying the first application of ablative energy to a second portion of the nerve tissue that is further from the kidney than is the first portion of the nerve tissue.

228. The method according to inventive concept 225, wherein applying the second application of the ablative energy comprises applying a second application of ablative energy that has an intensity that is greater than an intensity of the first application of the ablative energy.

229. The method according to inventive concept 225, wherein receiving the first value comprises receiving a first value that is indicative of a blood pressure of the subject after an end of the application of the non-ablative electrical current.

230. The method according to inventive concept 225, further comprising receiving a preliminary value indicative of the parameter of the subject before the application of the non-ablative electrical current, wherein applying the ablative energy comprises applying the ablative energy at least in part responsively to (1) the difference between the first value and the second value, and (2) the preliminary value.

231. The method according to inventive concept 225, wherein receiving the first value indicative of the parameter of the subject after the start of the application of the non-ablative electrical current comprises receiving the first value indicative of the parameter of the subject during the application of the non-ablative electrical current.

232. The method according to inventive concept 225, wherein receiving the first value indicative of the parameter of the subject after the start of the application of the non-ablative electrical current comprises receiving the first value indicative of the parameter of the subject after the application of the non-ablative electrical current.

233. The method according to inventive concept 225, wherein the non-ablative electrical current includes an excitatory current, and wherein applying the non-ablative electrical current comprises initiating action potentials in the nerve tissue using the excitatory current.

234. The method according to inventive concept 225, wherein the non-ablative electrical current includes a blocking current, and wherein applying the non-ablative electrical current comprises blocking action potentials in the nerve tissue using the blocking current.

235. The method according to any one of inventive concepts 225-234, wherein:
the renal artery includes a first renal artery of the subject, and
applying the non-ablative electrical current comprises applying the non-ablative electrical current to the nerve tissue of the first renal artery and to nerve tissue of a second renal artery of the subject.

236. The method according to inventive concept 235, wherein applying the non-ablative electrical current comprises applying the non-ablative electrical current to the nerve tissue of the first renal artery and to nerve tissue of the second renal artery generally at the same time.

237. The method according to any one of inventive concepts 225-234, wherein applying the non-ablative electrical current comprises applying the non-ablative electrical current via a plurality of sub-electrodes arranged in a broken arc that traces an inner wall of the renal artery.

238. The method according to inventive concept 237, wherein applying the non-ablative electrical current comprises applying the non-ablative electrical current simultaneously via the plurality of sub-electrodes.

239. The method according to inventive concept 237, wherein the plurality of sub-electrodes includes a plurality of independently addressable sub-electrodes, and applying the non-ablative electrical current comprises applying the non-ablative electrical current via the plurality of independently addressable sub-electrodes.

240. The method according to inventive concept 238, further comprising balancing the non-ablative electrical current across the plurality of sub-electrodes.

There is further provided, in accordance with an application of the present invention, an inventive concept including:

241. A method for use with nerve tissue of a subject, the nerve tissue conducting endogenous action potentials to an anatomical structure of the subject, the structure being capable of altering a parameter of the subject at least in part responsively to the endogenous action potentials, the method comprising:
during a first period, blocking the endogenous action potentials from propagating through the nerve tissue by applying a non-ablative blocking current to the nerve tissue and, after the start of the application of the non-ablative blocking current, detecting a first value of a factor indicative of the parameter of the subject; and
during a second period, initiating unidirectional action potentials in the nerve tissue by applying an excitatory current to the nerve tissue and, after the start of the application of the excitatory current, detecting a second value of the factor indicative of the parameter of the subject.

242. The method according to inventive concept 241, wherein:
the anatomical structure includes a first anatomical structure of the subject, and the nerve tissue includes a respective first section of nerve tissue that conducts endogenous action potentials to the first anatomical structure; and
blocking the endogenous action potentials comprises (i) blocking the endogenous action potentials from propagating through the first section of nerve tissue, and (ii) blocking endogenous action potentials from propagating through a second section of nerve tissue to a respective second anatomical structure of the subject.

243. The method according to inventive concept 241, further comprising, during a third period, detecting a third value of the factor indicative of the parameter of the subject in the absence of the non-ablative blocking current and the excitatory current.

244. The method according to inventive concept 241, further comprising, responsively to the first and second values, determining a sensitivity of the parameter to action potentials in the nerve tissue.

245. The method according to inventive concept 241, further comprising, responsively to the first and second values, selecting the subject for a treatment comprising ablation of the nerve tissue.

246. The method according to inventive concept 241, wherein detecting the first value after the start of the application of the non-ablative blocking current comprises detecting the first value during the application of the non-ablative blocking current.

247. The method according to inventive concept 241, wherein detecting the first value after the start of the application of the non-ablative blocking current comprises detecting the first value after the application of the non-ablative blocking current.

248. The method according to inventive concept 241, wherein detecting the second value after the start of the application of the excitatory current comprises detecting the second value during the application of the excitatory current.

249. The method according to inventive concept 241, wherein detecting the second value after the start of the application of the excitatory current comprises detecting the second value after the application of the excitatory current.

250. The method according to any one of inventive concepts 241-249, wherein applying the non-ablative blocking current comprises applying the non-ablative blocking current via a plurality of sub-electrodes arranged in a broken arc.

251. The method according to inventive concept 250, wherein applying the non-ablative blocking current comprises applying the non-ablative blocking current simultaneously via the plurality of sub-electrodes.

252. The method according to inventive concept 251, wherein the plurality of sub-electrodes includes a plurality of independently addressable sub-electrodes, and applying the non-ablative blocking current comprises applying the non-ablative blocking current via the plurality of independently addressable sub-electrodes.

253. The method according to inventive concept 251, further comprising balancing the non-ablative blocking current across the plurality of sub-electrodes.

254. The method according to any one of inventive concepts 241-249, wherein the nerve tissue includes nerve tissue of a blood vessel of a subject, and wherein blocking and initiating comprise blocking and initiating using an electrode unit disposed within the blood vessel of the subject.

255. The method according to inventive concept 254, wherein the nerve tissue includes a renal nerve of the subject, the blood vessel includes a renal artery of the subject, and blocking and initiating comprise blocking and initiating using an electrode unit disposed within the renal artery of the subject.

256. The method according to inventive concept 254, wherein the factor includes a factor indicative of a blood pressure of the subject, detecting the first value comprises detecting a first value of the factor indicative of the blood pressure of the subject, and detecting the second value comprises detecting a second value of the factor indicative of the blood pressure of the subject.

257. The method according to any one of inventive concepts 241-249, wherein:
the method further comprises applying ablative energy to a first portion of the nerve tissue of the subject,
initiating the unidirectional action potentials during the second period comprises initiating the unidirectional action potentials in a second portion of the nerve tissue by applying a first application of the excitatory current to the second portion of the nerve tissue prior to the application of ablative energy, and detecting the second value of the factor comprises detecting the second value of the factor prior to the application of ablative energy, and
the method further comprises, during a third period, subsequently to the application of ablative energy, initiating unidirectional action potentials in the nerve tissue by applying a second application of the excitatory current to the second portion of the nerve tissue and, after the start of the second application of the excitatory current, detecting a third value of the factor indicative of the parameter of the subject.

258. The method according to inventive concept 257, wherein:
applying ablative energy comprises applying a first application of ablative energy, and
the method further comprises, at least in part responsively to the second value and the third value, applying a second application of ablative energy to the first portion of the nerve tissue of the subject.

259. The method according to inventive concept 258, wherein applying the second application of ablative energy comprises applying the second application of ablative energy at least in part responsively to the first value.

260. The method according to inventive concept 258, wherein applying the second application of ablative energy comprises applying a second application of ablative energy that has an intensity different from an intensity of the first application of ablative energy.

There is further provided, in accordance with an application of the present invention, an inventive concept including:
261. A method for use with a renal artery of a subject, the renal artery including nerve tissue, the method comprising:
generating a lesion in the renal artery of the subject;
initiating first unidirectional action potentials on a first side of the lesion, such that the action potentials propagate toward the lesion; and
initiating second unidirectional action potentials on a second side of the lesion, such that the action potentials propagate toward the lesion.

There is further provided, in accordance with an application of the present invention, an inventive concept including:
262. A method, comprising:
measuring a first blood pressure value of a subject who does not suffer from hypertension;
subsequently, at least partly ablating nerve tissue of a renal artery of the subject;
subsequently, measuring a second blood pressure value of the subject; and
subsequently, at least in part responsively to the first blood pressure value, and at least in part responsively to the second blood pressure value, further ablating the nerve tissue.

There is further provided, in accordance with an application of the present invention, an inventive concept including:
263. A method for facilitating ablation of renal nerve tissue of a renal artery of a subject, the method comprising:
introducing into a subject, a transvascular catheter including (1) at a distal portion thereof, an electrode unit and an ablation unit disposed proximally from the electrode unit, and (2) a pressure sensor disposed proximally from the ablation unit;
transfemorally advancing the transvascular catheter into an operative position in which the distal portion is disposed within the renal artery of the subject, and the pressure sensor is disposed in an aorta of the subject; and
while the transvascular catheter is in the operative position, activating a control unit to drive the electrode unit to apply an electrical current to the nerve tissue.

264. The method according to inventive concept 263, wherein the step of introducing comprises introducing into the subject a transvascular catheter including (1) at a distal portion thereof, an electrode unit and an ablation unit disposed proximally from the electrode unit, and (2) a pressure sensor disposed more than 2 cm proximally from the ablation unit.

265. The method according to inventive concept 263, wherein:
the distal portion includes a first distal portion thereof,
the transvascular catheter is bifurcated so as to have the first distal portion and a second distal portion, and
transfemorally advancing comprises transfemorally advancing the transvascular catheter such that the second distal portion is disposed within another renal artery of the subject.

266. The method according to inventive concept 263, wherein activating the control unit comprises activating a control unit that is coupled to the transvascular catheter, such that the control unit:
drives the electrode unit to apply a non-ablative electrical current to the nerve tissue,
subsequently drives the ablation unit to apply a first application of ablative energy to the nerve tissue, receives, from the pressure sensor, (1) a first value of the subject, the first value being indicative of a blood pressure of the subject after a start of the application of the non-ablative electrical current and before the first application of ablative energy, and (2) a second value of the subject, the second value being indicative of the blood pressure of the subject after the first application of ablative energy, and at least in part responsively to a difference between the first value and the second value, drives the ablation unit to apply a second application of ablative energy to the nerve tissue.

267. The method according to any one of inventive concepts 263-266, wherein activating the control unit comprises activating a control unit that is coupled to the transvascular catheter, such that the control unit:

receives, from the pressure sensor, a preliminary blood pressure value of the subject;

iteratively repeats the steps of:
(a) inducing action potentials in the renal nerve tissue by applying an excitatory current to a first portion of the renal nerve tissue,
(b) receiving, from the pressure sensor, a detected excited blood pressure value, indicative of a blood pressure of the subject after a start of the application of the excitatory current, and
(c) altering a value of at least one property of the excitatory current, until the detected excited blood pressure value crosses a first threshold defined at least in part based on a pre-determined target excited blood pressure value, and subsequently, iteratively repeats the steps of:
(d) applying ablating energy to a second portion of the renal nerve tissue that is further from the kidney than is the first portion of the renal nerve tissue,
(e) subsequently, applying, to the first portion of the renal nerve tissue, a selected excitatory current a characteristic of which is at least in part based on the value of the at least one property at which the detected excited blood pressure value crossed the first threshold, and
(f) receiving, from the pressure sensor, a detected ablated blood pressure value, indicative of a blood pressure of the subject after a start of the application of the selected excitatory current, until the detected ablated blood pressure value crosses a second threshold defined at least in part based on a target ablated blood pressure value that is generated at least in part based on the preliminary blood pressure value and at least in part based on at least one excited blood pressure value selected from the group consisting of (i) the target excited blood pressure value and (ii) the detected excited blood pressure value.

268. The method according to inventive concept 267, wherein activating the control unit comprises activating the control unit such that the control unit generates the target excited blood pressure value at least in part responsively to the preliminary blood pressure value.

269. The method according to inventive concept 267, further comprising inputting, into an interface of the control unit, the target excited blood pressure value.

270. The method according to inventive concept 267, wherein activating the control unit comprises activating the control unit such that the control unit generates the target ablated blood pressure value at least in part responsively to (1) the preliminary blood pressure value and (2) at least one excited blood pressure value selected from the group consisting of (i) the target excited blood pressure value and (ii) the detected excited blood pressure value.

271. The method according to inventive concept 270, further comprising inputting, into an interface of the control unit, a value indicative of a target degree of ablation of the renal nerve tissue, wherein activating the control unit comprises activating the control unit such that the control unit generates the target excited blood pressure value at least in part responsively to the value indicative of the target degree of ablation.

272. The method according to inventive concept 267, further comprising inputting, into an interface of the control unit, the target ablated blood pressure value.

The present invention will be more fully understood from the following detailed description of applications thereof, taken together with the drawings, in which:

BRIEF DESCRIPTION OF THE DRAWINGS

FIG. 1 is a schematic illustration of a system for ablating nerve tissue of a blood vessel of a subject, in accordance with some applications of the invention;

FIGS. 2A-H are schematic illustrations of a technique for facilitating ablation of nerve tissue of the blood vessel of the subject, in accordance with some applications of the invention;

FIG. 3, is a schematic illustration of some techniques for facilitating ablation of nerve tissue of the renal artery, in accordance with some applications of the invention;

FIG. 4 is a flow diagram of at least some steps in the techniques described with reference to FIGS. 2A-H and 3;

FIGS. 5A-B are schematic illustrations of systems for ablating nerve tissue of at least one renal artery of a subject, in accordance with some applications of the invention;

FIGS. 6-8 are schematic illustrations of systems for ablating nerve tissue of a blood vessel of a subject, in accordance with some applications of the invention;

FIGS. 9A-B are schematic illustrations of electrodes, in accordance with some applications of the invention;

FIG. 10 is a flow diagram, illustrating at least some steps in ablating nerve tissue of the renal artery of the subject, in accordance with some applications of the invention;

FIG. 11 is a flow diagram, illustrating automation of at least some of the steps described with reference to FIG. 10, in accordance with some applications of the invention;

DETAILED DESCRIPTION OF EMBODIMENTS

Figure 2B:
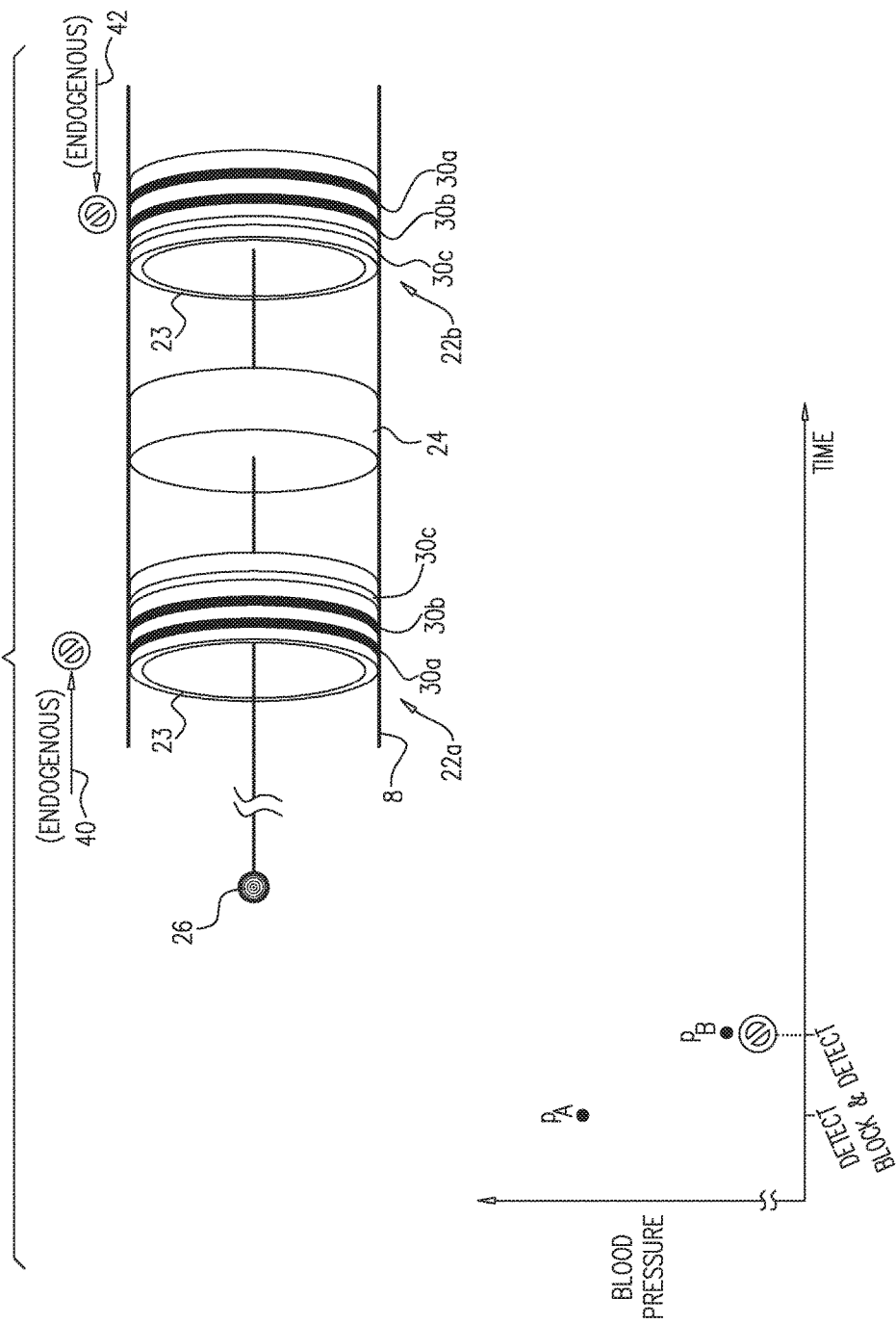

Reference is made to FIG. 1, which is a schematic illustration of a system 20 for ablating nerve tissue of a blood vessel of a subject, in accordance with some applications of the invention. System 20 comprises an intravascular device 21 that comprises at least one electrode unit 22, an ablation unit 24, and a sensor 26. Sensor 26 is configured to detect a parameter of the subject, such as a parameter indicative of blood pressure, heart rate, and/or blood flow. Ablation unit 24 is configured to ablate the nerve tissue of the blood vessel by applying ablation energy thereto, so as to block endogenous action potentials from propagating through the nerve tissue (e.g., to ablate nerve tissue in a first portion of the nerve tissue, so as to permanently block pathogenic action potentials from propagating past the first portion of the nerve tissue). Electrode unit 22 is configured to apply a non-ablative electrical current to the nerve tissue, typically so as to initiate and/or block action potentials in the nerve tissue (e.g., to apply the non-ablative electrical current to a second portion of the nerve tissue, so as to initiate and/or temporarily block action potentials in the second portion of the nerve tissue).

Typically, when electrode unit 22 is configured to initiate action potentials in the nerve tissue, it is configured to initiate action potentials that have similar characteristics and/or effects as the endogenous action potentials that the ablation unit is configured to block by ablating the nerve tissue. The parameter that sensor 26 is configured to detect is typically a parameter that changes in response to action potentials in the nerve tissue (e.g., in response to the endogenous action potentials and the induced action potentials, and in response to the blocking of the endogenous action potentials). That is, sensor 26 is configured to detect a physiological response to electrode unit 22 blocking the endogenous action potentials and/or initiating the induced action potentials, and/or to ablation unit 24 ablating the nerve tissue, and thereby blocking the action potentials.

Although units 22a, 22b and 24 are shown as distinct elements, for some applications intravascular device 21 is an integral unit that comprises and/or defines units 22a, 22b and 24. For example, device 21 may define units 22a, 22b and 24 by comprising the components (e.g., electrodes) of units 22a, 22b and 24 (e.g., device 21 may comprise a stent-like body and a plurality of electrodes, distributed along the length of the body).

Typically, at least electrode unit 22 and ablation unit 24 are coupled to a single longitudinal member, such as a catheter 28, and the longitudinal member, electrode unit 22, and ablation unit 24 are advanceable together, such as within and/or through a sheath 29. For some applications, and as shown in FIG. 1, sensor 26 is also coupled to catheter 28 and is advanceable therewith.

For some applications, and as shown in FIG. 1, system 20 comprises two electrode units 22 (e.g., electrode unit 22a and electrode unit 22b). Electrode unit 22a is disposed proximally from ablation unit 24, and electrode unit 22b is disposed distally from ablation unit 24. Typically, each electrode unit 22 is configured to initiate unidirectional action potentials in the nerve tissue, such as by providing an excitatory current adjacent to a non-ablative blocking current, e.g., as is known in the nerve cuff art, such as a cathodic or anodic DC blocking current, or a high-frequency (HF) blocking current (e.g., an HF blocking current having a frequency of greater than 4 kHz, less than 6 kHz and/or between 4 and 6 kHz). For example, each electrode unit 22 may comprise one or more (e.g., three or more) electrodes 30 (e.g., electrodes 30a, 30b, and 30c), electrodes 30a and 30b being driven (e.g., by a control unit 32) to apply a non-ablative blocking current, and electrode 30c being driven to apply an excitatory current that initiates action potentials that thereby propagate only in the direction away from the other two electrodes (i.e., the action potentials are blocked from propagating past the other two electrodes). Typically, the excitatory current has a lower frequency than the non-ablative blocking current. Further typically, the excitatory current has a frequency of greater than 1 Hz and/or less than 100 Hz, such as between 1 and 100 Hz, e.g., between 10 and 100 Hz. When each electrode unit 22 is configured to initiate unidirectional action potentials, the electrode units are oriented on catheter 28 such that the unidirectional action potentials initiated by each electrode unit propagate toward the nerve tissue that is adjacent to ablation unit 24 (e.g., toward the first portion of the nerve tissue).

For applications in which system 20 comprises two electrode units, the electrode units are thereby also oriented such that the unidirectional action potentials initiated by each electrode unit propagate toward the other electrode unit. For applications in which system 20 comprises only one electrode unit, that electrode unit may comprise electrode unit 22a or 22b (e.g., that electrode unit may be disposed in the position and/or orientation described for electrode unit 22a or 22b). It should be noted that, although control unit 32 is shown in FIG. 1 as being outside of the blood vessel(s) in which the electrode units and ablation unit are disposed (e.g., outside the body of the subject), for some applications, control unit 32 and/or other controllers are configured to be intracorporeal (e.g., to be disposed within the blood vessel(s) in which the electrode units and ablation unit are disposed).

For some applications, ablation unit 24 comprises one or more electrodes, and is configured to ablate the nerve tissue by applying radio frequency (RF) current to the nerve tissue (e.g., ablation unit 24 comprises an RF ablation unit that is configured to be driven by control unit 32 to apply the RF current). For some applications, the RF current has a frequency of above 5 kHz and/or below 1 GHz, such as between 5 kHz and 1 GHz (e.g., 10 kHz-10 MHz, e.g., 50 kHz-1 MHz, e.g., 300 kHz-1 MHz, e.g., 300 kHz-500 kHz). For some such applications, ablation unit 24 comprises a plurality of electrodes arranged at different positions along the axis of catheter 28 (e.g., at different distances from the electrode unit), such that when disposed within renal artery 8, each of the plurality of electrodes of the ablation unit is disposed adjacent to a different site of the nerve tissue of the renal artery. Typically, for such applications, a different one of the plurality of electrodes is used for each application of ablation energy (described hereinbelow), such that a different site of nerve tissue is ablated by each application of ablation energy.

For some applications, ablation unit 24 comprises one or more ultrasound transducers, and is configured to ablate the nerve tissue by applying ultrasound energy to the nerve tissue (e.g., ablation unit 24 comprises an ultrasound ablation unit that is configured to be driven by control unit 32 to apply the ultrasound energy). Ablation unit 24 may alternatively or additionally be configured to ablate the nerve tissue cryogenically, using laser, using resistive heating, using chemical ablation, or via another ablation mechanism.

Reference is now made to FIGS. 1 and 2A-H, FIGS. 2A-H being schematic illustrations of a technique for facilitating ablation of nerve tissue of the blood vessel of the subject using system 20, in accordance with some applications of the invention. In FIGS. 1 and 2A-H, the blood vessel comprises a renal artery 8 of the subject, disposed between a kidney 10 and the aorta 12 (e.g., the abdominal aorta) of the subject, and system 20 is configured to ablate nerve tissue of the renal artery, so as to treat hypertension. However, for other applications, system 20 may be used to ablate nerve tissue of another blood vessel, such as the carotid artery (e.g., the carotid sinus) or the aortic arch. For example, hypertension may alternatively or additionally be treated by ablation of chemoreceptors and/or baroreceptors in the carotid sinus, and/or nerve tissue associated therewith, and/or ablation of sympathetic nerve tissue of the aortic arch. Furthermore, system 20 may be used to ablate nerve tissue at other sites, such as at a pulmonary vein ostium.

System 20 is advanced percutaneously (e.g., transluminally, such as transfemorally) such that at least electrode units 22a and 22b, and ablation unit 24 are disposed within renal artery 8. Thereby, electrode units 22a and 22b, and ablation unit 24 are adjacent to respective portions of the nerve tissue of the renal artery. Typically, sensor 26 is configured to detect a parameter indicative of blood pressure of the subject (e.g., sensor 26 may comprise a pressure sensor). Typically, sensor 26 is coupled to catheter 28 such that when the electrode units and ablation unit are disposed in renal artery 8, the sensor is disposed in aorta 12 (or alternatively in the femoral artery). For example, sensor 26 may be disposed greater than 2 cm and/or less than 70 cm (e.g., between 2 and 50 cm, such as between 2 and 30 cm, or between 5 and 40 cm) proximally from intravascular device 21 and/or one or more components thereof. Alternatively, system 20 may be configured such that sensor 26 is disposed in renal artery 8. Sensor 26 may alternatively be configured to detect a parameter indicative of blood flow of the subject. For example, sensor 26 may comprise an ultrasound transceiver, configured to detect the blood flow using Doppler ultrasound. For some such applications, sensor 26 may be extracorporeal (e.g., not coupled to catheter 28).

Following delivery to renal artery 8, electrode units 22a and 22b are typically expanded from a compressed delivery state, to an expanded state in which electrodes 30 are placed in contact with the wall of the renal artery, and in which fluid communication is maintained between the aorta 12 and kidney 10. For example, and as shown in FIGS. 1 and 2A-H, each electrode unit may comprise a tubular element 23, such as a stent, on which electrodes 30 are disposed. Alternatively, each electrode unit may comprise discrete "lasso"-type electrodes that are not coupled to a tubular element. For some applications (e.g., for applications in which ablation unit 24 comprises an RF ablation unit), ablation unit 24 is also expanded from a compressed delivery state to an expanded state thereof. For some such applications, electrode units 22 and ablation unit 24 are disposed on a single tubular element, and/or comprise an integrated device. Alternatively (e.g., for applications in which ablation unit 24 comprises an ultrasound ablation unit), ablation unit 24 is not expanded (e.g., does not require contact with the wall of renal artery 8).

FIGS. 2A-H show sequential steps in a technique of ablating nerve tissue of renal artery 8, using system 20, in accordance with some applications of the invention. Each of FIGS. 2A-H shows a state of system 20 for a respective step, and a corresponding illustrative chart of blood pressure detected up until, and including, the respective step.

Following placement of system 20 in the body of the subject (e.g., as described hereinabove), sensor 26 detects a blood pressure $p\_A$ of the subject (FIG. 2A). For some applications, detected blood pressure $p\_A$ represents an "untreated" blood pressure. Endogenous efferent action potentials 40 and endogenous afferent action potentials 42 are shown propagating along nerve tissue of renal artery 8 (e.g., between kidney 10 and the central nervous system (CNS) of the subject). It is to be noted that blood pressure $p\_A$, and the other detected blood pressures described herein, are typically each detected while the subject is in the same state (e.g., reclining and/or sedated), so as to reduce variability.

FIG. 2B shows electrode units 22a and 22b each applying a non-ablative blocking current to the nerve tissue of renal artery 8. It is to be noted that throughout the specification, the blocking current is referred to as the "non-ablative blocking current," so as to be distinct from any current of ablative energy applied by the ablation unit, which may otherwise be considered a "blocking current" because of the blocking effect of the resulting ablation. It is to be further noted that, although the excitatory current applied by the electrode units is also non-ablative, it is generally referred to as the "excitatory current".

As described hereinabove, for some applications, the electrode units drive the non-ablative blocking current via electrodes 30a and 30b. For some applications, only one of the electrode units applies the non-ablative blocking current. Endogenous efferent action potentials 40 and endogenous afferent action potentials 42 are shown being blocked from propagating along nerve tissue of renal artery 8, by the non-ablative blocking current. It is hypothesized that this blocking of endogenous action potentials has similar effects to ablation of nervous tissue of the renal artery (e.g., to decrease systemic blood pressure), as is known in the art.

After the start of the application of the non-ablative blocking current (e.g., while the non-ablative blocking current is being applied, or after it has stopped being applied) sensor 26 detects a blood pressure $p\_B$ of the subject. (In general, sensing may also be performed at any other time, e.g., continuously.) For example, the blood pressure may be detected after a duration in which blood pressure is allowed to respond to the reduction in renal nerve activity. The non-ablative blocking current may be calibrated in real-time (e.g., by adjusting amplitude, frequency and/or duty cycle), so as to establish the current that results in the lowest blood pressure in the subject. In general, $p\_B$ represents a hypothetical lowest blood pressure achievable by a hypothetical perfect ablation of the nerve tissue of renal artery 8, that blocks all action potentials from propagating therealong.

FIG. 2C shows electrode units 22a and 22b initiating respective action potentials 50 and 52 (i.e., induced action potentials) in the nerve tissue of renal artery 8, by applying an excitatory current to the nerve tissue. As described hereinabove, for some applications, each electrode unit drives the excitatory current via electrode 30c. As also described hereinabove, the electrode units are typically configured to initiate unidirectional action potentials, and are oriented such that the unidirectional action potentials propagate toward the nerve tissue adjacent to ablation unit 24 and toward the other electrode unit. That is, (1) action potentials 50, initiated by electrode unit 22a are typically efferent, and propagate from unit 22, past ablation unit 24, and toward kidney 10, and (2) action potentials 52, initiated by electrode unit 22b are typically afferent, and propagate from unit 22, past ablation unit 24, and toward aorta 12 and the CNS of the subject.

It is hypothesized that, by contrast to the blocking of endogenous action potentials, initiation of action potentials 50 and 52 has similar effects to increased endogenous action potentials (e.g., to increase systemic blood pressure). For example, it is hypothesized that action potentials 50 induce kidney 10 to increase systemic blood pressure via the sympathetic pathway, and action potentials 52 induce the CNS to increase systemic blood pressure via the sympathetic pathway. It is further hypothesized that the magnitude of the effects of action potentials 50 and 52 may be greater than those of the endogenous action potentials, and/or that action potentials 50 and 52 are configurable to have such greater effects.

After the start of the application of the excitatory current (e.g., while the excitatory current is being applied, or after it has stopped being applied), sensor 26 detects a blood pressure p_C of the subject. For example, the blood pressure may be detected after a duration in which blood pressure is allowed to respond to the increase in renal nerve activity. The excitatory current may be calibrated in real-time (e.g., by adjusting amplitude, frequency and/or duty cycle), so as to establish the current that results in the highest blood pressure in the subject. For some applications, p_C represents a hypothetical highest blood pressure achievable by a high-level (e.g., hypothetical maximum) renal nerve activity (e.g., the highest blood pressure achievable by the body of the subject via renal nerve activity).

Although FIG. 2C shows two opposite-facing unidirectional electrode units, it is noted that for some applications, only one electrode unit is used, and for some applications, the electrode unit(s) are not unidirectional. For applications in which two electrode units are used, the operation of the electrode units may be temporally offset with respect to each other, so as to reduce interference therebetween. For example, although on a relatively large timescale, electrode unit 22a may initiate induced action potentials 50 at generally the same time as electrode unit 22b initiates induced action potentials 52, nevertheless, on a relatively small timescale, the action potentials are typically alternated (e.g., as indicated by action potentials 50 and 52 being labeled as being applied at "time=t" and "time=t+delta t", respectively).

It is to be noted that, although FIGS. 2A-H show sequential steps, the steps described with reference to FIGS. 2A-C may be performed in a different order (e.g., the step described with reference to FIG. 2C may be performed before the step described with reference to FIG. 2B).

FIG. 2D shows ablation unit 24 applying a first application of ablative energy 60 (e.g., ablating RF energy) to the nerve tissue of renal artery 8. It is desirable to ablate renal artery tissue to a degree that is sufficient to achieve a desired decrease of renal nerve activity, but not to a greater degree. The first application of ablative energy 60 is typically configured to be insufficient to ablate the nerve tissue to the desired degree (e.g., insufficient to completely ablate the nerve tissue). For example, first application 60 may be configured to be sufficient to fully ablate nerve tissue in less than 50% (e.g., less than 20%, such as less than 10%) of the general population. That is, first application 60 generates, in the wall of renal artery 8, a lesion 62 (e.g., a circumferential lesion) that is sufficient to completely block renal nerve activity in less than 50% (e.g., less than 20%, such as less than 10%) of the general population.

FIG. 2D does not show the non-ablative blocking current being applied by electrode units 22a and 22b during the application of the ablative energy by ablating unit 24. However, for some applications, the non-ablative blocking current is applied at this time. For some such applications, the application of the non-ablative blocking current during the application of the ablative energy reduces pain experienced by the subject, e.g., by inducing local paresthesia and/or anesthesia. The non-ablative blocking current that is used to induce this pain relief may have the same characteristics as, or different characteristics from, the non-ablative blocking current used to block endogenous signals in the nerve tissue being ablated. For some applications, a distinct electrode unit is used for application of the pain-relieving non-ablative blocking current. For some applications, another pain-relief method (e.g., providing an analgesic drug) is alternatively or additionally used.

Subsequent to first application 60, electrode units 22a and 22b again initiate induced action potentials 50 and 52, by again applying the excitatory current (FIG. 2E). Action potentials 50 and 52 are at least in part blocked from propagating past lesion 62 in the nerve tissue (illustrated by the portions of the arrows of the action potentials that are disposed past lesion 62 being broken). After the start of the application of the excitatory current (e.g., while the excitatory current is being applied, or after it has stopped being applied) sensor 26 detects a blood pressure p_D of the subject. For example, the blood pressure may be detected after a duration in which blood pressure is allowed to respond to action potentials 50 and 52. Detected blood pressure p_D may thereby represent a hypothetical highest blood pressure achievable by a high-level (e.g., hypothetical maximum) renal nerve activity, following first application of ablative energy 60 (e.g., a high-level (e.g., hypothetical maximum) renal nerve activity in the presence of lesion 62). Due to the reduced propagation of induced action potentials 50 and 52 caused by lesion 62, detected blood pressure p_D is typically lower than detected blood pressure p_C. Pressure p_D is typically greater than pressure p_B (e.g., due to the typical configuration of first application of ablative energy 60 to be typically insufficient to completely ablate the nerve tissue).

Subsequently, ablation unit 24 typically applies a second application of ablative energy 60' to the nerve tissue of renal artery 8, thereby increasing the degree of ablation of the lesion (now designated 62' (FIG. 2F)). Second application 60' may have the same characteristics (e.g., intensity) as first application 60, or may be different (e.g., may have a greater or lower intensity). For example, if sensor 26 determines that the reduction in systemic blood pressure due to first application of ablative energy 60 is significantly less than is desired, then second application of ablative energy 60' may be set to have a higher intensity than first application of ablative energy 60. Similarly, if sensor 26 determines that the reduction in systemic blood pressure due to first application of ablative energy 60 is close to a target level (e.g., a desired level), then second application of ablative energy 60' may be set to have an equal or lower intensity than first application of ablative energy 60. (In general, the intensity of applied energy may be varied using techniques known in the art, such as by varying amplitude, pulse width, frequency, duration of energy application, or duty cycle of energy application.)

Subsequent to second application of ablative energy 60', electrode units again initiate action potentials 50 and 52 by applying the excitatory current (FIG. 2G). Due to the increased ablation of the lesion, action potentials 50 and 52 are blocked from propagating past lesion 62', to a greater degree than they were from propagating past lesion 62 (illustrated by the broken portions of the arrows of the action potentials in FIG. 2G, being more broken than the same portions in FIG. 2G). After the start of the application of the excitatory current (e.g., while the excitatory current is being applied, or after it has stopped being applied) sensor 26 detects a blood pressure p_E of the subject. For example, the blood pressure may be detected after a duration in which blood pressure is allowed to respond to action potentials 50 and 52. Detected blood pressure p_D may thereby represent a hypothetical highest blood pressure achievable by a high-level (e.g., hypothetical maximum) renal nerve activity, following second application of ablative energy 60' (e.g., a high-level (e.g., hypothetical maximum) renal nerve activity in the presence of lesion 62'). Due to the further reduced propagation of induced action potentials 50 and 52 caused by lesion 62', detected blood pressure p_E is typically lower than detected blood pressure p_D.

The cycle of ablating nerve tissue, initiating action potentials, and detecting blood pressure (e.g., as described with reference to FIGS. 2D-E, and FIGS. 2F-G) may be repeated as necessary. FIG. 2H shows an example in which a further two such cycles have been performed, and respective detected blood pressures p_F and p_G have been obtained. Induced action potentials 50 and 52 are completely blocked from propagating past the lesion, which is now designated 62". It is to be noted that, for some applications and/or for some subjects, fewer or more cycles may be useful to achieve a desired degree of blocking (e.g., complete blocking). For example, for some subjects, only one application of ablation energy is applied.

Reference is again made to FIGS. 2A-H. For some applications, impedance between electrode units 22a and 22b is measured at each cycle, so as to further facilitate the determination of the achieved degree of ablation.

Reference is made to FIG. 3, which is a schematic illustration of some techniques for facilitating ablation of nerve tissue of the renal artery, in accordance with some applications of the invention. FIGS. 2A-H show a technique of using system 20 to repeatedly (e.g., cyclically) initiate induced action potentials in, and ablate, nerve tissue of the renal artery, and to repeatedly detect blood pressure of the subject (1) in the presence and absence of the induced action potentials, and (2) before and after the ablations. As described with reference to FIGS. 2A-H, this ablate-excite-detect cycle may be repeated as necessary to achieve a desired degree of ablation. FIG. 3 shows several techniques by which a suitable number of repetitions may be determined. Typically, this determination is performed after each detection of blood pressure subsequent to detection of blood pressure p_A. For illustrative purposes, FIG. 3 shows this determination being performed after four ablations and four respective blood pressure detections (p_D, p_E, p_F, and p_G).

For some applications, the ablate-excite-detect cycle is stopped at least in part responsively to the difference delta_1 between detected blood pressure p_G and detected blood pressure p_C. For example, difference delta_1 may be the difference between (1) the blood pressure detected after the most recent application of ablation energy, and (2) the highest blood pressure achievable by the high-level (e.g., hypothetical maximum) renal nerve activity.

For some applications, the ablate-excite-detect cycle is stopped at least in part responsively to the difference delta_2 between detected blood pressure p_G and detected blood pressure p_B. For example, difference delta_2 may be the difference between (1) the blood pressure detected after the most recent application of ablation energy, and (2) the hypothetical lowest blood pressure achievable by the hypothetical perfect ablation of the nerve tissue of the renal artery. For some such applications, the cycle is stopped at least in part responsively to a difference in magnitude between difference delta_1 and difference delta_2. For example, if delta_1 is significantly greater (e.g., more than a threshold magnitude greater) than delta_2, the cycle may be stopped because a threshold proportion of a hypothetical possible effect on blood pressure is deemed to have already been induced.

It is hypothesized that delta_1 and delta_2 are indicative of the cumulative effect of the ablations up to, and including, the most recent ablation, on the maximum possible contribution by renal nerve activity to blood pressure.

For some applications, the ablate-excite-detect cycle is stopped at least in part responsively to the difference delta_3 between detected blood pressure p_G and detected blood pressure p_F. For example, difference delta_3 may be the difference between (1) the blood pressure detected after the most recent application of ablation energy, and (2) the blood pressure detected after the immediately-prior application of ablation energy. For some such applications, the cycle is stopped at least in part responsively to the difference delta_4 between detected blood pressure p_D and detected blood pressure p_C. For example, difference delta_4 may be the difference between (1) the blood pressure detected after the first application of ablation energy, and (2) the blood pressure detected before the first application of ablation energy. For some such applications, the cycle is stopped at least in part responsively to a difference in magnitude between difference delta_3 and difference delta_4. For example, if delta_3 is significantly smaller (e.g., more than a threshold magnitude smaller) than delta_4, the cycle may be stopped because it is deemed that the most recent application of ablative energy (i.e., that which resulted in difference delta_4) was significantly less effective in reducing blood pressure than was the first application of ablative energy, and thereby further applications of ablative energy are also unlikely to be significantly effective.

It is hypothesized that delta_3 and delta_4 are indicative of the effect of the most recent ablation, and the first ablation, respectively, on the maximum possible contribution by renal nerve activity to blood pressure. It is thereby hypothesized that delta_4 alone, and when compared to delta_3, is indicative of the efficacy of the most recent application of ablation energy.

For some applications, at least in part responsively to one or more blood pressure detections, no ablation is performed. For example, if, in a given subject, a difference delta_5 between detected "untreated" blood pressure p_A and the hypothetical lowest blood pressure achievable by the hypothetical perfect ablation of the nerve tissue p_B, is lower than a threshold difference, it may be determined that renal nerve ablation is not an appropriate treatment for that subject. A similar determination may be made alternatively or additionally in response to (1) a difference delta_6 between blood pressure p_A and blood pressure p_C, and/or (2) a difference delta_7 between blood pressure p_C and blood pressure p_B. It is hypothesized that differences delta_5, delta_6, and/or delta_7 are indicative of the potential efficacy of renal nerve ablation on hypertension for the given subject, and thereby, at least in part responsively to these differences, patient selection may be performed. For example, a high value of delta_7 may be indicative of a relatively high sensitivity of blood pressure to renal nerve activity in the given subject, and therefore the given subject is more likely to be selected for renal nerve ablation.

It is to be noted that, for some applications, one or more of the blood pressure measurements described hereinabove may be omitted from the procedure. For example, if it is known in advance which of differences delta_1 through delta_7 are to be used to determine when to stop the ablate-excite-detect cycle, a measurement that is not to be used may be omitted. Typically, however, only a maximum of two of the pre-ablation blood pressures (e.g., p_A, p_B, and p_C) are omitted, and none of the post-ablation blood pressures (e.g., p_D, p_E, p_F, and p_G) are omitted. For some applications, the determination of when to stop the ablate-excite-detect cycle is based solely on the blood pressure achieved following the most recent ablation.

Reference is made to FIG. 4, which is a flow diagram, illustrating at least some steps in the techniques described with reference to FIGS. 2A-H and 3. Step 102 comprises detecting a preliminary value of a parameter indicative of blood pressure, e.g., as described with reference to FIG. 2A.

Step 104 comprises (1) blocking endogenous action potentials in the nerve by applying a non-ablative blocking current to the nerve and (2) after the start of the application of the non-ablative blocking current, detecting a value of the parameter (i.e., a "blocked" value), e.g., as described with reference to FIG. 2B. The "blocked" value may be greater or smaller than the preliminary value, depending on the parameter and nerve being ablated. For example, for applications in which the renal nerve is being ablated so as to treat hypertension, blocking of endogenous action potentials in the renal nerve typically reduces blood pressure. As also described with reference to FIG. 2B, a calibration step 106 is optionally performed, so as to establish the characteristics of the non-ablative blocking current that will have the greatest effect on the detected parameter.

Step 108 comprises (1) initiating action potentials in the nerve by applying an excitatory current to the nerve and (2) after the start of the application of the excitatory current, detecting a value of the parameter (i.e., an "excited" value), e.g., as described with reference to FIG. 2C. Similarly to the "blocked" value, the "excited" value may be greater or smaller than the preliminary value, depending on the parameter and nerve being ablated. As also described with reference to FIG. 2C, a calibration step 110 is optionally performed, so as to establish the characteristics of the non-ablative blocking current that will have the greatest effect on the detected parameter.

As described hereinabove, steps 102, 104, and 106 may be performed in a different order from that shown in FIG. 4. However, step 102 is typically performed subsequent to the delivery of the apparatus (e.g., system 20) into the subject, and prior to steps 104 and 106.

Step 112 comprises ablating the nerve tissue by applying ablative energy, e.g., as described with reference to FIG. 2D (and as subsequently described with reference to FIG. 2F). Subsequently, step 114 is performed, which comprises (1) initiating action potentials in the nerve by applying an excitatory current to the nerve and (2) after the start of the application of the excitatory current, detecting a value of the parameter, e.g., as described with reference to FIG. 2E. For some applications, step 114 is identical to step 108, except that the nerve tissue in which the action potentials are being initiated has been at least in part ablated. The value detected in step 114 is thereby an "ablated" value.

Subsequently, the "ablated" value is compared to at least one of: the preliminary value, the "blocked" value, and the "excited" value (step 116), and a decision 118 to continue ablating, or to stop, is made, e.g., as described with reference to FIG. 3. If it is decided to continue ablating, steps 112, 114, 116, and 118 are repeated, optionally after an adjustment step 120 in which one or more characteristics (e.g., the intensity) of the ablation energy is adjusted. This part of the technique thereby represents an iterative routine 122 (e.g., a cycle), which may comprise the ablate-excite-detect cycle described hereinabove (e.g., with reference to FIGS. 2A-H and 3).

For some applications, the initiation of action potentials and the ablation steps shown in FIG. 4 (e.g., within steps 108 and 114) may be performed using a single electrode unit. For example, a single electrode unit may be moved back and forth through a blood vessel, alternating between applying an excitatory current and applying ablative energy (e.g., an ablating RF current). The single electrode unit may also be used to perform the blocking of endogenous action potentials (e.g., within step 104), by applying a non-ablating blocking current.

Reference is again made to FIGS. 2A-4. System 20, and the techniques described herein, may be performed with varying degrees of automation, in accordance with various applications of the invention. For example:

System 20 may display the blood pressures detected by sensor 26 (e.g., on a display, in numerical and/or graphical format), such that an operating physician (or another healthcare provider) may determine when to stop the ablate-excite-detect cycle. For example, a graph similar to that shown in FIG. 4 may be displayed.

System 20, at least in part based on the detected blood pressures, may display an instruction or suggestion to the physician, as to whether to continue or stop the ablate-excite-detect cycle. Similarly, audio instructions/suggestions may be provided by system 20.

System 20 (e.g., control unit 32 thereof) may automatically control the electrode units and ablation unit, at least in part based on the detected blood pressures. For example, control unit 32 may receive, from sensor 26, information indicative of the detected blood pressures, and responsively control (e.g., stop) the ablate-excite-detect cycle.

Reference is again made to FIGS. 2A-4. For some applications of the invention, one or more drugs may be administered to the subject so as to modulate the blood pressure of the subject, in order to facilitate one or more of the steps described hereinabove. For example, a blood pressure-reducing drug may be administered to the subject throughout the entire procedure, so as to reduce all the detected values of blood pressure (e.g., p_A, p_B, etc., shown in FIG. 3). For some such applications, the differences between these detected values (e.g., delta_5, delta_6, etc., shown in FIG. 3) remain relatively constant (i.e., shift, but generally do not change in magnitude) as the detected values change. It is hypothesized that, for some such applications, administering such a blood pressure-reducing drug allows the determination of the hypothetical highest blood pressure achievable by a high-level (e.g., hypothetical maximum) renal nerve activity (e.g., p_C) without increasing the blood pressure of the subject to more than a desired (e.g., safe) threshold. Similarly, a blood pressure-increasing drug may be administered to increase the detected values of blood pressure, such as to allow the determination of the hypothetical lowest blood pressure achievable by a hypothetical perfect ablation of the nerve tissue (e.g., p_B, shown in FIG. 3), without reducing the blood pressure of the subject to below a desired (e.g., safe) threshold.

Reference is made to FIGS. 5A-B, which are schematic illustrations of systems for ablating nerve tissue of at least one renal artery of a subject, in accordance with some applications of the invention. For some applications, it is desirable to ablate nerve tissue of both renal arteries 8a and 8b of the subject. For example, it is hypothesized that, for some applications, it is advantageous to ablate the nerve tissue incompletely in both renal arteries (e.g., as opposed to completely ablating the nerve tissue in only one renal artery), so as to retain at least some nerve activity in each renal nerve, e.g., such that each kidney retains at least some blood pressure control. FIG. 5A shows a system 140, comprising two intravascular devices 21 (e.g., intravascular device 21a and intravascular device 21b), each comprising a respective ablation unit 24 (i.e., ablation unit 24a and ablation unit 24b), and a respective pair of electrode units 22

(i.e., one pair comprising electrode units 24a and 24b, and another pair comprising electrode units 24c and 24d). One intravascular device 21 (i.e., one ablation unit and one pair of electrode units) is disposed in each renal artery, and is configured to ablate a respective section of nerve tissue of the respective renal artery. For some applications (e.g., as shown in FIG. 5A for system 140) intravascular device 21b is identical to (i.e., separate from but identical to) intravascular device 21a. That is, the two distal portions of system 140 are separate from but identical to each other. For some applications (e.g., as shown in FIG. 5B for system 160), the two intravascular devices and/or the two distal portions of the system are not identical to each other.

For some applications of the invention, when initiating induced action potentials in nerve tissue of one renal artery, the endogenous action potentials in the nerve tissue of the other renal artery are blocked using the non-ablative blocking current, e.g., so as to reduce obfuscation of any effect seen. Alternatively, induced action potentials are initiated in the nerve tissue of both renal arteries (e.g., simultaneously). For some applications, it is desirable to perform this blocking and/or initiating in the nerve tissue of the other renal artery even when the nerve tissue of the other renal artery is not to be ablated. For some applications, the non-ablative blocking current is applied to nerve tissue of both renal arteries (i.e., bilaterally) at substantially the same time, e.g., so as to determine a lowest blood pressure achievable by a hypothetical perfect ablation of the nerve tissue of both renal arteries. For some applications, such a lowest blood pressure is used in place of, or in addition to, p_B, described with reference to FIGS. 2A-4. For some such applications, system 160 (shown in FIG. 5B), system 220 (described hereinbelow with reference to FIG. 6), system 320 (described hereinbelow with reference to FIG. 7), and/or system 420 (described hereinbelow with reference to FIG. 8) is used in place of system 160, mutatis mutandis. System 160 comprises a third electrode unit 162 (which may comprise electrode unit 22c), but typically does not comprise electrode unit 22d or ablating unit 24b. Systems 140 and 160 are typically used as described hereinabove for system 20, mutatis mutandis.

For some applications, catheter 28 of systems 140 and 160 has two distal portions thereof: longitudinal member first distal portion 28a, and longitudinal member second distal portion 28b. That is, for some applications, the distal portion of catheter 28 is bifurcated into distal portions 28a and 28b, each of the distal portions being configured to be advanced into a respective renal artery, as shown in FIGS. 5A-B.

Figure 6:
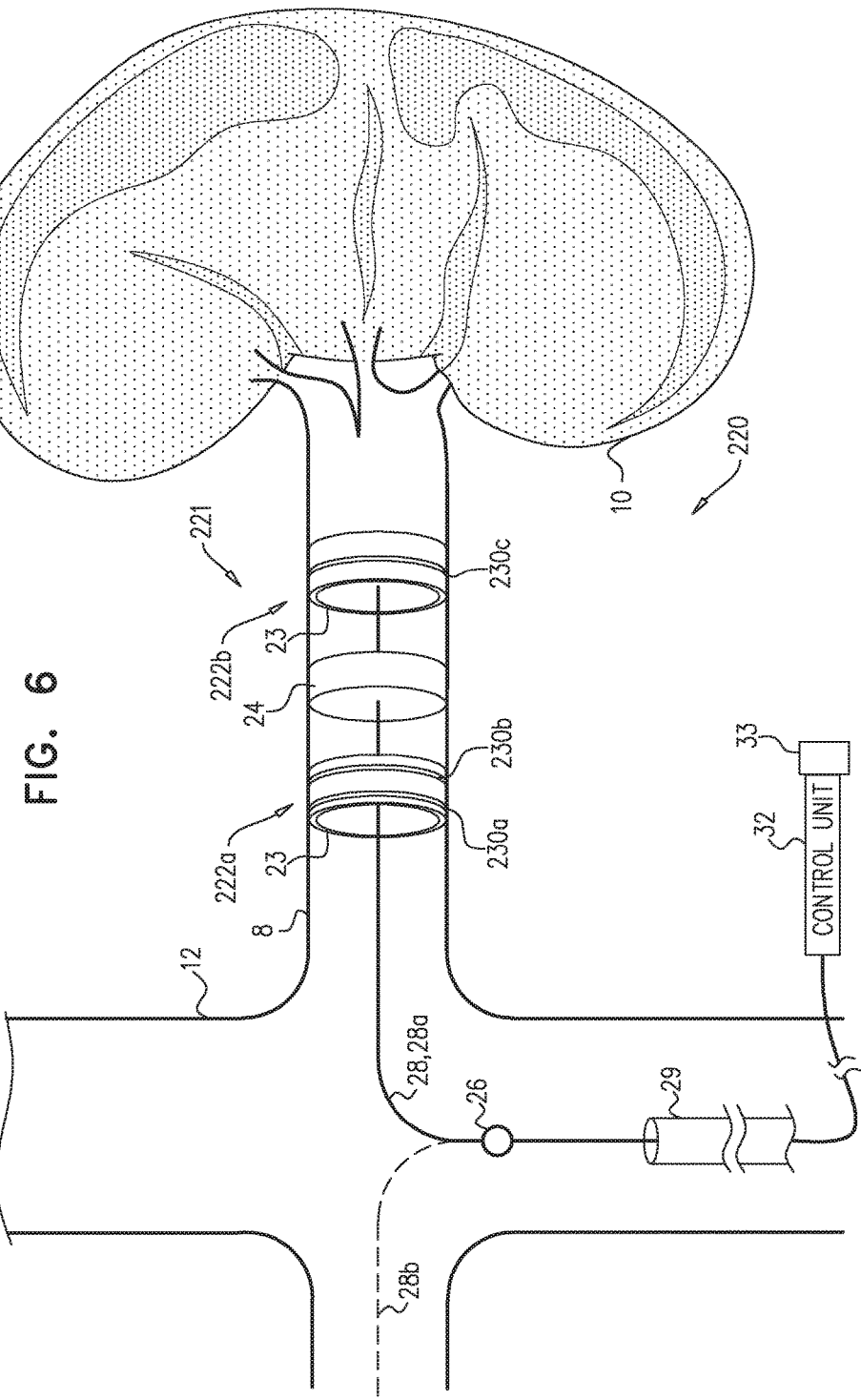

Reference is made to FIG. 6, which is a schematic illustration of a system 220 for ablating nerve tissue of a blood vessel of a subject, in accordance with some applications of the invention. System 220 is typically used in a similar manner to system 20 described hereinabove, mutatis mutandis, and elements of system 220 are typically identical to identically-named elements of system 20, except where otherwise described. For example, system 220 may be used in combination with the steps described with reference to FIG. 4, mutatis mutandis. System 220 comprises an intravascular device 221 that comprises a first electrode unit 222a and a second electrode unit 222b, and ablation unit 24 (described hereinabove) disposed therebetween. Although units 222a, 222b and 24 are shown as distinct elements, for some applications intravascular device 221 is an integral unit that comprises and/or defines units 222a, 222b and 24. For example, for applications in which ablation unit 24 comprises an RF ablation unit that comprises one or more electrodes, device 221 may define units 222a, 222b and 24 by comprising the electrodes of units 222a, 222b and 24 (e.g., device 221 may comprise a stent-like body and four electrodes, distributed along the length of the body).

Second electrode unit 222b is configured to initiate action potentials in a portion of the nerve tissue of the blood vessel that is adjacent to unit 222b. In contrast to electrode unit 22b of system 20, electrode unit 222b is typically not unidirectional, but instead typically initiates bidirectional action potentials. Furthermore, electrode unit 222b is typically not configured to block action potentials. For some applications, and as shown in FIG. 6, electrode unit 222b comprises a single electrode 230c, and another electrode (e.g., an electrode of electrode unit 222a, an electrode of ablation unit 24, or an extracorporeal electrode) may serve as the return electrode.

First electrode unit 222a is configured to block action potentials in a portion of the nerve tissue of the blood vessel that is adjacent to unit 222a, such as action potentials propagating past unit 222a. In contrast to electrode unit 22a of system 20, electrode unit 222a is typically not configured to induce action potentials. For some applications, and as shown in FIG. 6, electrode unit 222a comprises two electrodes 230a and 230b, and control unit 32 is configured to drive the non-ablative blocking current between electrodes 230a and 230b (e.g., the control unit may be configured to drive the non-ablative blocking current via electrode 230a, with electrode 230b serving as a return electrode for the non-ablative blocking current). Alternatively, electrode unit 222a may comprise only one electrode, and another electrode (e.g., an electrode of electrode unit 222b, an electrode of ablation unit 24, or an extracorporeal electrode) may serve as the return electrode.

As described hereinabove, system 20 (as described hereinabove with reference to FIGS. 1-2H) is configured to initiate (1) unidirectional action potentials that propagate past ablation unit 24 and toward the kidney, and independently (2) unidirectional action potentials that propagate past ablation unit 24 and toward the CNS. Because all the initiated unidirectional action potentials must propagate past ablation unit 24, they must propagate through the portion of the nerve tissue that is subjected to ablation, and therefore the resulting increase in systemic blood pressure is indicative of the degree of ablation of that portion of the nerve tissue.

It will be observed that system 220 typically comprises fewer electrodes than does system 20. That is, system 220 is typically simpler than system 20. It will further be observed that, because action potentials induced by electrode unit 222b are not unidirectional, they also typically propagate toward kidney 10 without passing through the portion of the nerve tissue that is subjected to ablation. It has been noted by the inventors that the effect on systemic blood pressure resulting from stimulation of the CNS is more immediate than that resulting from stimulation of the kidney. It is hypothesized that similar techniques to those described hereinabove as performed with system 20 may be performed using system 220 because, although some initiated action potentials propagate toward the kidney without passing though the portion of the nerve tissue that is subjected to ablation, the detection of systemic blood pressure during the "excite & detect" steps described hereinabove (e.g., with reference to FIGS. 2A-4) typically involves detection of the more immediate changes caused by CNS stimulation, rather than the slower effects caused by kidney stimulation. For some applications, detection of a particular pattern of changes in parameters of the subject (e.g., heart rate and blood pressure) may be used to identify and/or distinguish effects caused by action potentials initiated by system 220.

For some applications, system 220 comprises a single intravascular device 221. For some applications, system 220 comprises two intravascular devices 221, each intravascular device being configured to be placed in a respective renal artery, in a manner similar to that described with reference to FIG. 5A for system 140, mutatis mutandis. FIG. 6 illustrates the option of system 220 comprising two intravascular devices, by showing in phantom second distal portion 28b of catheter 28, described hereinabove with reference to FIGS. 5A-B, to which a second intravascular device would be coupled.

Reference is made to FIG. 7, which is a schematic illustration of a system 320 for ablating nerve tissue of a blood vessel of a subject, in accordance with some applications of the invention. System 320 is typically used in a similar manner to systems 20 and 220 described hereinabove, mutatis mutandis, and elements of system 320 are typically identical to identically-named elements of system 20, except where otherwise described. For example, system 320 may be used in combination with the steps described with reference to FIG. 4, mutatis mutandis.

System 320 comprises an intravascular device 321 that comprises (1) a first electrode unit 322a comprising an electrode 330a, (2) a second electrode unit 322b comprising an electrode 330b, and ablation unit 24 (described hereinabove) disposed therebetween. Although units 322a, 322b and 24 are shown as distinct elements, for some applications intravascular device 321 is an integral unit that comprises and/or defines units 322a, 322b and 24, e.g., as described hereinabove for device 221, mutatis mutandis.

As described hereinabove, electrode unit 222a of system 220 may comprise only one electrode. For some applications, system 230 comprises or is an embodiment of system 220 when electrode unit 222a of system 220 comprises only one electrode.

For some applications, control unit 32 is configured to drive the excitatory current via electrode 330b, with another electrode (e.g., an electrode of ablation unit 24, electrode 330a, and/or an extracorporeal electrode) serving as a return electrode for the excitatory current. For some applications, control unit 32 is configured to drive the non-ablative blocking current via electrode 330a, with another electrode (e.g., an electrode of ablation unit 24, electrode 330b, and/or an extracorporeal electrode) serving as a return electrode for the non-ablative blocking current. For some applications in which ablation unit 24 comprises an RF ablation unit, electrode 330a, electrode 330b, and/or an extracorporeal electrode may serve as return electrodes for the ablating RF energy (i.e., RF current).

For some applications, system 320 comprises a single intravascular device 321. For some applications, system 320 comprises two intravascular devices 321, each intravascular device being configured to be placed in a respective renal artery, in a manner similar to that described with reference to FIG. 5A for system 140, mutatis mutandis. FIG. 7 illustrates the option of system 320 comprising two intravascular devices, by showing in phantom second distal portion 28b of catheter 28, described hereinabove with reference to FIGS. 5A-B, to which a second intravascular device would be coupled.

Reference is made to FIG. 8, which is a schematic illustration of a system 420 for ablating nerve tissue of a blood vessel of a subject, in accordance with some applications of the invention. System 420 is typically used in a similar manner to systems 20, 220 and 320 described hereinabove, mutatis mutandis, and elements of system 420 are typically identical to identically-named elements of system 20, except where otherwise described. For example, system 420 may be used in combination with the steps described with reference to FIG. 4, mutatis mutandis.

System 420 comprises an intravascular device 421 that comprises (1) an electrode unit 422 comprising an electrode 430, and (2) ablation unit 24 (described hereinabove). Although units 422 and 24 are shown as distinct elements, for some applications intravascular device 421 is an integral unit that comprises and/or defines units 422a and 24, e.g., as described hereinabove for devices 221 and 321, mutatis mutandis.

For some applications, control unit 32 is configured to drive the excitatory current via electrode 430, with another electrode (e.g., an electrode of ablation unit 24, and/or an extracorporeal electrode) serving as a return electrode for the excitatory current. For some applications, control unit 32 is configured to also drive the non-ablative blocking current via electrode 430, with another electrode (e.g., an electrode of ablation unit 24, and/or an extracorporeal electrode) serving as a return electrode for the non-ablative blocking current. For applications in which ablation unit 24 comprises an RF ablation unit, control unit 32 may alternatively be configured to drive the non-ablative blocking current via an electrode of the RF ablation unit, with electrode 430 and/or an extracorporeal electrode serving as a return electrode for the non-ablative blocking current. For some applications in which ablation unit 24 comprises an RF ablation unit, electrode 430 and/or an extracorporeal electrode may serve as return electrodes for the ablating RF energy (i.e., RF current).

For some applications, system 420 comprises a single intravascular device 421. For some applications, system 420 comprises two intravascular devices 421, each intravascular device being configured to be placed in a respective renal artery, in a manner similar to that described with reference to FIG. 5A for system 140, mutatis mutandis. FIG. 8 illustrates the option of system 420 comprising two intravascular devices, by showing in phantom second distal portion 28b of catheter 28, described hereinabove with reference to FIGS. 5A-B, to which a second intravascular device would be coupled.

Reference is again made to FIGS. 6-8. It is to be noted that in systems 220, 320 and 420, action potentials are initiated on the side of ablation unit 24 that is closer to kidney 10, such that the action potentials must propagate past the ablation unit (i.e., through the portion of the nerve tissue that is subject to ablation) before reaching the CNS, and therefore effects (e.g., on systemic blood pressure) induced by the CNS in response to the initiated action potentials are indicative of the degree of ablation of that portion of the nerve tissue.

Reference is made to FIGS. 9A-B, which are schematic illustrations of electrodes for use with the present invention, in accordance with some applications of the invention. FIG. 9A shows an electrode 240, which comprises a generally circular electrode that is placeable against (or close to) the inner wall of renal artery 8 such that the electrode traces the inner wall of the artery, e.g., forming a complete circle. For some applications, electrode 240 comprises a "lasso"-type electrode that almost forms a complete circle. FIG. 9B shows an electrode 242, which comprises a plurality of sub-electrodes 244 that are placeable against (or close to) the inner wall of renal artery 8. Electrode 242 traces the inner wall of artery 8 generally in an arc (e.g., a generally 360 degree arc (i.e., a complete circle)) but with small gaps between sub-electrodes 244 (e.g., electrode 242 forms a broken arc, e.g., a broken ring). Typically, sub-electrodes 244 are configured to be driven simultaneously, but at least partly independently of each other (e.g., the sub-electrodes are independently addressable by the control unit), and are further typically configured (e.g., electrically coupled to a control unit, such as control unit 32) such that current is balanced (e.g., spread evenly) among the sub-electrodes, e.g., via separate wires leading from the control unit. It is hypothesized that for some applications, the use of electrode 242 comprising sub-electrodes 244 advantageously reduces variances in the distribution of current around the circumference of artery 8 that may otherwise be caused by variances in conductivity of tissue around the circumference.

For some applications, one or more of the electrodes described hereinabove may comprise electrode 242. For example, electrodes of an electrode unit (for application of blocking and/or excitatory current) and/or, for applications in which ablation unit 24 comprises an RF ablation unit, the ablating electrode of the ablation unit may comprise electrode 242.

Reference is made to FIG. 10, which is a flow diagram, illustrating at least some steps in ablating nerve tissue of renal artery 8 of the subject, in accordance with some applications of the invention. For some applications, it is desirable to ablate the nerve tissue incompletely, e.g., to a known degree. For such applications, blood pressure may be used as an indicator of such ablation. The steps shown in FIG. 10 are described herein as being performed using system 420, described with reference to FIG. 8, but it is to be noted that the steps may alternatively be performed using other apparatus, such as other systems described herein, mutatis mutandis.

A preliminary value of blood pressure (e.g., at rest) of the subject is detected 502, e.g., using sensor 26. A detected excited blood pressure value is determined 504 by applying an excitatory current (e.g., using electrode 430) that induces action potentials in the renal nerve, and detecting a detected excited blood pressure value after the start of the application of the excitatory current (e.g., while the excitatory current is being applied, or after it has stopped being applied). For example, the blood pressure may be detected after a duration in which blood pressure is allowed to respond to the increase in renal nerve activity.

The detected excited blood pressure value is compared 506 (e.g., by control unit 32) with a target excited blood pressure value (described hereinbelow with reference to step 508). If the detected excited blood pressure value does not cross a threshold defined at least in part based on the target excited blood pressure value, the value of at least one property (such as, but not limited to, frequency or amplitude) of the excitatory current is altered 510, and the detected excited blood pressure value is determined again 504, until the detected excited blood pressure value does cross the threshold defined at least in part based on the target excited blood pressure value. This iterative routine is indicated by box 512. For some applications, this iterative routine is automatically performed by control unit 32. For example, the operating physician (or another healthcare provider) may press a single button on control unit 32, and the control unit iteratively (1) applies 504 the excitatory current and detects 504 the detected excited blood pressure value, (2) compares 506 the detected excited blood pressure value to the target excited blood pressure value, and (3) alters the value of the at least one property of the excitatory current, until the detected excited blood pressure value crosses the threshold defined at least in part based on the target excited blood pressure value.

It is to be noted that throughout this patent application, including the specification and the claims, a "threshold defined at least in part based on" a given value may be:
equal to the given value (e.g., with reference to the above paragraph, the detected excited blood pressure value crosses the threshold by becoming equal to or greater than the target excited blood pressure value), or
different from the given value by a fixed value, by a fixed multiple of the given value, and/or by a linear or non-linear function determined at least in part based on the given value (e.g., with reference to the above paragraph, the detected excited blood pressure value crosses the threshold by becoming equal to or greater than a value that is different from the target excited blood pressure value by a fixed value, by a fixed multiple of the target excited blood pressure value, and/or by a linear or non-linear function determined at least in part based on the target excited blood pressure value).

For some applications, the target excited blood pressure value is provided 508 (e.g., generated) by control unit 32 at least in part responsively to the preliminary blood pressure value. For example, control unit 32 may set the target excited blood pressure value to be a given amount or percentage greater than the preliminary blood pressure value. Alternatively, the target excited blood pressure value may be provided 508 manually, such as by the operating physician (or another healthcare provider) entering the target excited blood pressure value into control unit 32.

Once the detected excited blood pressure value crosses the threshold defined at least in part based on the target excited blood pressure value, ablating energy is applied 514 (e.g., using ablation unit 24) to the nerve tissue of renal artery 8.

Subsequently, action potentials are again induced 516 in the nerve tissue by applying (e.g., using electrode 430) a selected excitatory current (e.g., a characteristic thereof) that is at least in part based on the excitatory current at which the detected excited blood pressure value crossed threshold defined at least in part based on the target excited blood pressure value (in step 506). For example, the value of at least one characteristic (e.g., frequency and/or amplitude) of the selected excitatory current may be equal to the value of the same property of the excitatory current at which the detected excited blood pressure value crossed the threshold (e.g., the excitatory current that induced the detected excited blood pressure value to cross the threshold) is "selected" (e.g., by control unit 32) as the selected excitatory current. For some applications, the selected excitatory current may be identical to the excitatory current at which the detected excited blood pressure value crossed the threshold defined at least in part by the target excited blood pressure value.

A detected ablated blood pressure value is detected 516 (e.g., by sensor 26) after the start of the application of the selected excitatory current (e.g., while the selected excitatory current is being applied, or after it has stopped being applied). For example, the blood pressure may be detected after a duration in which blood pressure is allowed to respond to the increase in renal nerve activity.

The detected ablated blood pressure value is compared 518 (e.g., by control unit 32) with a target ablated blood pressure value (described hereinbelow with reference to step 520). If the detected ablated blood pressure value does not cross a threshold defined at least in part based on the target ablated blood pressure value, ablation energy is applied again 514, and the detected ablated blood pressure value is determined again 516 until the detected ablated blood pressure value does cross the threshold defined at least in part based on the target ablated blood pressure value. This iterative routine is indicated by box 522. For some applications, this iterative routine is automatically performed by control unit 32. For example, the operating physician (or another healthcare provider) may press a single button on control unit 32, and the control unit iteratively (1) applies 514 the ablation energy, (2) applies 516 the selected excitatory current and detects 516 the detected ablated excited blood pressure value, and (3) compares 518 the detected ablated blood pressure value to the target ablated blood pressure value, until the detected ablated blood pressure value crosses the threshold defined at least in part based on the target ablated blood pressure value.

It is to be noted that the threshold defined at least in part based on the target ablated blood pressure value may be:
  equal to the target ablated blood pressure value (e.g., the detected ablated blood pressure value crosses the threshold by becoming equal to or lower than the target ablated blood pressure value), or
  different from the target ablated blood pressure value by a fixed value, by a fixed multiple of the target ablated blood pressure value, and/or by a linear or non-linear function determined at least in part based on the target ablated blood pressure value (e.g., the detected ablated blood pressure value crosses the threshold by becoming equal to or lower than a value that is different from the target ablated blood pressure value by a fixed value, by a fixed multiple of the target ablated blood pressure value, and/or by a linear or non-linear function determined at least in part based on the target ablated blood pressure value).

For some applications, during each iteration, the ablation energy retains the same characteristics (e.g., control unit 32 drives ablation unit 24 to apply ablation energy having the same characteristics). For some applications, a characteristic of the ablation energy is altered 524 (e.g., by control unit 32) prior to each subsequent application of the ablation energy. For example, the intensity of the ablation energy may be increased or decreased by control unit 32.

For some applications, the target ablated blood pressure value is provided 520 (e.g., generated) by control unit 32 at least in part responsively to (1) the preliminary blood pressure value (as described with reference to step 502), and (2) the target excited blood pressure value and/or the detected excited blood pressure value (as described with reference to steps 506 and 508), and optionally at least in part responsively to a target level (e.g., a desired level) of ablation which may be provided 526 to the control unit. For example, an operating physician (or another healthcare provider) may input into control unit 32 (e.g., via an interface 33 thereof, such as a dial or a keypad) the target degree of ablation (e.g., based on one or more parameters of the subject and/or the condition being treated), and the control unit calculates, at least in part responsively to (1) the preliminary blood pressure value, and (2) the target excited blood pressure value and/or the detected excited blood pressure value, the target ablated blood pressure value that corresponds to the target degree of ablation. Purely for illustrative purposes, for example, if the target degree of ablation is 50%, the target ablated blood pressure value may be calculated as being midway between (1) the preliminary blood pressure value, and (2) the target excited blood pressure value and/or the detected excited blood pressure value. The target ablated blood pressure value may alternatively be provided 520 manually, such as by the operating physician (or another healthcare provider) entering the target ablated blood pressure value into control unit 32.

Reference is made to FIG. 11, which is a flow diagram illustrating automation of at least some of the steps described with reference to FIG. 10, in accordance with some applications of the invention. As described with reference to FIG. 10, for some applications, generation of target excited blood pressure values and/or ablated blood pressure values is performed by control unit 32. Similarly, for some applications, iterative step 512 and/or iterative step 522 is performed (e.g., automatically) by control unit 32. FIG. 11 illustrates, for some applications of the invention, which steps are performed (e.g., manually) by the operating physician (or another healthcare provider), and which steps are performed (e.g., automatically) by control unit 32.

The operating physician percutaneously advances 540 the intravascular device (e.g., intravascular device 421 of system 420) into renal artery 8 of the subject, inputs 526 the target degree of ablation into control unit 32 (e.g., via an interface thereof), and activates the control unit. It is to be noted that steps 540 and 526 may alternatively be performed in reverse order, and that another healthcare provider may perform step 526. Subsequently, control unit 32 automatically performs the steps indicated by box 542, and indicates that the procedure (e.g., the ablation procedure) is complete, at which point the operating physician withdraws 544 the intravascular device from the subject. The steps contained by box 542 are described with reference to FIG. 10, using the same reference numerals. It is to be noted that step 512 of FIG. 11 corresponds to box 512 of FIG. 10, which contains steps 504, 506 and 510, and that step 522 of FIG. 11 corresponds to box 522 of FIG. 10, which contains steps 514, 516, 518 and 524.

Although the techniques described with reference to FIGS. 10-11 are generally described as being performed using system 420 (which is described with reference to FIG. 8), it is to be noted that the techniques may alternatively be performed using other apparatus, such as other systems described herein, mutatis mutandis. For example, the techniques described with reference to FIGS. 10-11 may be performed using system 20, system 140, system 160, system 220, or system 320, mutatis mutandis.

Reference is again made to FIGS. 1-11. The techniques described hereinabove utilize blood pressure (typically during application of the excitatory current) as an indicator of ablation of nerve tissue of the renal artery. The resulting controlled ablation of this nerve tissue is useful in treating hypertension, including mild hypertension in subjects for whom full renal nerve ablation is not necessary, and hypertension in subjects who also suffer from renal failure for whom full renal nerve ablation may be deleterious. It is to be noted, however, that these techniques may also be used to facilitate controlled ablation of this nerve tissue for treating other conditions, such as congestive heart failure, sleep apnea, and decreased insulin sensitivity in diabetic subjects. That is, blood pressure can be used to indicate and/or control a degree of ablation of nerve tissue of the renal artery even in subjects without hypertension and/or not being treated for hypertension.

Figure 12:
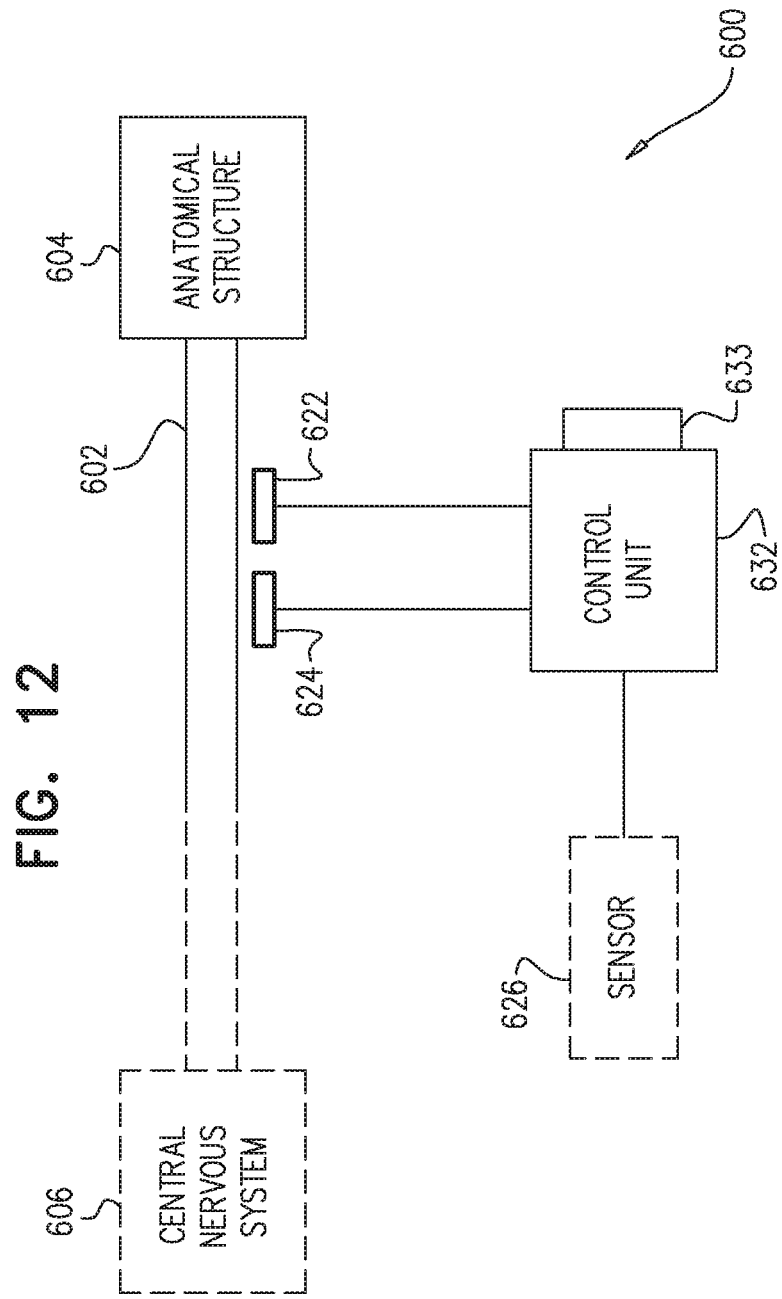
FIG. 12 is a schematic illustration of a system and techniques for use thereof, for controlled ablation of nerve tissue of a subject, in accordance with some applications of the invention.
Figure 13:
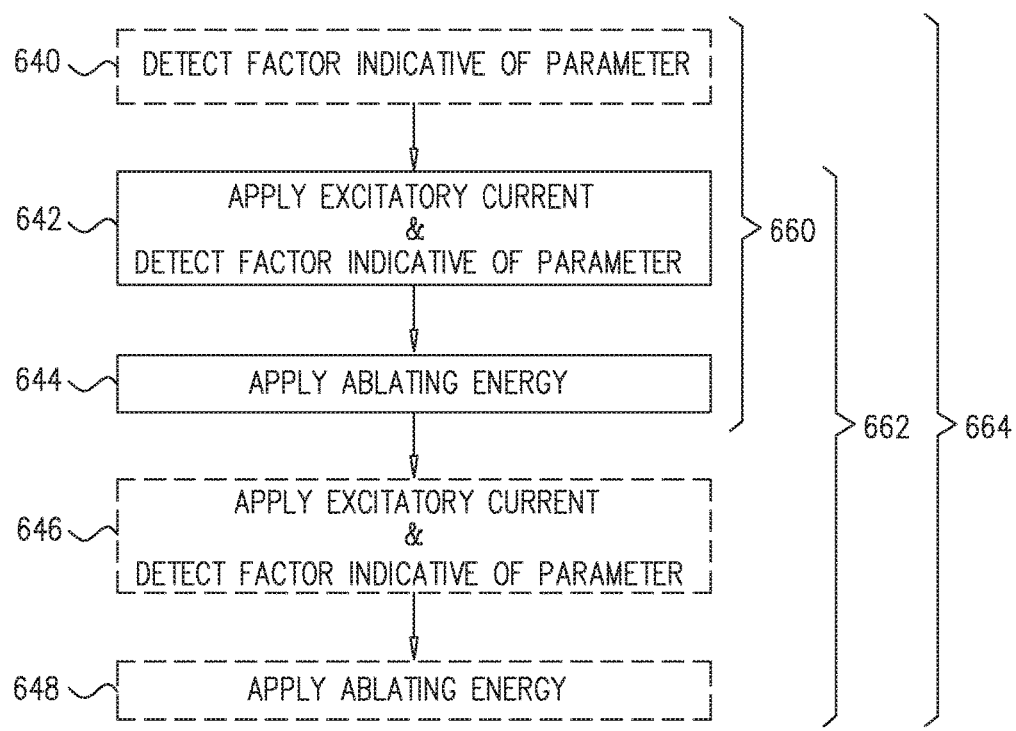
FIG. 13 is a flow chart showing at least some steps in one or more techniques for use with the system of FIG. 12, in accordance with some applications of the invention.

Reference is made to FIGS. 12-13, which are schematic illustrations of a system 600 and techniques for use thereof, for controlled ablation of nerve tissue 602 of a subject, in accordance with some applications of the invention. FIG. 12 is a schematic illustration of system 600, in accordance with some applications of the invention. Nerve tissue 602 typically directly or indirectly innervates an anatomical structure 604 of a subject (e.g., carries action potentials to and/or from the anatomical structure). For some applications, nerve tissue 602 carries action potentials between anatomical structure 604 and a central nervous system 606 of the subject. Typically, the action potentials are capable of altering a parameter of the subject, and thereby anatomical structure 604 is typically capable of altering the parameter of the subject. For some applications, nerve tissue 602 comprises a postganglionic neuron of the subject.

System 600 comprises at least one electrode unit 622, an ablation unit 624, and a control unit 632, configured to drive and/or control the electrode unit and/or the ablation unit. For some applications, control unit 632 comprises an interface 633. Typically, system 600 further comprises a sensor 626, configured to detect a factor indicative of the parameter of the subject. For some applications, system 600 does not comprise a sensor, and the parameter is detected by a sensor that is not a component of system 600, and/or is detected by a medical professional. For such applications, information relating to the factor (e.g., a value of the factor) may be inputted manually or automatically via interface 633.

Electrode unit 622 and ablation unit 624 are advanced to a vicinity of nerve tissue 602, e.g., to within 1 cm of the nerve tissue (e.g., within 1 mm of the nerve tissue, such as to be in contact with the nerve tissue). For some applications, nerve tissue 602 comprises nerve tissue associated with a blood vessel of the subject, and electrode unit 622 and ablation unit 624 are advanced toward the nerve tissue via the blood vessel, typically remaining within the blood vessel for the duration of the procedure (e.g., as described hereinabove with reference to FIGS. 1-11, mutatis mutandis). It is to be noted that although FIG. 12 shows electrode unit 622 disposed closer to anatomical structure 604 than is ablation unit 624, for some applications the electrode unit is disposed further from the anatomical structure than is the ablation unit. For some applications, electrode unit 622, ablation unit 624, control unit 632 and/or sensor 626 of system 600 comprise a respective identically-named corresponding component of one or more other systems described hereinabove. For some applications, electrode unit 622, ablation unit 624, control unit 632 and sensor 626 of system 600 are arranged (e.g., coupled to each other) as described for identically-named corresponding components of one or more other systems described hereinabove. For example, electrode unit 622, ablation unit 624, control unit 632 and sensor 626 may be coupled to and disposed along a longitudinal member, such as catheter 28 (not shown in FIG. 12).

FIG. 13 is a flow chart showing at least some steps in one or more techniques for use with system 600, in accordance with some applications of the invention. Action potentials are initiated in a first portion of nerve tissue 602 by electrode unit 622 applying an excitatory current to the first portion of the nerve tissue (step 642). The excitatory current typically has a frequency of greater than 1 Hz and/or less than 100 Hz, such as between 1 and 100 Hz, e.g., between 10 and 100 Hz. After a start of the application of the excitatory current, a detection of the factor indicative of the parameter of the subject is performed, e.g., using sensor 626 (step 642). For some applications, the detection is performed during the application of the excitatory current. For some applications, the detection is performed after the excitatory current has stopped being applied.

At least in part in response to the detection of the factor, ablating energy is applied to a second portion of nerve tissue 602 by ablation unit 624 (step 644). For some applications, ablation unit 624 comprises an RF ablation unit, and applies an RF current having a frequency of above 5 kHz and/or below 1 GHz, such as between 5 kHz and 1 GHz (e.g., 10 kHz-10 MHz, e.g., 50 kHz-1 MHz, e.g., 300 kHz-1 MHz, e.g., 300 kHz-500 kHz). As described hereinabove for ablation unit 24, mutatis mutandis, ablation unit 624 may alternatively or additionally be configured to ablate nerve tissue 602 using ultrasound energy, laser energy, resistive heating, cryogenically, using chemical ablation, or via another ablation mechanism.

For some applications, before application of the excitatory current in step 642, a detection of the factor is performed (e.g., while the subject is at rest and/or untreated) (step 640). Reference numeral 660 indicates a technique in which a first detection is performed before application of the excitatory current, a second detection of the factor is performed after the start of the application of the excitatory current, and subsequently ablating energy is applied. For some applications of technique 660, ablating energy is applied 644 at least in part responsively to the detection in step 640 and at least in part responsively to the detection in step 642. For example, ablating energy may be applied in response to a comparison of the first detection and the second detection, e.g., in response to a difference between a first detected value of the factor and a second detected value of the factor. For example, technique 660 may be used to screen subjects likely to be responsive to a treatment comprising ablation of nerve tissue 602 (e.g., by determining a sensitivity of the parameter to action potentials in nerve tissue 602).

For some applications, subsequent to the application of ablating energy in step 644, another application of excitatory current and detection of the factor are performed (step 646). Typically, step 646 is identical in nature to step 642. For such applications, at least in part in response to the detection in step 646 (and typically also at least in part in response to previous detection(s) of the factor), ablating energy is applied to a second portion of nerve tissue 602 by ablation unit 624 (step 648). Reference numeral 662 indicates a technique in which steps 646 and 648 are performed after step 644. Ablating energy of step 648 may be applied in response to a difference between a value of the factor detected in step 646 and a value of the factor detected in step 642. For example, this difference may indicate a degree of ablation achieved by the application of ablating energy, as described hereinabove.

Reference numeral 664 indicates a technique in which, in addition, step 640 is performed before step 642. For such a technique, ablating energy may be applied in response to one or more differences between respective values of the factor detected in steps 640, 642, and 646.

For some applications, the techniques described with reference to FIGS. 12-13 may be combined with those described hereinabove, and one or more steps described with reference to FIGS. 12-13 may comprise, or correspond to, steps or values described hereinabove with reference to other figures. For example:

The detection of the factor in step 640 may comprise, or correspond to:
- detecting value p_A described with reference to FIGS. 2A-3, mutatis mutandis;
- step 102 described with reference to FIG. 4, mutatis mutandis; and/or
- step 502 described with reference to FIG. 5, mutatis mutandis.

The detection of the factor in step 642 may comprise, or correspond to:
- detecting value p_C described with reference to FIGS. 2A-3, mutatis mutandis;

step 114 described with reference to FIG. 4, mutatis mutandis; and/or step 516 described with reference to FIG. 5, mutatis mutandis.

The application of ablating energy in step 644 may comprise, or correspond to:

the application of ablating energy between the detection of value p_C and the detection of value p_D, described with reference to FIGS. 2A-3, mutatis mutandis;

step 112 described with reference to FIG. 4, mutatis mutandis; and/or step 514 described with reference to FIG. 5, mutatis mutandis.

A difference between a value detected in step 640 and a value detected in step 642 may comprise, or correspond to, difference delta_6, described with reference to FIGS. 2A-3.

A difference between a value detected in step 642 and a value detected in step 646 may comprise, or correspond to, difference delta_4, described with reference to FIGS. 2A-3.

For some applications, steps 644, 646, and 648 represent an iterative routine in which ablative energy is repeatedly applied until a desired detection of the factor is achieved (e.g., until a threshold defined at least in part based on a target ablated value of the factor is crossed). For some applications, this iterative routine comprises, or corresponds to, iterative routine 122 described with reference to FIG. 4, and/or the iterative routine indicated by box 522 described with reference to FIG. 10, mutatis mutandis.

For some applications, step 642 comprises, or represents, an iterative routine in which the excitatory current is applied and adjusted until a desired detection of the factor is achieved (e.g., until a threshold defined at least in part based on a target excited value of the factor is crossed). For some applications, this iterative routine comprises, or corresponds to, steps 108 and 110 described with reference to FIG. 4, and/or the iterative routine indicated by box 512 described with reference to FIG. 10, mutatis mutandis.

For some applications, FIGS. 12-13 and the descriptions thereof are a generalized representation of techniques described with reference to earlier figures. Furthermore, the techniques described with reference to FIGS. 12-13 may be used with subjects suffering from conditions other than hypertension, and/or for ablation of nerve tissue other than that of the renal artery. Typically, the techniques described with reference to FIGS. 12-13 are used to facilitate controlled ablation of autonomic nerve tissue (e.g., tissue of an autonomic nerve) of a subject.

For some applications, the techniques described with reference to FIGS. 12-13 are used to treat a subject who suffers from overactivity of the sympathetic nervous system and/or underactivity of the parasympathetic nervous system (e.g. excess activity of the sympathetic nervous system compared to that of the parasympathetic nervous system). For example, nerve tissue 602 may comprise a sympathetic nerve of the subject.

For some applications, the techniques described with reference to FIGS. 12-13 are used to treat a subject who suffers from overactivity of the parasympathetic nervous system and/or underactivity of the sympathetic nervous system (e.g. excess activity of the parasympathetic nervous system compared to that of the sympathetic nervous system). For example, nerve tissue 602 may comprise a parasympathetic nerve of the subject.

For some applications, the techniques described with reference to FIGS. 12-13 are used to treat a subject who suffers from hypertension. For example, anatomical structure 604 may comprise a kidney of the subject, and/or nerve tissue 602 may comprise nerve tissue of the renal artery of the subject, e.g., as described hereinabove with reference to FIGS. 1-11, mutatis mutandis. Alternatively, anatomical structure 604 may comprise a carotid body of the subject, and/or nerve tissue 602 may comprise a glossopharyngeal nerve of the subject and/or a branch thereof that innervates the carotid body (e.g., the Nerve of Hering). For some such applications, detecting the factor indicative of the parameter of the subject comprises detecting blood pressure of the subject (e.g., sensor 626 may comprise a blood pressure sensor), e.g., as described hereinabove with reference to FIGS. 1-11, mutatis mutandis. Alternatively or additionally, ablating nerve tissue of the renal artery may be performed to treat a condition other than hypertension, e.g., as described hereinabove.

For some applications, the techniques described with reference to FIGS. 12-13 are used to treat a subject who suffers from premature ejaculation. For example, anatomical structure 604 may comprise the scrotum and/or the penis of the subject, and/or nerve tissue 602 may comprise the dorsal nerve, the pudendal nerve, and/or a sacral nerve of the subject. For some such applications, detecting the factor indicative of the parameter of the subject comprises detecting an ejaculation of the subject. For some such applications, detecting the factor indicative of the parameter of the subject comprises detecting an electromyographic (EMG) value (e.g., sensor 626 may comprise an EMG sensor comprising EMG electrodes). For example, EMG may be performed on a perineal muscle of the subject.

For some applications, the techniques described with reference to FIGS. 12-13 are used to treat a subject who suffers from erectile dysfunction. For example, anatomical structure 604 may comprise the penis of the subject, and/or nerve tissue 602 may comprise the dorsal nerve of the subject. For some such applications, detecting the factor indicative of the parameter of the subject comprises detecting blood pressure in the corpus cavernosum penis of the subject (e.g., sensor 626 may comprise a blood pressure sensor). For some such applications, detecting the factor indicative of the parameter of the subject comprises detecting an EMG value, such as of tissue of the penis of the subject. For some applications, controlled stimulation of the penis is performed to facilitate the detection.

For some applications, the techniques described with reference to FIGS. 12-13 are used to treat a subject who suffers from overactive bladder (e.g., urge incontinence). For example, anatomical structure 604 may comprise the bladder of the subject, and/or nerve tissue 602 may comprise a hypogastric nerve of the subject or a sacral nerve of the subject. For some such applications, detecting the factor indicative of the parameter of the subject comprises detecting urinary urgency (e.g., the subject may provide feedback). For some such applications, detecting the factor indicative of the parameter of the subject comprises detecting pressure in the bladder of the subject (e.g., sensor 626 may comprise a pressure sensor). For some such applications, detecting the factor indicative of the parameter of the subject comprises detecting an EMG value, such as of the bladder of the subject.

For some applications, the techniques described with reference to FIGS. 12-13 are used to treat a subject who suffers from chronic obstructive pulmonary disease. For example, anatomical structure 604 may comprise a lung of the subject, and/or nerve tissue 602 may comprise the vagal nerve of the subject, and/or a branch thereof that innervates the lung. For some such applications, detecting the factor indicative of the parameter of the subject comprises detecting a breathing-related factor of the subject, such as airflow, breathing-related movement, a dimension of an airway of the subject (e.g., sensor 626 may comprise a breathing sensor or an imaging device, such as an ultrasound transceiver). For some such applications, detecting the factor indicative of the parameter of the subject comprises detecting blood chemistry of the subject (e.g., O2, CO2, or pH level).

For some applications, the techniques described with reference to FIGS. 12-13 are used to treat a subject who suffers from congestive heart failure. For example, anatomical structure 604 may comprise the heart of the subject, and/or nerve tissue 602 may comprise a sympathetic nerve that innervates the heart of the subject. For some such applications, detecting the factor indicative of the parameter of the subject comprises detecting a heart rate of the subject. For some such applications, detecting the factor indicative of the parameter of the subject comprises detecting a blood pressure of the subject.

For some applications, the techniques described with reference to FIGS. 12-13 are used to treat a subject who suffers from uterine bleeding. For example, anatomical structure 604 may comprise the uterus of the subject, and/or nerve tissue 602 may comprise a lumbar splanchnic nerve of the subject and/or a nerve that extends from a hypogastric plexus of the subject. For some such applications, detecting the factor indicative of the parameter of the subject comprises detecting a dimension of a blood vessel associated with the uterus (e.g., using ultrasound). For some such applications, detecting the factor indicative of the parameter of the subject comprises detecting blood pressure in a blood vessel associated with the uterus. For some such applications, detecting the factor indicative of the parameter of the subject comprises detecting bleeding (e.g., using a camera).

For some applications, the techniques described with reference to FIGS. 12-13 are used to treat a subject who suffers from nervous stomach. For example, anatomical structure 604 may comprise the stomach of the subject, and/or nerve tissue 602 may comprise vagus nerve tissue of the subject. For some such applications, detecting the factor indicative of the parameter of the subject comprises detecting gastric pH (e.g., sensor 626 may comprise a pH sensor). For some such applications, detecting the factor indicative of the parameter of the subject comprises detecting gastric movement.

For some applications, the techniques described with reference to FIGS. 12-13 are used to treat a subject who suffers from primary hyperhidrosis. For example, anatomical structure 604 may comprise one or more sweat glands of the subject, and/or nerve tissue 602 may comprise a superficial sympathetic nerve that innervates the sweat glands, e.g., a cholinergic sympathetic nerve and/or an adrenergic nerve of the subject. For some such applications, detecting the factor indicative of the parameter of the subject comprises detecting transepidermal water loss. For some such applications, detecting the factor indicative of the parameter of the subject comprises detecting perspiration (e.g., by detecting conduction of an electrical current between electrodes placed on the skin of the subject, e.g., sensor 626 may comprise electrodes and a current meter).

Typically, treatment is targeted to one or more areas of the body of the subject in which excess sweating is considered (e.g., by the subject and/or physician) to be particularly problematic. That is, typically, nerve tissue 602 comprises one or more nerves that innervate the sweat glands in these one or more areas. Typically, detection of perspiration and/or transepidermal water loss is performed in the same one or more areas.

For some applications, the techniques described with reference to FIGS. 12-13 are used to treat a subject who suffers from an inflammatory condition such as, but not limited to: fibrosis of the heart, inflammation of the heart, an autoimmune disease, an autoimmune inflammatory disease, multiple sclerosis, encephalitis, myelitis, immune-mediated neuropathy, myositis, dermatomyositis, polymyositis, inclusion body myositis, inflammatory demyelinating polyradiculoneuropathy, Guillain-Barre syndrome, myasthenia gravis, inflammation of the nervous system, inflammatory bowel disease, Crohn's disease, ulcerative colitis, SLE (systemic lupus erythematosus), rheumatoid arthritis, vasculitis, polyarteritis nodosa, Sjogren syndrome, mixed connective tissue disease, glomerulonephritis, thyroid autoimmune disease, sepsis, meningitis, a bacterial infection, a viral infection, a fungal infection, sarcoidosis, hepatitis, portal vein hypertension, appendicitis, peptic, gastric and duodenal ulcers, peritonitis, pancreatitis, pseudomembranous, acute and ischemic colitis, diverticulitis, epiglottitis, achalasia, cholangitis, coeliac disease, cholecystitis, enteritis, Whipple's disease, asthma, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, septic abortion, epididymitis, vaginitis, prostatitis, urethritis, diseases involving the respiratory system and associated tissues (such as bronchitis, emphysema, rhinitis, cystic fibrosis, adult respiratory distress syndrome, pneumonitis, pneumoultramicroscopic silicovolcanoconiosis, alvealitis, bronchiolitis, pharyngitis, pleurisy, and sinusitis), diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts), dermatological diseases and conditions of the skin (such as burns, dermatitis, sunburn, urticaria warts, and wheals), diseases involving the cardiovascular system and associated tissues (such as vasulitis, angiitis, endocarditis, arteritis, atherosclerosis, thrombophlebitis, pericarditis, myocarditis, myocardial ischemia, congestive heart failure, periarteritis nodosa, and rheumatic fever), diseases involving the central or peripheral nervous system and associated tissues (such as Alzheimer's disease, cerebral infarction, cerebral embolism, neuritis, neuralgia, spinal cord injury, paralysis, and uveitis), diseases of the bones, joints, muscles and connective tissues (such as the various arthritides and arthralgias, osteomyelitis, fasciitis, Paget's disease, gout, periodontal disease, and synovitis), other autoimmune and inflammatory disorders (such as thryoiditis, systemic lupus erythematosus, Goodpasture's syndrome, Behcets's syndrome, allograft rejection, graftversus-host disease, Type I diabetes, ankylosing spondylitis, Berger's disease, and Retier's syndrome), diabetes, cancer, septic shock, acute respiratory distress syndrome (ARDS), bacterial meningitis, acute pancreatitis, multiple organ failure (MOF), post-ischemic reperfusion, acute cellulitis, abdominal aortic aneurysm, septic or bacterial pyelonephritis, septic arthritis, uveitis, periodontitis, psoriasis, severe burns, skin ulceration, acute lung injury, pneumonia, trauma, severe early graft dysfunction, brochioeactasis, chronic obstructive pulmonary disease (COPD), complications with hemodialysis, hypersensitivity pneumonitis, lung fibrosis, herpes stromal keratitis, vascular restenosis, hypersensitivity, cardiac rupture arising as a complication with myocardial infarction, stroke or cerebral ischemia, and traumatic brain injury, arthritis (bursitis, gouty arthritis, polymyalgia rheumatic, etc.), autoimmune diseases, chronic inflammation, chronic prostatitis, nephritis, pelvic inflammatory disease, transplant rejection, and myocarditis. For example, anatomical structure 604 may comprise the spleen of the subject, and/or nerve tissue 602 may comprise tissue of the splenic nerve of the subject. For some such applications, detecting the factor indicative of the parameter of the subject comprises detecting an inflammatory cytokine, such as tumor-necrosis factor alpha (TNF-alpha), in the blood of the subject.

For some applications, the techniques described with reference to FIGS. 12-13 are used to treat a subject who suffers from obesity. For example, anatomical structure 604 may comprise an organ of the gastrointestinal system of the subject, such as the stomach or duodenum of the subject, and/or nerve tissue 602 may comprise a nerve that conducts action potentials between the organ of the gastrointestinal system and another part of the body of the subject, such as the celiac plexus of the subject. For example, nerve tissue 602 may comprise a vagus nerve or a branch thereof. For some such applications, detecting the factor indicative of the parameter of the subject comprises detecting an EMG value (e.g., of a muscle associated with the gastrointestinal system). For some such applications, detecting the factor indicative of the parameter of the subject comprises detecting the factor using ultrasound (e.g., sensor 626 may comprise an ultrasound transceiver).

For some applications of the invention the nerve tissue being treated (e.g., excited and ablated) is accessed transluminally, and the excitatory current and ablation energy are applied from within a blood vessel. For example, as described hereinabove, nerve tissue associated with the renal artery (i.e., the renal nerve) is accessed via the renal artery. Other nerves which may be treated as described hereinabove via transluminal access include, but are not limited to nerves which are associated with: the superior mesenteric vein, posterior, anterior, inferior pancreaticoduodenal veins, middle colic vein, right colic vein, ileocolic vein, anterior, posterior cecal veins, hepatic portal vein, posterior superior pancreaticoduodenal vein, prepyloric vein, anterior superior pancreaticoduodenal vein, hepatic portal vein, posterior superior pancreaticoduodenal vein, superior mesenteric vein, anterior superior pancreaticoduodenal vein, anterior inferior pancreaticoduodenal vein, posterior inferior pancreaticoduodenal vein, a vein that vascularizes the duodenum.

Figure 14:
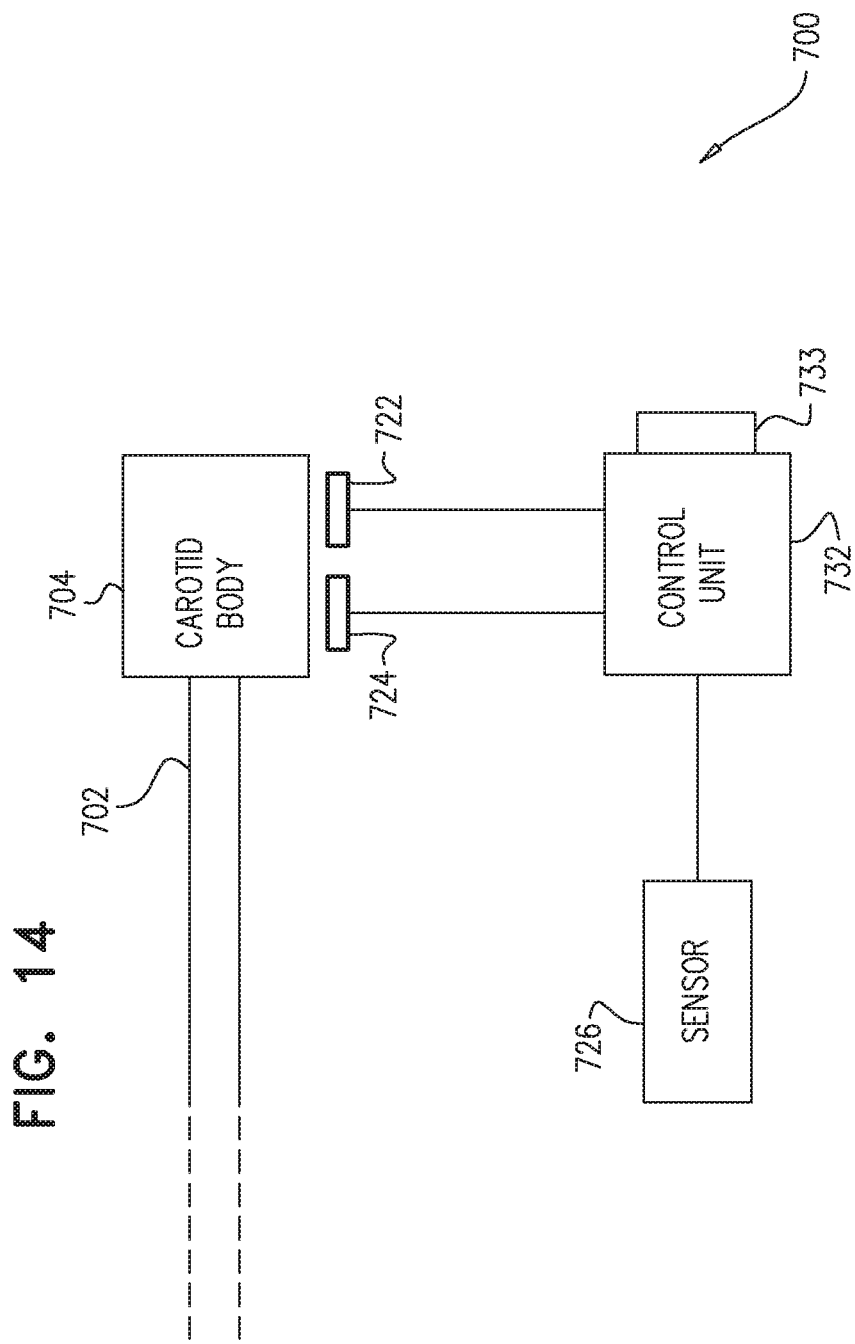
FIG. 14 is a schematic illustration of a system for controlled ablation of tissue of a carotid body of a subject, in accordance with some applications of the invention.

Reference is made to FIG. 14, which is a schematic illustration of a system 700 for controlled ablation of tissue of a carotid body 704 of a subject, such as chemoreceptors and/or glomus cells, e.g., to treat a subject who suffers from hypertension, in accordance with some applications of the invention. Carotid body 704 is capable of modulating blood pressure of the subject by inducing action potentials in a nerve 702 of the subject in response to detected levels of oxygen partial pressure, carbon dioxide partial pressure, pH, and temperature. Nerve 702 may comprise a glossopharyngeal nerve of the subject and/or a branch thereof that innervates the carotid body (e.g., the Nerve of Hering).

System 700 comprises at least one electrode unit 722, an ablation unit 724, and a control unit 732, configured to drive and/or control the electrode unit and/or the ablation unit. For some applications, control unit 732 comprises an interface 733. Typically, system 700 further comprises a sensor 726, configured to detect a factor indicative of the parameter of the subject (e.g., the sensor is configured to detect blood pressure of the subject). For some applications, system 700 does not comprise a sensor, and the parameter is detected by a sensor that is not a component of system 700, and/or is detected by a medical professional. For such applications, information relating to the factor (e.g., a value of the factor, such as a blood pressure value) may be inputted manually or automatically via interface 733.

Electrode unit 722 and ablation unit 724 are advanced to a vicinity of carotid body 704 (e.g., to within 1 cm of the carotid body (e.g., to within 1 mm of the carotid body, such as to be in contact with the carotid body)). For some applications, electrode unit 722 and ablation unit 724 are advanced toward the carotid body transluminally, typically remaining within a blood vessel (e.g., the carotid artery) for the duration of the procedure. For some applications, electrode unit 722, ablation unit 724, control unit 732 and/or sensor 726 of system 700 comprise a respective identically-named corresponding component of one or more other systems described hereinabove. For some applications, electrode unit 722, ablation unit 724, control unit 732 and sensor 726 of system 700 are arranged (e.g., coupled to each other) as described for identically-named corresponding components of one or more other systems described hereinabove. For example, electrode unit 722, ablation unit 724, control unit 732 and sensor 726 may be coupled to and disposed along a longitudinal member, such as catheter 28 (not shown in FIG. 14).

For some applications, system 700 does not comprise distinct electrode and ablation units, but rather comprises one effector unit that functions, under control of control unit 732, as both electrode unit 722 and ablation unit 724. The effector unit may, for some applications, comprise a single electrode. That is, for some applications, control unit 732 drives the effector unit (e.g., an electrode thereof) to apply, as appropriate, the excitatory current and the ablating energy.

System 700 is typically used in combination with techniques described hereinabove, mutatis mutandis. For example, with reference to the steps shown in FIG. 13, mutatis mutandis:

Carotid body 704 is stimulated by electrode unit 722 applying an excitatory current to the carotid body (step 642). The excitatory current typically has a frequency of greater than 1 Hz and/or less than 100 Hz, such as between 1 and 100 Hz, e.g., between 10 and 100 Hz. After a start of the application of the excitatory current, a detection of a factor indicative of the parameter of the subject is performed, e.g., using sensor 726 (step 642). For some applications, the detection is performed during the application of the excitatory current. For some applications, the detection is performed after the excitatory current has stopped being applied. At least in part in response to the detection of the factor, ablating energy is applied to carotid body 704 by ablation unit 724 (step 644). Typically, the ablating energy has characteristics similar to (e.g., the same as) those of ablating energy described elsewhere hereinabove.

For some applications, before application of the excitatory current in step 642, a detection of the factor is performed (e.g., while the subject is at rest and/or untreated) (step 640). Reference numeral 660 indicates a technique in which a first detection is performed before application of the excitatory current, a second detection of the factor is performed after the start of the application of the excitatory current, and subsequently ablating energy is applied. For some applications of technique 660, ablating energy is applied 644 at least in part responsively to the detection in step 640 and at least in part responsively to the detection in step 642. For example, ablating energy may be applied in response to a comparison of the first detection and the second detection, e.g., in response to a difference between a first detected value of the factor and a second detected value of the factor. For example, technique 660 may be used to screen subjects likely to be responsive to a treatment comprising ablation of carotid body 704 (e.g., by determining a sensitivity of the parameter to action potentials initiated by the carotid body).

For some applications, subsequent to the application of ablating energy in step 644, another application of excitatory current and detection of the factor are performed (step 646). Typically, step 646 is identical in nature to step 642. For such applications, at least in part in response to the detection in step 646 (and typically also at least in part in response to previous detection(s) of the factor), ablating energy is applied to carotid body 704 by ablation unit 724 (step 648). Reference numeral 662 indicates a technique in which steps 646 and 648 are performed after step 644. Ablating energy of step 648 may be applied in response to a difference between a value of the factor detected in step 646 and a value of the factor detected in step 642. For example, this difference may indicate a degree of ablation achieved by the application of ablating energy, as described hereinabove.

Reference is again made to FIGS. 1, 5A-B, 6, 7, 8, and 9A-B. For some applications of the invention, at least ablation unit 24 of one or more of the intravascular devices described hereinabove may be configured to be implanted in renal artery 8. For such applications, ablation unit 24 comprises or is coupled to an antenna, configured to wirelessly receive energy (e.g., from an extracorporeal transmitter), and to responsively apply an application of the ablation energy. For some such applications, one or more characteristics (e.g., intensity) of the ablation energy is controllable via the extracorporeal transmitter. For some such applications, the entire intravascular device is implantable in renal artery 8.

For example, ablation unit 24 and/or the entire intravascular device may comprise a stent, transluminally advanceable via a catheter independently of other components of the described system (such as catheter 28 and/or sensor 26). Alternatively, ablation unit 24 and/or the entire intravascular device may be (i) coupled to catheter 28 as shown in FIGS. 1, 5A-B, 6, 7, and 8, and (ii) implantable in renal artery 8 by being decoupled from the longitudinal member while disposed within the renal artery.

It will be understood that, although the terms "first," "second," etc. may be used herein to describe various elements, these elements should not be limited by these terms. These terms are generally only used to distinguish one element from another. Thus, a "first" element (e.g., a first electrode unit) discussed herein could also be termed a "second" element (e.g., a second electrode unit) without departing from the teachings of the present disclosure.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for facilitating ablation of nerve tissue of a subject, the apparatus comprising:
   an ablation unit, configured to be percutaneously advanced to a site adjacent to a first portion of the nerve tissue of the subject;
   at least one electrode unit, coupled to the ablation unit, and configured to be percutaneously advanced to a site adjacent to a second portion of the nerve tissue of the subject, and to initiate unidirectional action potentials in the nerve tissue, such that the unidirectional action potentials propagate toward the first portion of the nerve tissue; and
   a control unit, configured:
      to drive the ablation unit to ablate, at least in part, the first portion of the nerve tissue of the subject, and
      to drive the at least one electrode unit to initiate the unidirectional action potentials by applying an excitatory current to the second portion of the nerve tissue.

2. The apparatus according to claim 1, wherein the at least one electrode unit comprises a first electrode unit and a second electrode unit, the first electrode unit being coupled to the ablation unit on a first side of the ablation unit, and the second electrode unit being coupled to the ablation unit on a second side of the ablation unit, each electrode unit being configured to initiate unidirectional action potentials in the nerve tissue, such that the action potentials propagate toward the first portion of the nerve tissue.

3. The apparatus according to claim 1, wherein the ablation unit comprises a radio-frequency ablation unit, and wherein the control unit is configured to drive the radio-frequency ablation unit to ablate the first portion of the nerve tissue by applying an ablative radio-frequency current to the first portion of the nerve tissue.

4. The apparatus according to claim 1, wherein the ablation unit comprises an ultrasound ablation unit, and wherein the control unit is configured to drive the ultrasound ablation unit to ablate the first portion of the nerve tissue by applying ablative ultrasound energy to the first portion of the nerve tissue.

5. The apparatus according to claim 1, wherein the electrode unit is configured to apply a non-ablative blocking current to the second portion of the nerve tissue of the subject, the non-ablative blocking current being configured to reversibly block endogenous action potentials from propagating through the second portion of the nerve tissue, and wherein the control unit is configured to drive the at least one electrode unit to apply the non-ablative blocking current.

6. The apparatus according to claim 1, wherein the site includes a blood vessel, the nerve tissue includes nerve tissue of the blood vessel, and the at least one electrode unit comprises a plurality of sub-electrodes configured to be arranged in a broken arc that traces an inner wall of the blood vessel.

7. The apparatus according to claim 6, wherein the control unit is configured to drive the plurality of sub-electrodes to simultaneously apply the excitatory current.

8. The apparatus according to claim 7, wherein each of the plurality of sub-electrodes is independently addressable by the control unit.

9. The apparatus according to claim 7, wherein the control unit is configured to balance the excitatory current across the plurality of sub-electrodes.

10. The apparatus according to claim 1, wherein the nerve tissue includes nerve tissue of a blood vessel of the subject, and wherein at least the ablation unit is configured to be transluminally delivered to the blood vessel of the subject.

11. The apparatus according to claim 10, wherein the electrode unit is configured to be transluminally delivered to the blood vessel of the subject.

12. The apparatus according to claim 10, wherein the blood vessel includes a renal artery of the subject, and wherein at least the ablation unit is configured to be transluminally delivered to the renal artery of the subject.

13. The apparatus according to claim 1, further comprising a longitudinal member, having a distal portion that is configured to be percutaneously advanced toward the nerve tissue of the subject, and wherein the ablation unit and the at least one electrode unit are coupled to the longitudinal member.

14. The apparatus according to claim 13, wherein:
the ablation unit comprises a first ablation unit, and the at least one electrode unit comprises a respective first at least one electrode unit,
the apparatus further comprises a second ablation unit and a second respective at least one electrode unit, and
the distal portion of the longitudinal member is bifurcated so as to have (i) a first distal portion that is coupled to the first ablation unit and the first at least one electrode unit, and (ii) a second distal portion that is coupled to the second ablation unit and the second at least one electrode unit, each of the distal portions being configured to be transluminally advanced into a respective renal artery of the subject.

15. The apparatus according to claim 1, further comprising a sensor, configured to detect a physiological response of the subject to the unidirectional action potentials initiated by the electrode unit.

16. The apparatus according to claim 15, further comprising a longitudinal member, configured to be percutaneously advanced toward the nerve tissue of the subject, and wherein the ablation unit, the electrode unit, and the sensor are coupled to the longitudinal member.

17. The apparatus according to claim 15, wherein the sensor is configured to be disposed in an aorta of the subject.

18. The apparatus according to claim 15, wherein the sensor comprises a blood pressure sensor.

19. The apparatus according to claim 15, wherein the control unit is configured to receive information indicative of the detected physiological response, and to drive the ablation unit at least in part responsively to the information indicative of the detected physiological response.

20. The apparatus according to claim 19, wherein the control unit is configured:
to drive, during a first period, the at least one electrode unit to apply a non-ablative blocking current to the second portion of the nerve tissue of the subject, the blocking current being configured to temporarily block endogenous action potentials from propagating through the second portion of the nerve tissue,
to receive a first value of a factor indicative of the response, the first value being detected after a start of the application of the non-ablative blocking current, and
to drive the ablation unit at least in part responsively to the received first value.

21. The apparatus according to claim 20, wherein the control unit is configured:
to drive, during a second period, the at least one electrode unit to apply the excitatory current,
to receive a second value of the factor, the second value being detected after a start of the application of the excitatory current, and
to drive the ablation unit at least in part responsively to the received second value.

22. The apparatus according to claim 20, wherein the sensor is configured to detect the first value of the factor after the start of the application of the non-ablative blocking current, and to provide the first value of the factor to the control unit.

* * * * *